(12) United States Patent
Figdor et al.

(10) Patent No.: US 12,102,688 B2
(45) Date of Patent: Oct. 1, 2024

(54) IMMUNOMODULATORY NANOFILAMENTS

(71) Applicant: STICHTING RADBOUD UNIVERSITAIR MEDISCH CENTRUM, Nijmegen (NL)

(72) Inventors: Carl Figdor, Nijmegen (NL); Roel Hammink, Nijmegen (NL); Loek Eggermont, Nijmegen (NL)

(73) Assignee: STICHTING RADBOUD UNIVERSITAIR MEDISCH CENTRUM, Nijmegen (NL)

( * ) Notice: Subject to any disclaimer, the term of this patent is extended or adjusted under 35 U.S.C. 154(b) by 963 days.

(21) Appl. No.: 16/967,509

(22) PCT Filed: Feb. 6, 2019

(86) PCT No.: PCT/EP2019/052922
§ 371 (c)(1),
(2) Date: Aug. 5, 2020

(87) PCT Pub. No.: WO2019/154865
PCT Pub. Date: Aug. 15, 2019

(65) Prior Publication Data
US 2022/0401570 A1  Dec. 22, 2022

(30) Foreign Application Priority Data
Feb. 6, 2018 (GB) ................ 1801902

(51) Int. Cl.
*A61K 47/68* (2017.01)

(52) U.S. Cl.
CPC ...... *A61K 47/6813* (2017.08); *A61K 47/6849* (2017.08); *A61K 47/6883* (2017.08)

(58) Field of Classification Search
CPC ........... A61K 47/6813; A61K 47/6849; A61K 47/6883; A61K 47/64
See application file for complete search history.

(56) References Cited

U.S. PATENT DOCUMENTS

| | | | |
|---|---|---|---|
| 2010/0105869 A1 | 4/2010 | Kim et al. | |
| 2013/0202548 A1* | 8/2013 | Rowan | A61K 47/59 424/78.17 |

FOREIGN PATENT DOCUMENTS

| | | | | |
|---|---|---|---|---|
| WO | 2012/004369 | 1/2012 | | |
| WO | 2014/160132 | 10/2014 | | |
| WO | WO-2018013797 A1 * | 1/2018 | ............. | A61K 35/17 |

OTHER PUBLICATIONS

Hammink R et al. Affinity-Based Purification of Polyisocyanopeptide Bioconjugates (Bioconjugate Chem. 2017, 28, 10, 2560-2568) (Year: 2017).*
Hammink R et al. Controlling T-Cell Activation with Synthetic Dendritic Cells Using the Multivalency Effect (ACS Omega 2017, 2, 3, 937-945) (Year: 2017).*
Eggermont LJ et al. Towards efficient cancer immunotherapy: advances in developing artificial antigen-presenting cells (Trends in Biotechnology, 2014 32(9) 456-465) (Year: 2014).*
Mandal S et al. Therapeutic nanoworms: towards novel synthetic dendritic cells for immunotherapy (Chem. Sci., 2013, 4, 4168) (Year: 2013).*
Steenblock ER et al. An Artificial Antigen-presenting Cell with Paracrine Delivery of IL-2 Impacts the Magnitude and Direction of the T Cell Response. (JBC 2011 286 (40) 34883-34892) (Year: 2011).*
International Search Report and the Written Opinion of the International Searching Authority, issued Apr. 5, 2019 in corresponding International Patent Application No. PCT/EP2019/052922.
Search Report issued Oct. 17, 2018 in corresponding United Kingdom Patent Application No. GB1801902.6.
Mandal et al., "Therapeutic Nanoworms: Towards Novel Synthetic Dendritic Cells for Immunotherapy", Chemical Science, DOI: 10.1039/C3SC51399H, Jul. 2013, pp. 1-22.

* cited by examiner

*Primary Examiner* — Karen A. Canella
*Assistant Examiner* — John J Skoko, III
(74) *Attorney, Agent, or Firm* — Wenderoth, Lind & Ponack, L.L.P.

(57) ABSTRACT

Immunomodulatory nanofilaments are provided which present immune factors, especially cytokines, to immune cells, particularly T cells, so as to modulate the immune response of said cells. Methods of using such nanofilaments are also provided.

17 Claims, 30 Drawing Sheets

A

B

1 - IL-2 (100%)
2 - IL-2 (50%)
3 - IL-2 (25%)
4 - IL-2 (12.5%)
5 - P-αCD3/IL-2low
6 - P-αCD3/IL-2med
7 - P-αCD3/IL-2high
8 - P-IL-2low
9 - P-IL-2high

Figure 8:
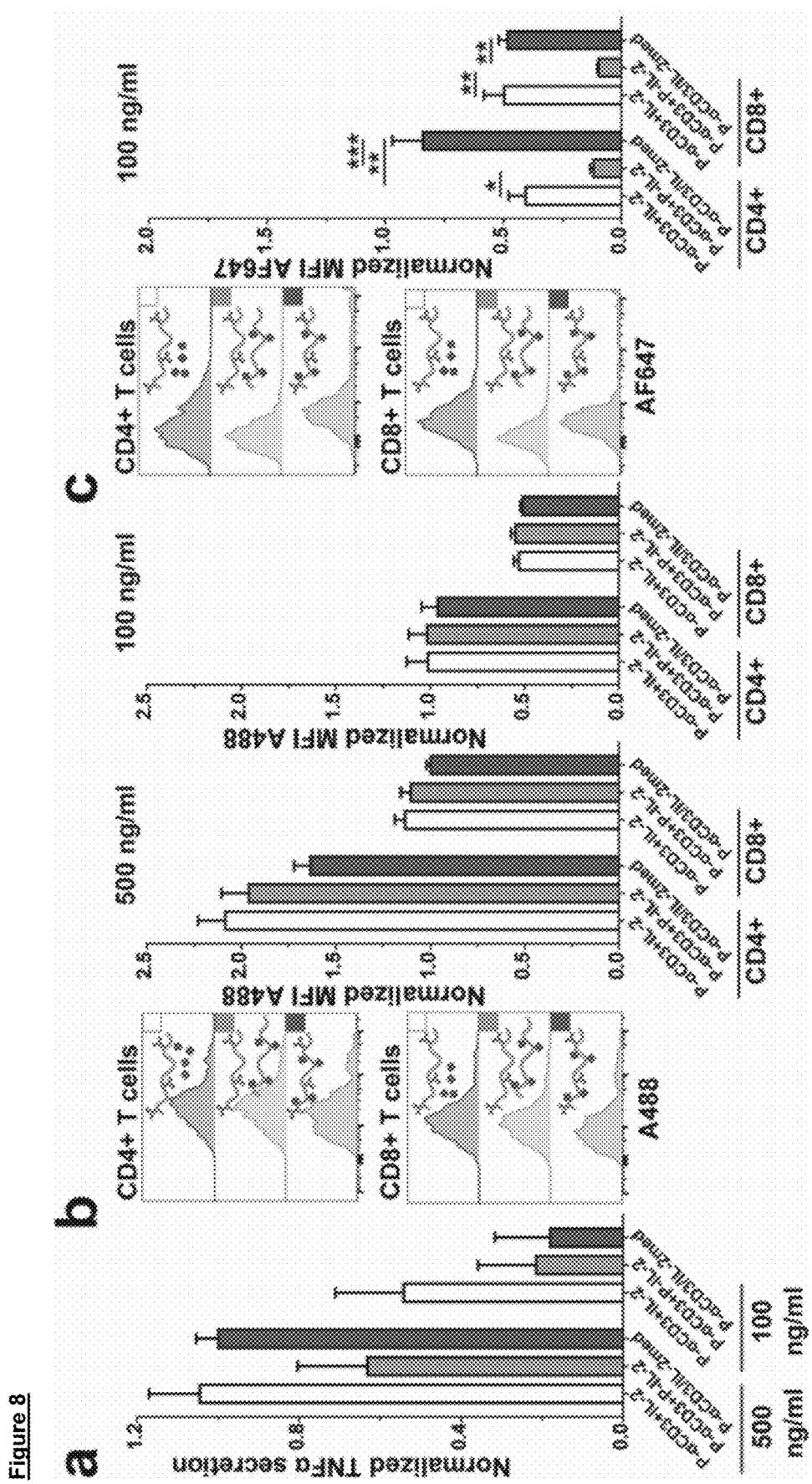
Figure 8:
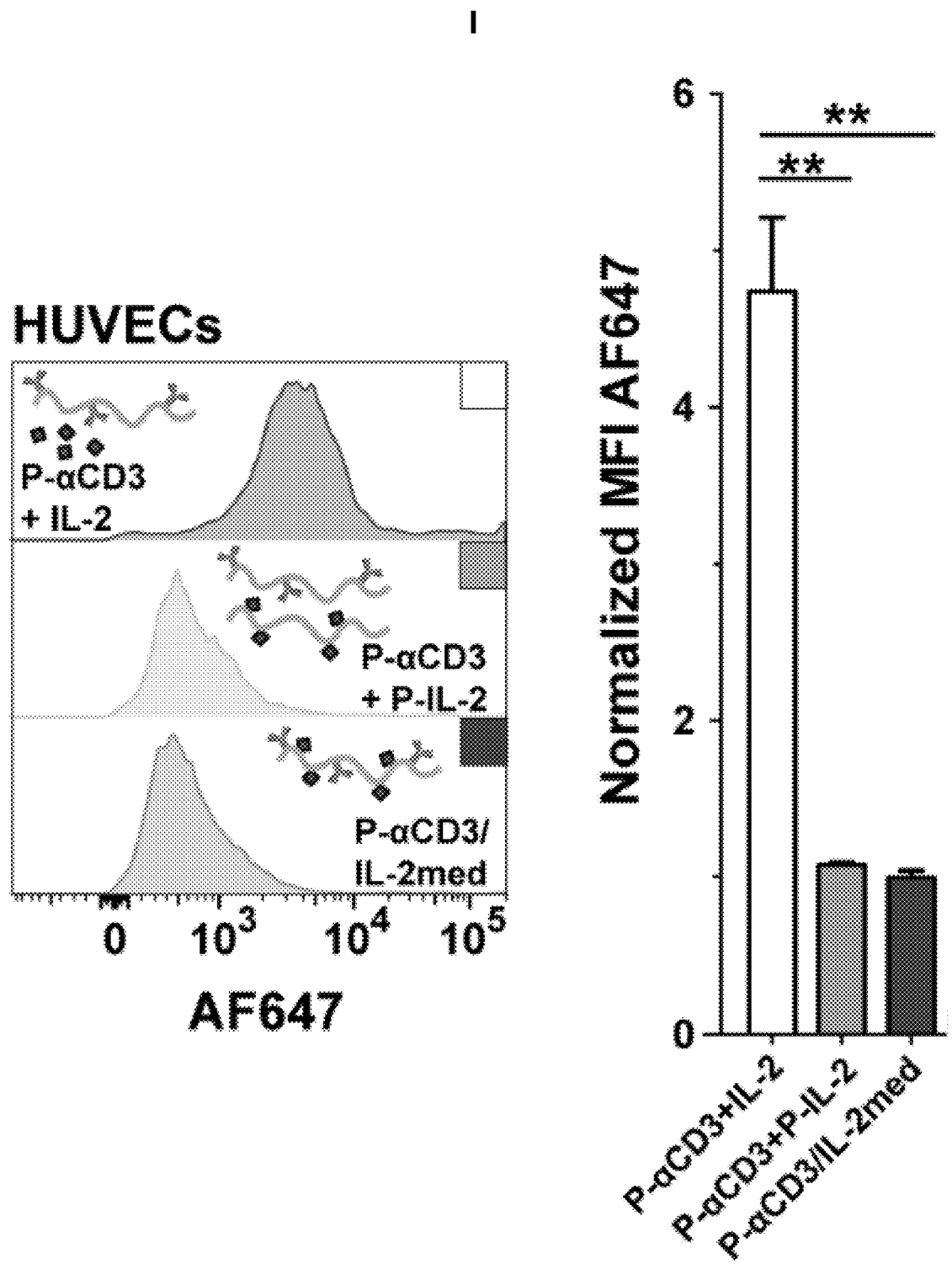

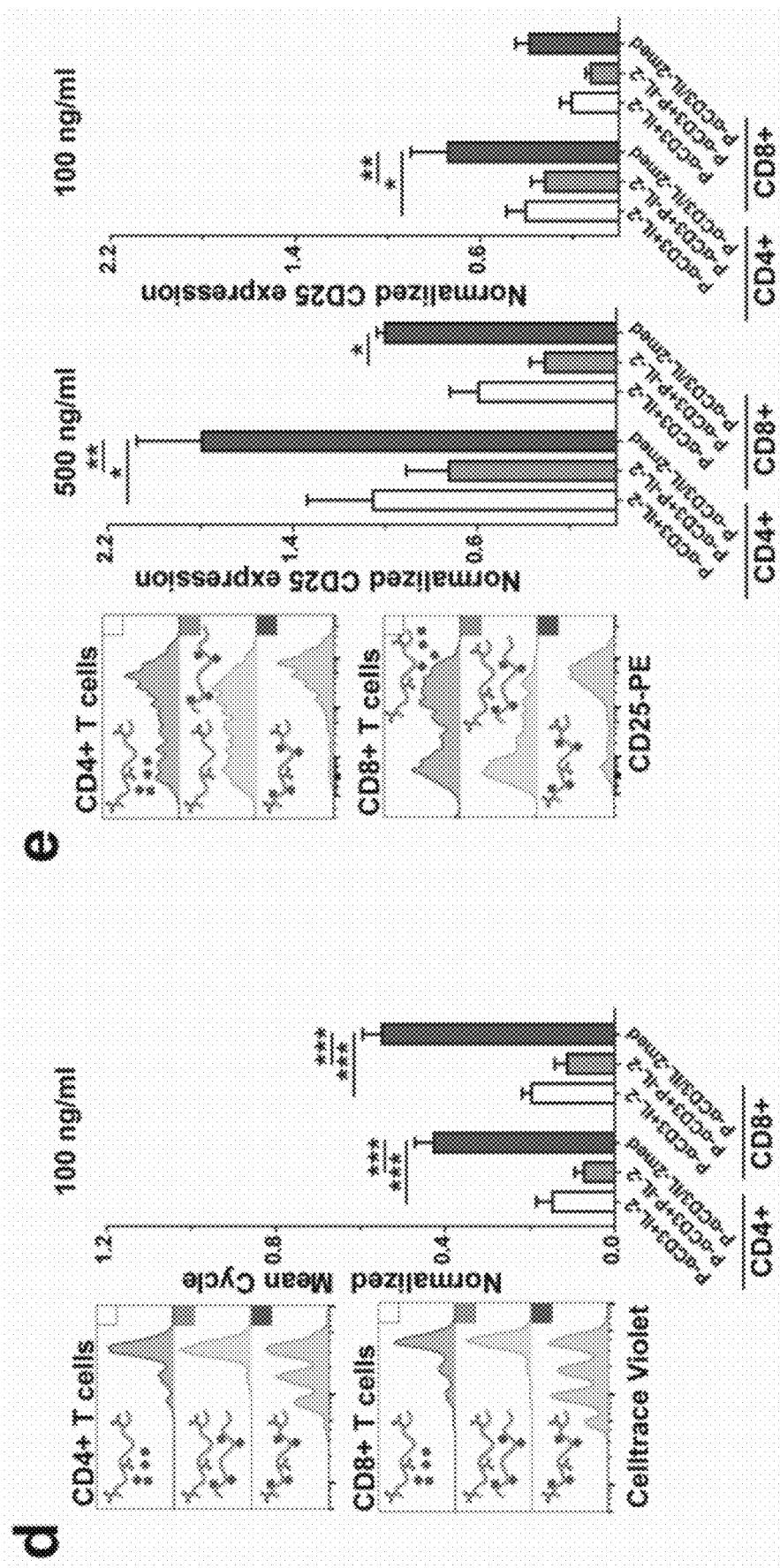
Figure 8 – (cont'd)

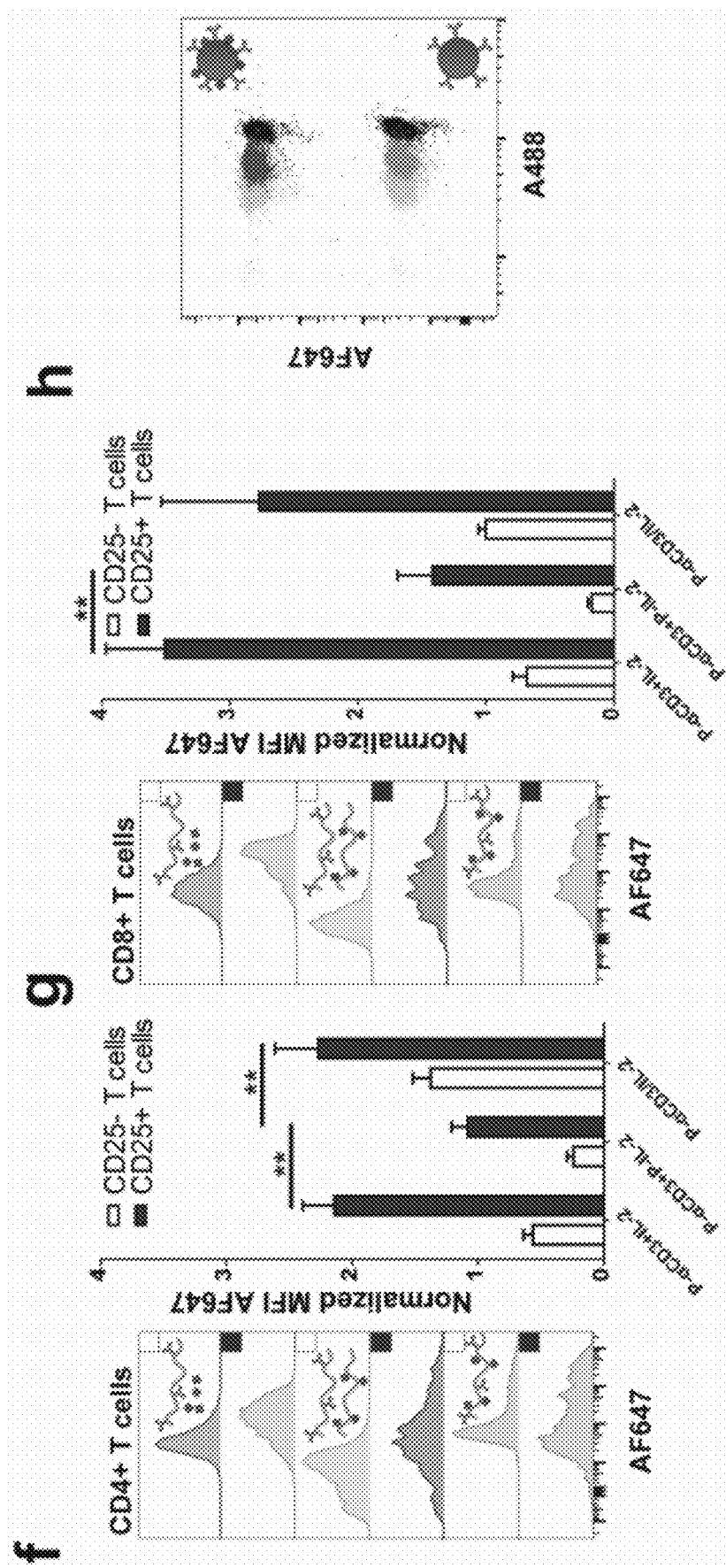
Figure 8 – (cont'd)

Figure 10:
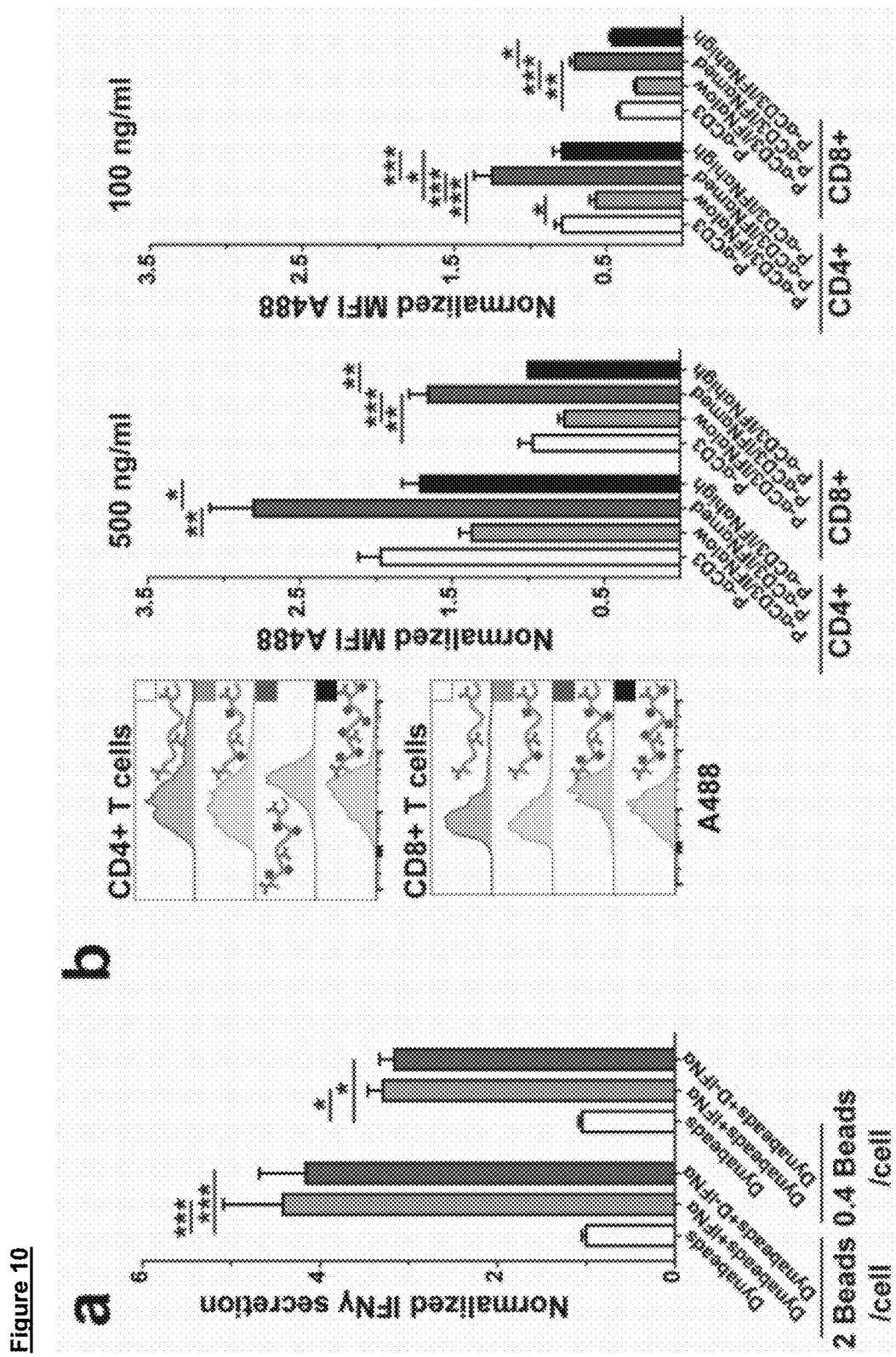

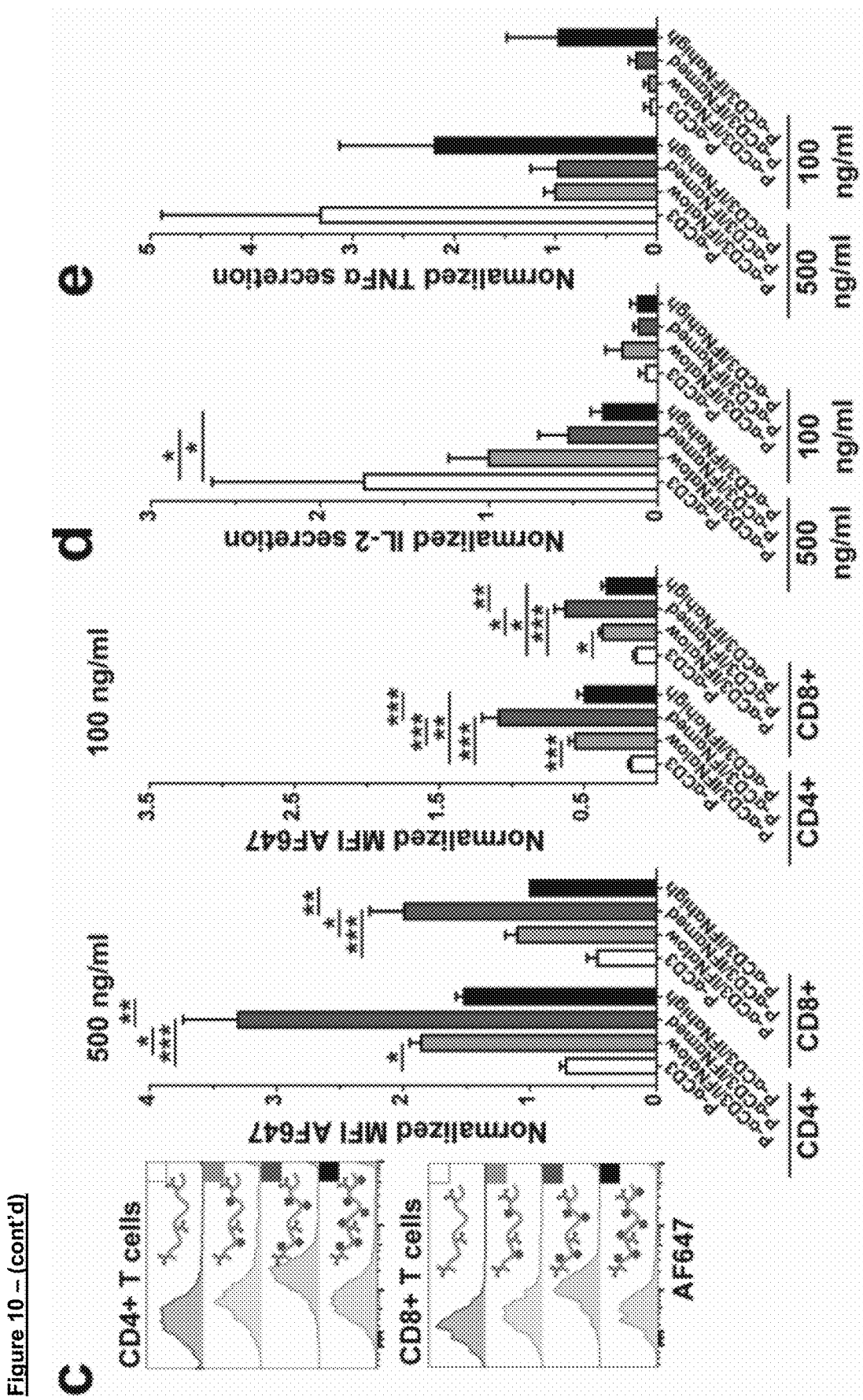
Figure 10 – (cont'd)

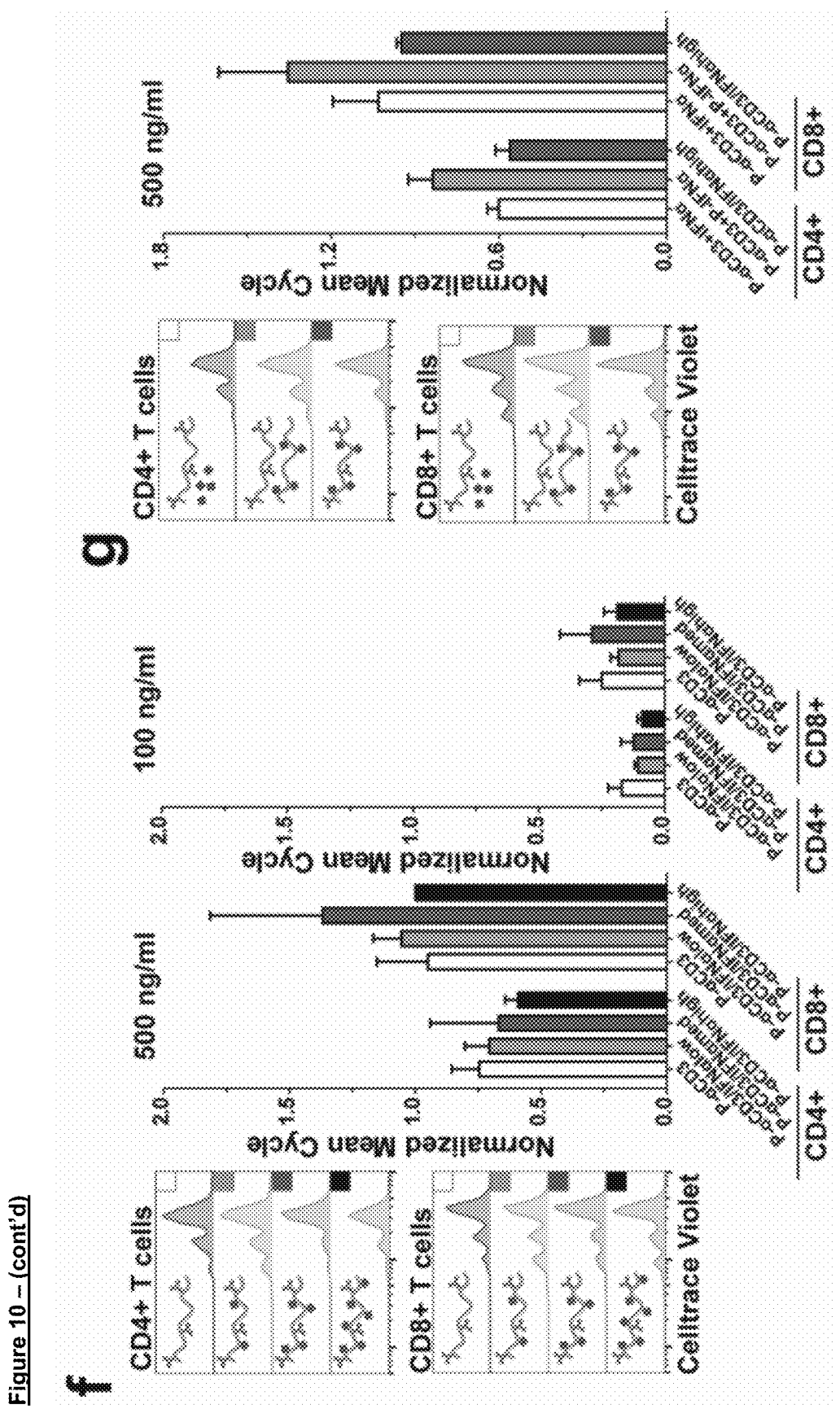
Figure 10 – (cont'd)

Figure 13:
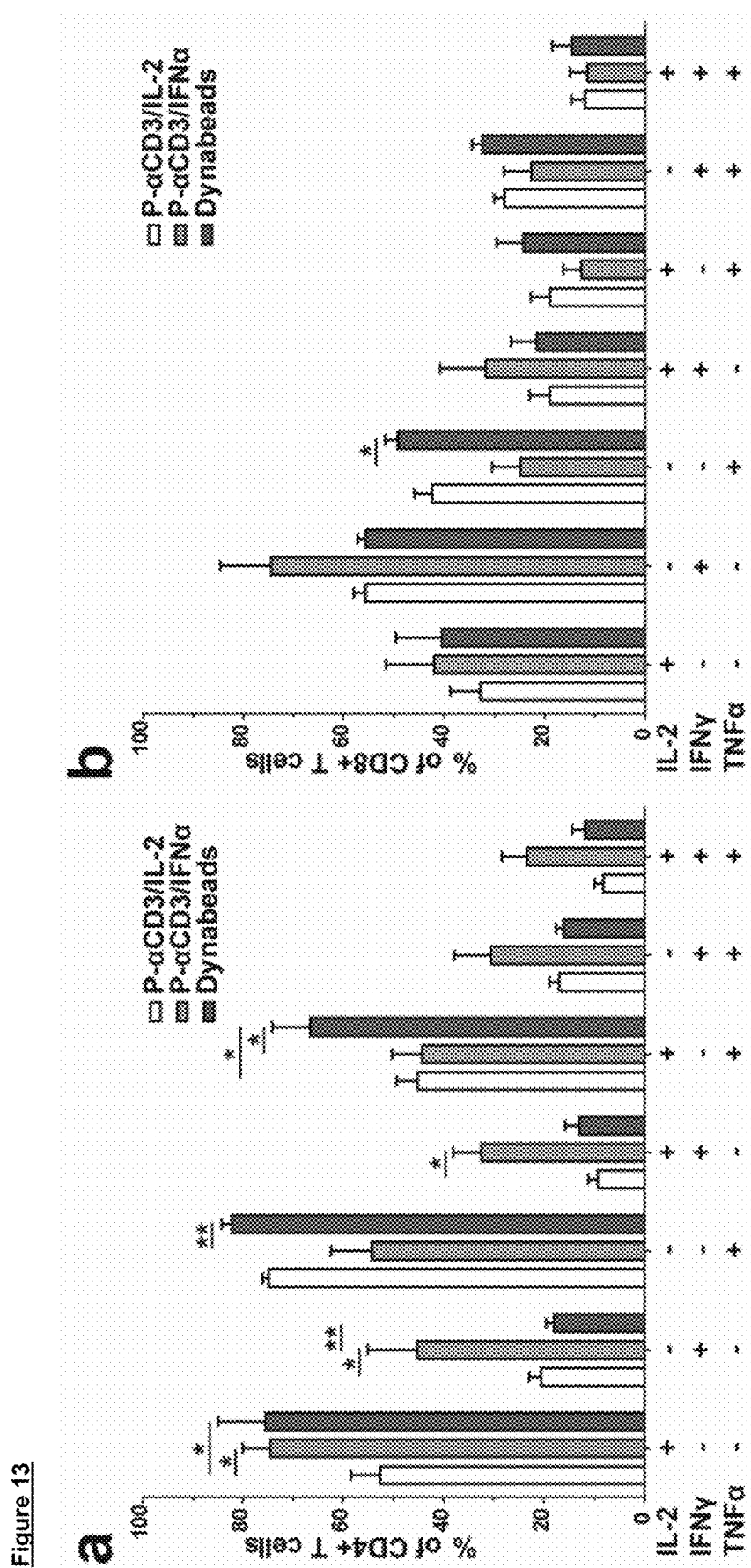

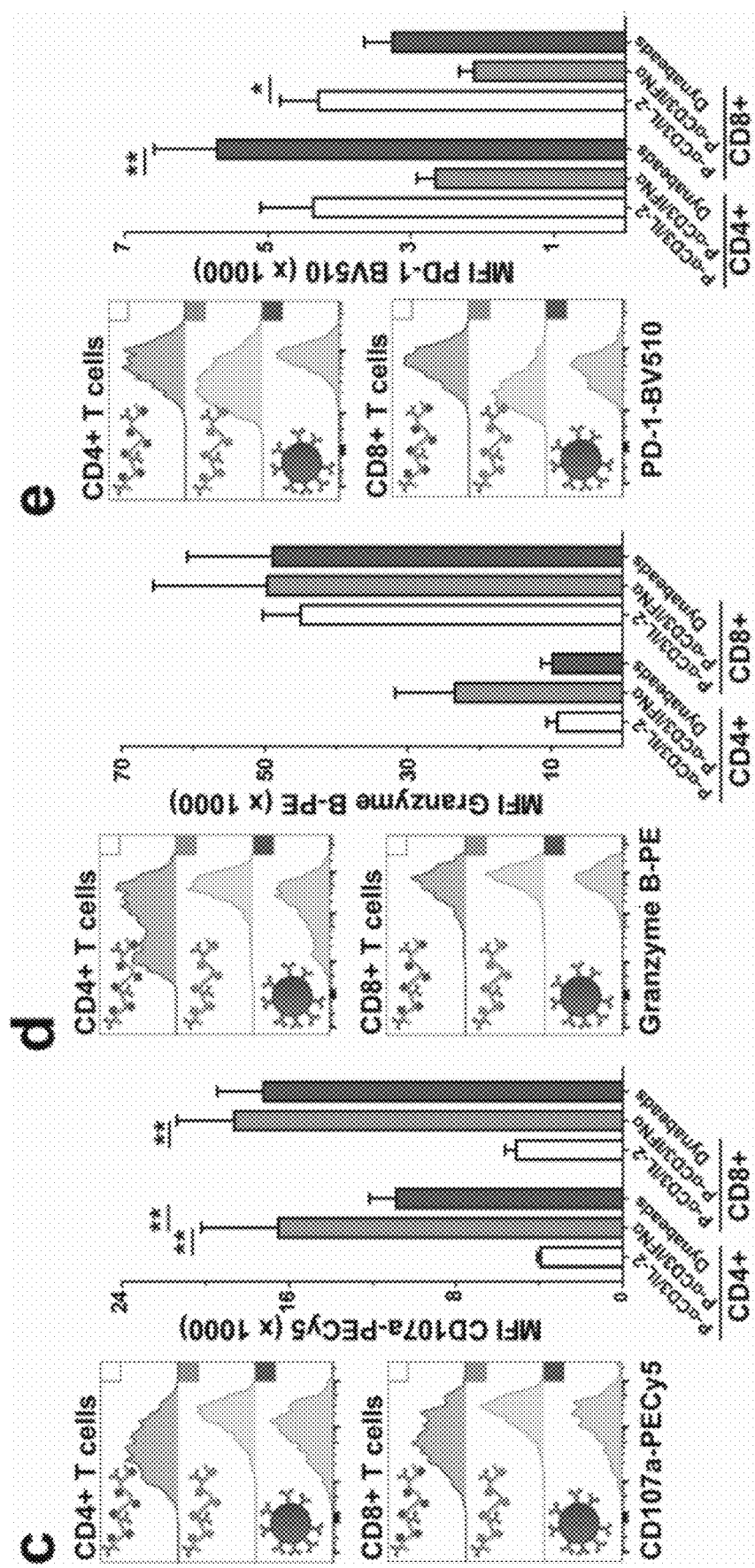
Figure 13 – (cont'd)

Figure 14:
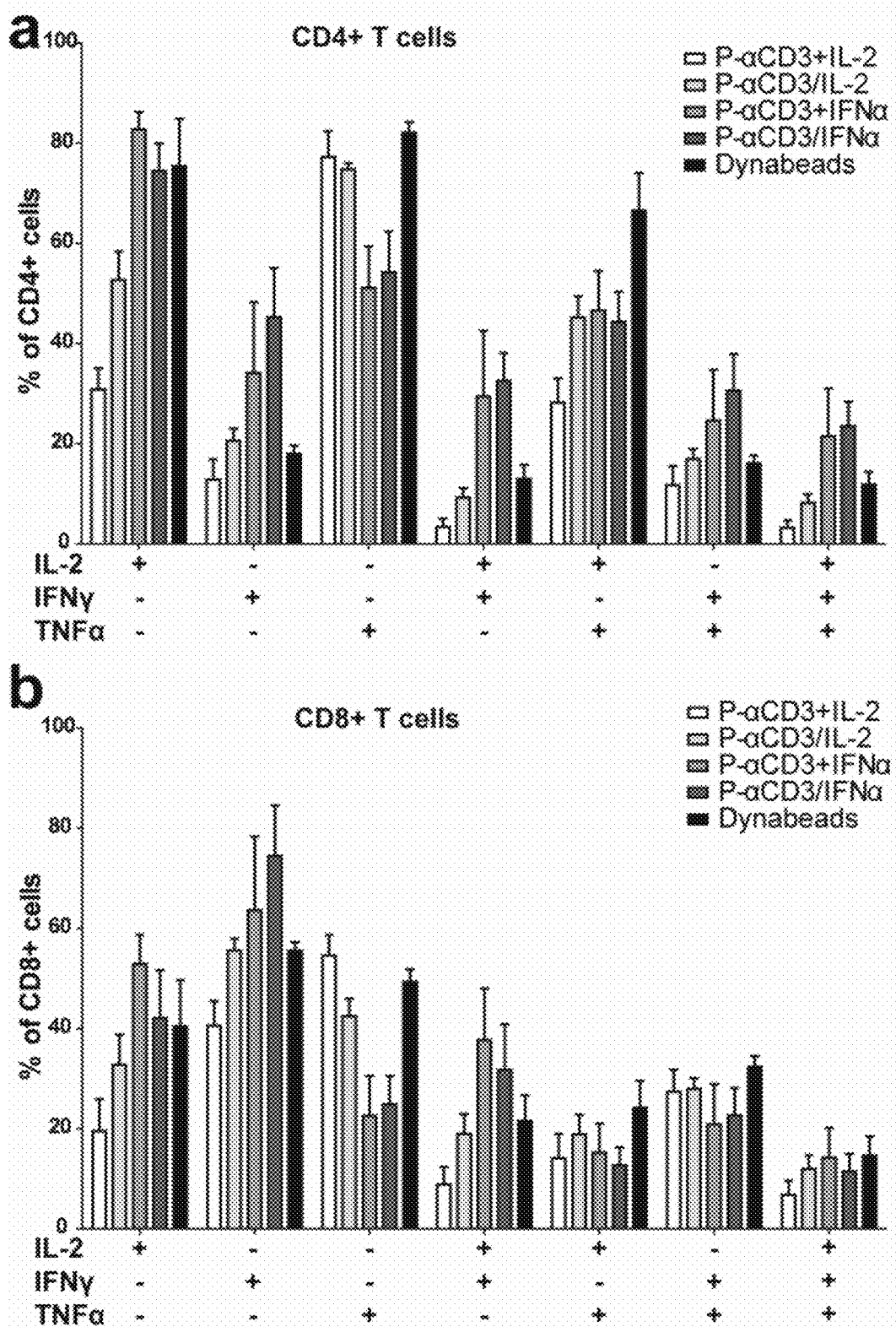

Figure 14 – (cont'd)
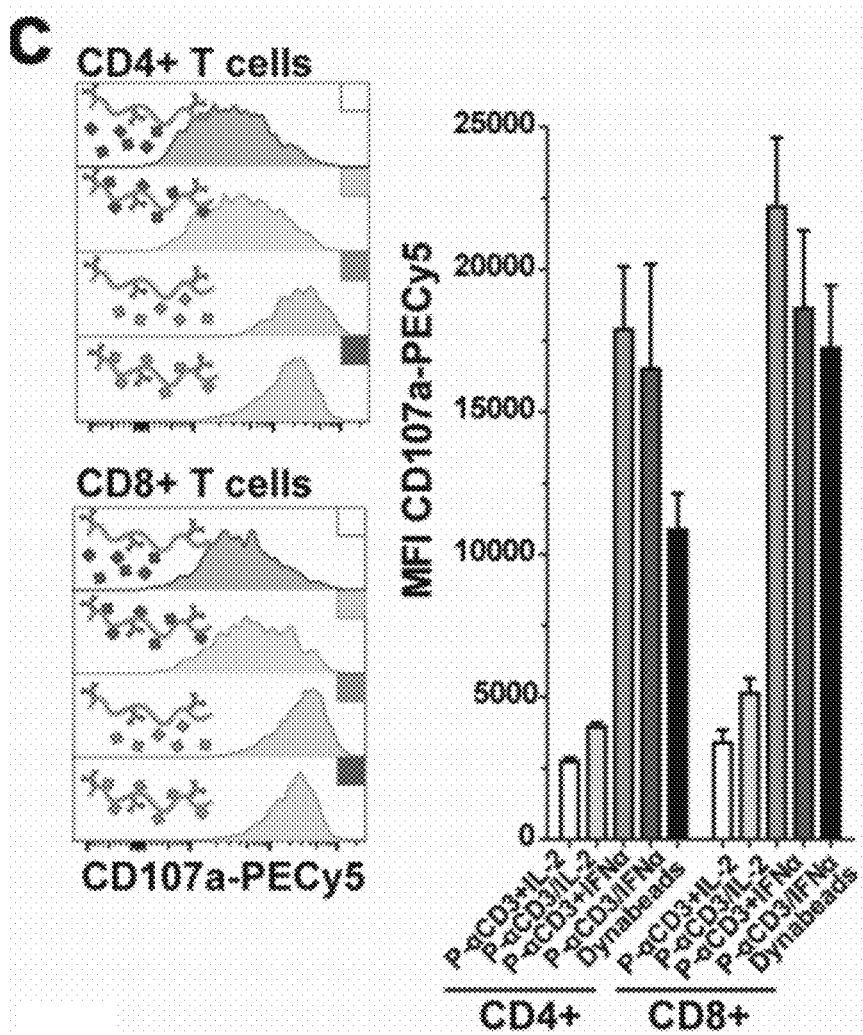

Figure 14 – (cont'd)
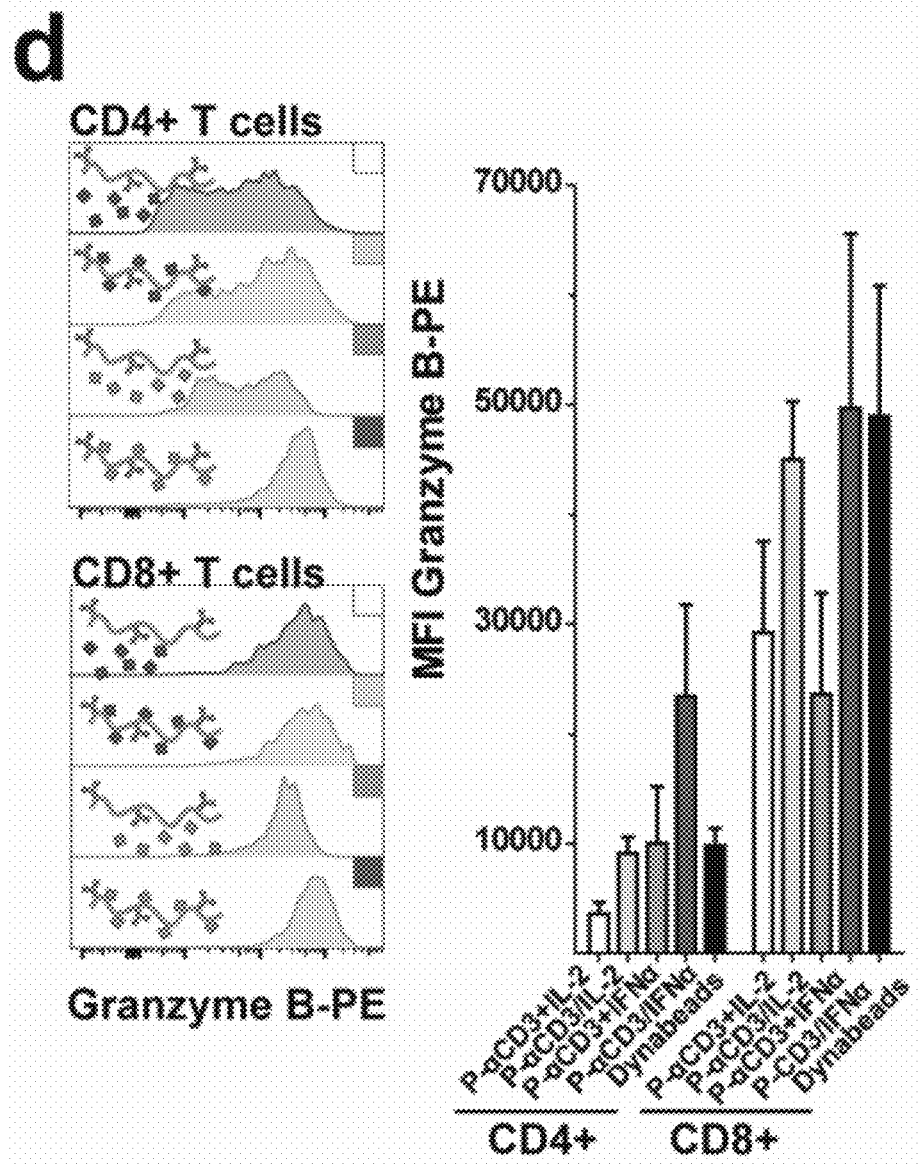

Figure 14 – (cont'd)
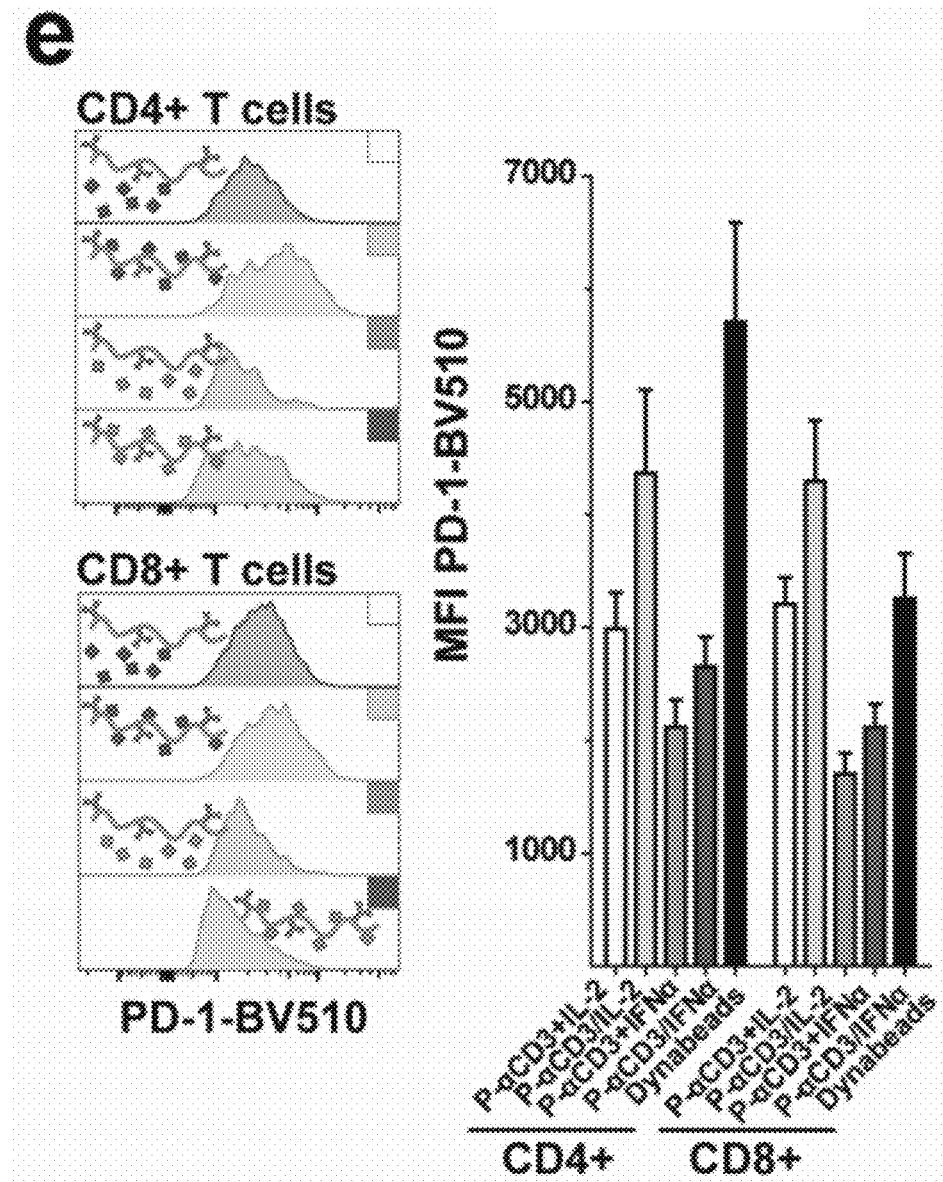

C

IMMUNOMODULATORY NANOFILAMENTS

FIELD OF INVENTION

The present invention is directed to immunomodulatory nanofilaments that serve to present immune factors, especially cytokines, to immune cells, particularly T cells, so as to modulate the immune response of said cells. The invention further relates to methods of using such nanofilaments, for example in therapy (ex vivo or in vivo) or in a laboratory context.

BACKGROUND

Cytokines are small soluble proteins that mediate immune responses and communication between immune cells such as T cells, B cells, macrophages, dendritic cells and mast cells. Cytokines act through receptors present on the surface of these cells, and can have a range of effects, often pleiotropic. For instance, certain cytokines are associated with pro-inflammatory conditions (e.g. IFNα, IFNγ, IL-2, IL-12, TNFα), some cytokines with immune cell maintenance and expansion (e.g. IL-17 and IL-15), while others may be associated with anti-inflammatory or regulatory conditions (e.g. IL-4, IL-6, IL-1 and IL-10). Similarly, cytokines are known to affect the balance between cellular (e.g. T cell) and humoral (antibody and B cell) immune responses, with IL-2, IFNγ and TNFα associated with a type 1 cellular response, and TGFβ, IL-6, and IL-13 associated with a type 2 humoral response.

Manipulation of cytokines has been an important technique in the modulation of immune cells, both in a laboratory investigative setting as well as when influencing a subject's immune response for therapeutic purposes.

For almost three decades, high-dose cytokine treatment regimens have been applied as cancer immune therapies to treat different malignancies. High doses of interleukin-2 (IL-2) have induced cancer regression in a small portion of patients, and even led to complete remission of the disease in rare cases. Besides being used as a mono-therapy, bolus IL-2 injections are also used to support the survival of adoptively transferred T cells. However, tumour reduction requires cytokine doses that induce severe IL-2-related toxicities. The most common side effects include capillary leak syndrome, which is caused by the direct binding of IL-2 to CD25-positive endothelial cells combined with high concentrations of secondary cytokines, and multi-organ failure, originating from the infiltration of lymphocytes and direct IL-2 stimulation of endothelial cells.

Similarly, interferon-α (IFNα) has been used in clinical trials with varying success. It has mostly been applied in haematological malignancies and as a post-surgery treatment option for solid tumours. For this cytokine, patients often experience severe flu-like symptoms, induced by the broad immunological activity of IFNα.

These dose-dependent side effects pose one of the biggest challenges for the widespread and safe clinical application of cytokines. Due to the need for close monitoring, this frequently results in the hospitalization of patients. Regardless of their clinical efficacy, many clinicians are still hesitant to systemically apply cytokine-based immunotherapies because of their severe side effects.

Previously, efforts to solve this problem have included immobilization of cytokines on rigid scaffolds such as microbeads. However, this has been largely unsuccessful because it diminished cytokine activity. Also, the size of micro-scale beads limits their use in in vivo settings.

The nanofilaments provided herein address some or all of the above problems in the art.

WO2012/004369 describes PIC polymers with CD3 antibodies attached, as well as PIC polymers with MHC-antigen complexes attached.

Mandal et al., *Chem. Sci.*, 2013,4, 4168-4174, describes PIC polymers with CD3 antibodies attached.

Mandal et al *ACS Chem Biol*. 2015 Feb 20;10(2):485-92 describes PIC polymers with CD3 antibodies and CD28 antibodies attached.

Hammink et al ACS Omega 2017, 2, 937-945, describes PIC polymers with CD3 antibodies attached.

WO2018/115146 describes fully-flexible dextran polymer scaffolds with cytokines non-covalently associated.

SUMMARY OF INVENTION

It is demonstrated herein that when cytokines are conjugated onto a nanofilament comprising a polymer backbone they retain their biological activity. Without being bound by theory, this effect is thought to be because such nanofilaments are semi-flexible—that is, they provide sufficient flex to allow for dynamic rearrangement of receptor-bound ligands attached to the polymer, but are not so flexible that they coil into a polymer ball. This is in contrast to rigid scaffolds such as microbeads. The dynamic rearrangement permitted by the nanofilaments is important for realistic immune cell interaction, for example when presenting multiple molecules at an immunological synapse. Because of this more realistic immune cell interaction, the nanofilaments provided herein are also referred to as synthetic dendritic cells, or sDCs.

Furthermore, it is also demonstrated herein that cytokines attached to a nanofilament can be combined with binding molecules also attached to the nanofilament to target a particular immune cell subset, such as targeting T cells with anti-CD3 antibodies. For example, nanofilaments provided herein are demonstrated to induce robust T cell activation and proliferation using a combination of a proinflammatory cytokine and a T cell-specific binding molecule. When targeting T cells by using a binding molecule, the nanofilaments provided herein can be considered to be acting as artificial antigen presenting cells, or aAPCs.

Targeting particular immune cell subsets using binding molecules bound to the nanofilament is particularly advantageous, since doing so will limit the off-target effects of the cytokine, thereby reducing potential side-effects. Furthermore, use of a binding molecule that targets T cells (for example an anti-CD3 antibody or an MHC-antigen complex) is surprisingly effective at promoting T cell activation. As noted above, this is hypothesised as being due to the nanofilaments allowing for dynamic rearrangement of the various immune factors so as to realistically imitate an immune synapse. This is particularly important in the context of promoting T cell activation, where multiple activation signals are needed. In this context, the binding molecule can serve both to target T cells and to provide an activation signal.

Because the nanofilaments provided herein efficiently present immobilized cytokines and can be used to target specific immune cell subsets, they form a powerful tool to improve both cytokine-based therapies and in vitro and ex vivo manipulation of immune cell populations.

Accordingly, in a first aspect there is provided a nanofilament comprising a plurality of molecules of a first cytokine attached to a polymeric backbone. In certain embodiments the nanofilament further comprises a plurality of a binding molecule attached to the polymeric backbone, wherein the binding molecule binds to a molecule presented by an immune cell.

In a further aspect, there is provided a composition comprising one or more of the nanofilaments of the first aspect.

In a further aspect there is provided a nanofilament or composition as provided herein for use in therapy.

In a further aspect there is provided a nanofilament or composition as provided herein for use in treating immunosuppression.

In a further aspect there is provided a nanofilament or composition as provided herein for use in treating cancer.

In a further aspect there is provided a method of modulating an immune response in a human subject comprising contacting a population of immune cells, preferably T cells, with a nanofilament or composition as provided herein.

In a further aspect is provided a method of treating cancer in a human subject comprising contacting a population of immune cells, preferably T cells, with a nanofilament or composition as provided herein.

In a further aspect is provided a method of treating immunosuppression in a human subject comprising contacting a population of immune cells, preferably T cells, with a nanofilament or composition as provided herein.

In a further aspect is provided a method of treating a disease in a subject comprising contacting a population of T cells with a nanofilament provided herein wherein the binding protein is an MHC-antigen complex, or a composition comprising said nanofilament, wherein the disease is characterised by the presence of the antigen of the MHC-antigen complex.

In a further aspect is provided an in vitro or ex vivo method of modulating immune cells, preferably T cells, said method comprising contacting the cells with a nanofilament or composition provided herein.

In a preferred embodiment of all aspects, the nanofilament is a PIC nanofilament.

DETAILED DESCRIPTION

Figures

Figure 1:
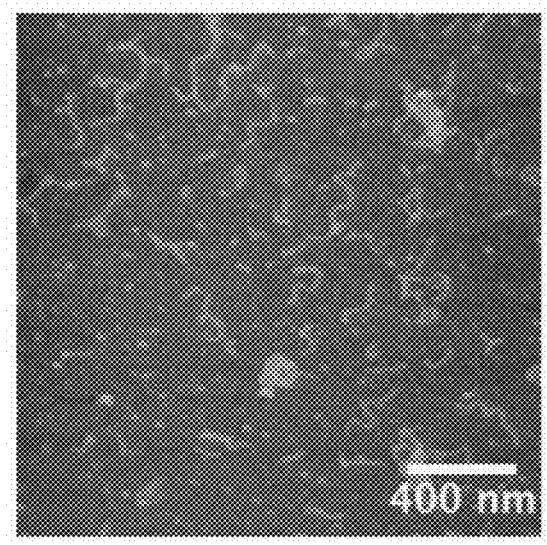
Figure 1:
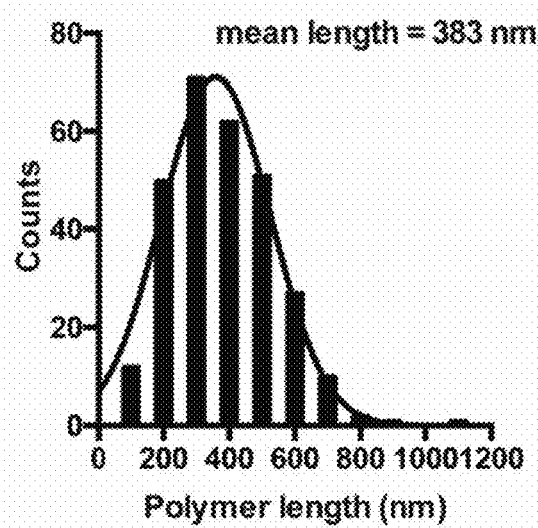

FIG. 1: (A) Representative AFM image showing the filamentous polymer structure, scale bar 400 nm; (B) Histogram of polymer length analysis, fitted with a Gaussian distribution.

Figure 2:
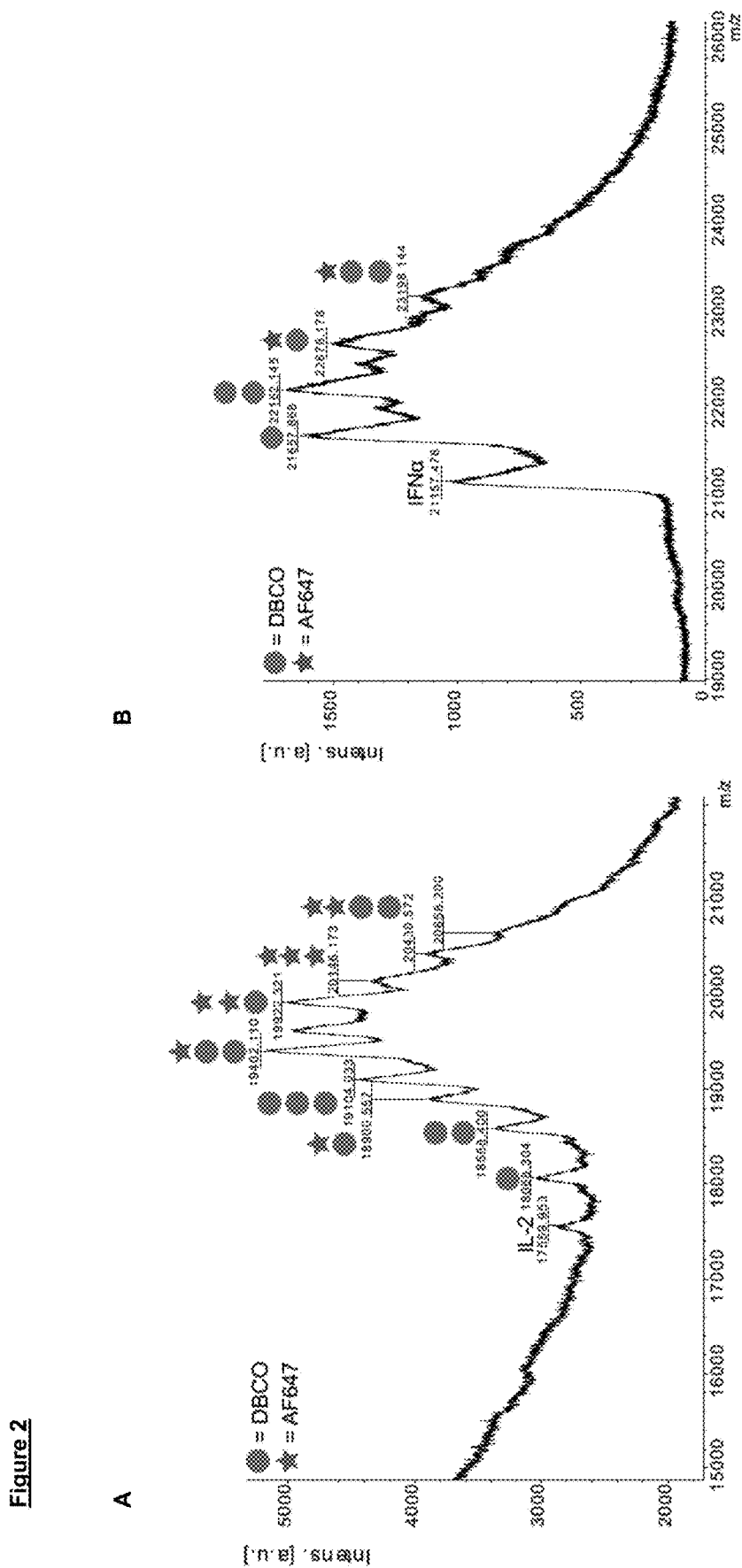

FIG. 2: Degree of labelling of IL-2 and IFNα with DBCO and dye. (A) Maldi-ToF spectra of functionalized IL-2. (B) Maldi-ToF spectra of functionalized IFNα. Red circles are assigned when the mass of DBCO was added to the cytokine, blue stars are assigned for AF647.

Figure 3:
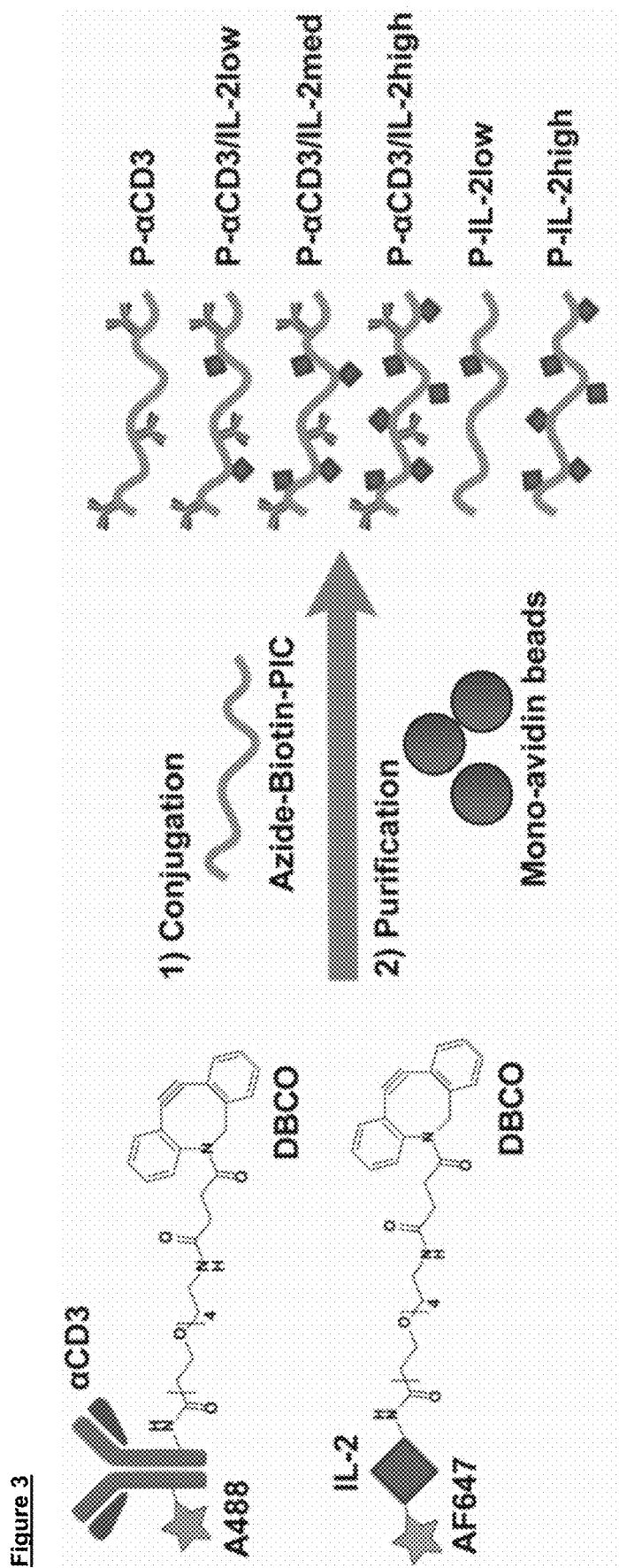

FIG. 3: DBCO- and dye-functionalized IL-2 and αCD3 antibodies were covalently coupled to biotin- and azide-functionalized polyisocyanopeptides (PICs) via strain-promoted azide alkyne cycloaddition. The resulting PIC-protein conjugates were purified over magnetic mono-avidin beads. Schematic structures of P-αCD3, P-αCD3/IL-2low, P-αCD3/IL-2med, P-αCD3/IL-2high, P-IL-2low and P-IL-2high are depicted on the right.

Figure 4:
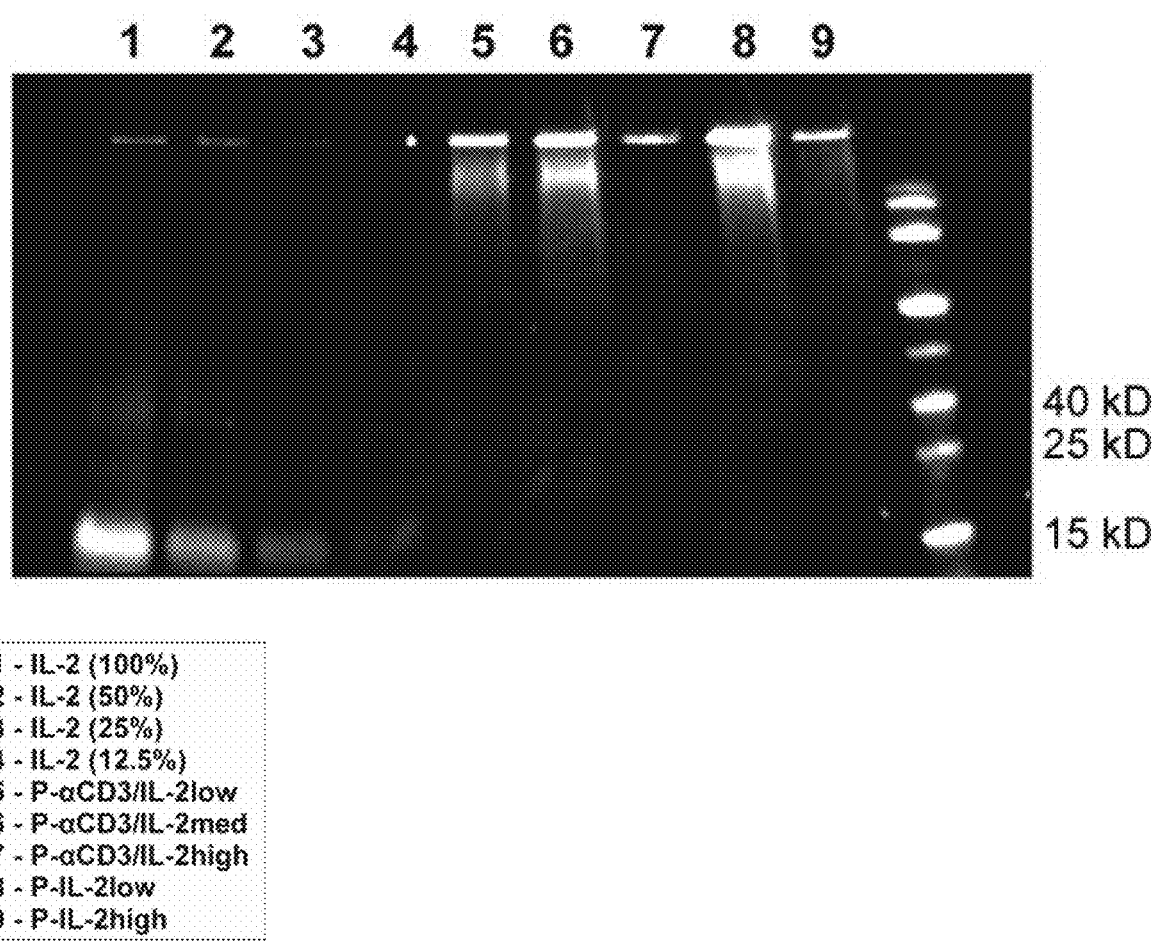

FIG. 4: SDS-PAGE of purified P-IL-2 conjugates (lanes 5-9). Lanes 1-4 were loaded with unbound IL-2 as a standard. The IL-2 concentrations of P-IL-2 conjugates correspond to 100% IL-2 (lane 1), except for lane 5 (loading of 63%).

Figure 5:
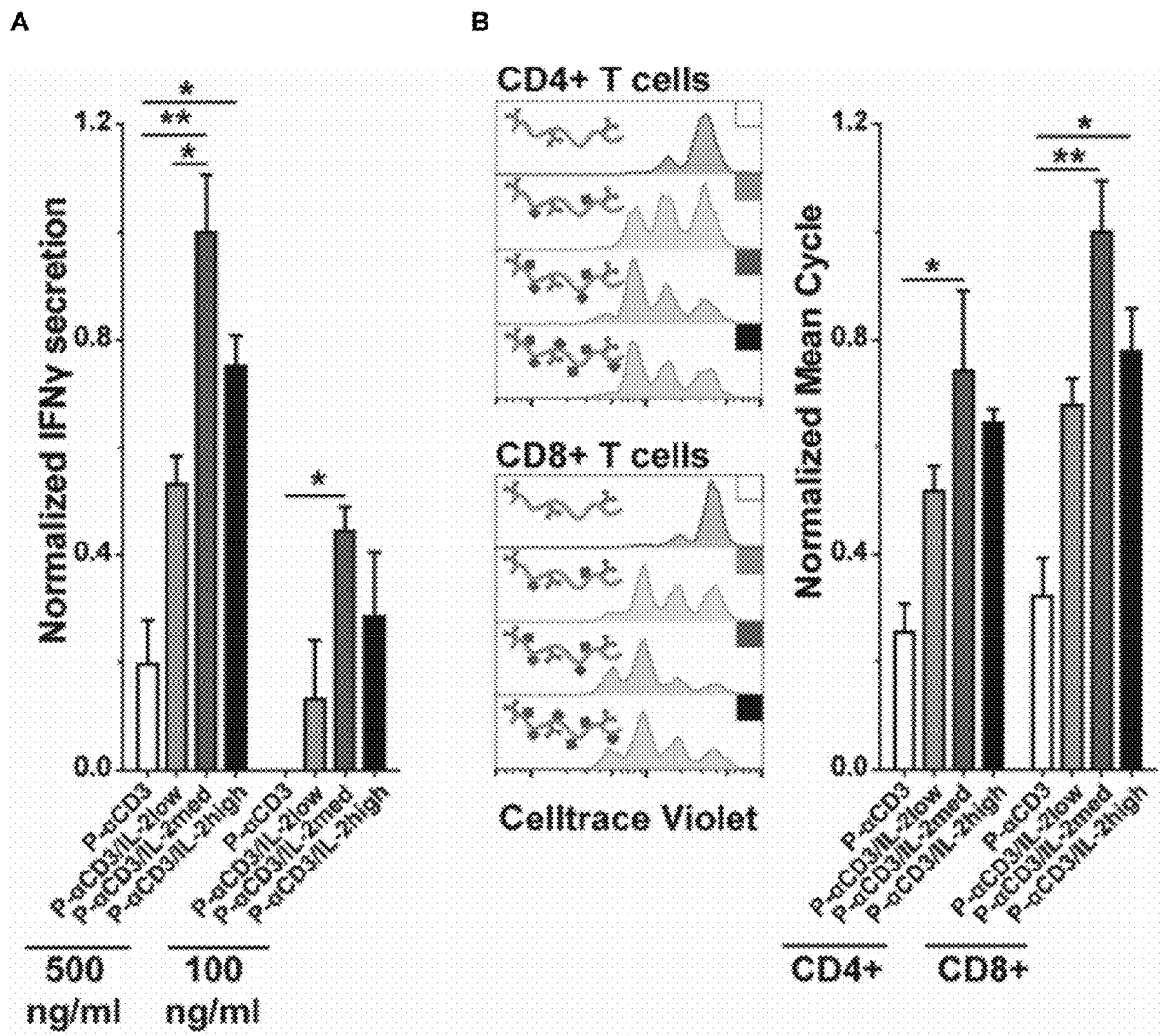

FIG. 5: (A) IFNγ secretion into the supernatant after stimulation of T cells for 16 h with αCD3-functionalized sDCs containing different amounts of IL-2. The cells were stimulated using 500 ng/ml αCD3 or 100 ng/ml αCD3. (B) Proliferation of T cells after 72 h of stimulation with αCD3-functionalized sDCs containing different amounts of IL-2. Proliferation was determined using flow cytometry analysis, measuring the dilution of Celltrace Violet (x-axis of histograms). The histograms show one representative experiment of duplicate stimulation of T cells from three healthy donors for CD4+ T cells (upper panel) and CD8+ T cells (lower panel). The mean number of cycles was calculated for each experiment. After T cell stimulation, the values were normalized, using the stimulation with 500 ng/ml of P-αCD3/IL-2med (CD8+ T cells) as the reference. The normalized values of duplicate stimulations of three donors were pooled to obtain mean and SEM values as depicted in the bar graphs. *$p<0.05$, $p<0.01$, *$p<0.001$.

Figure 6:
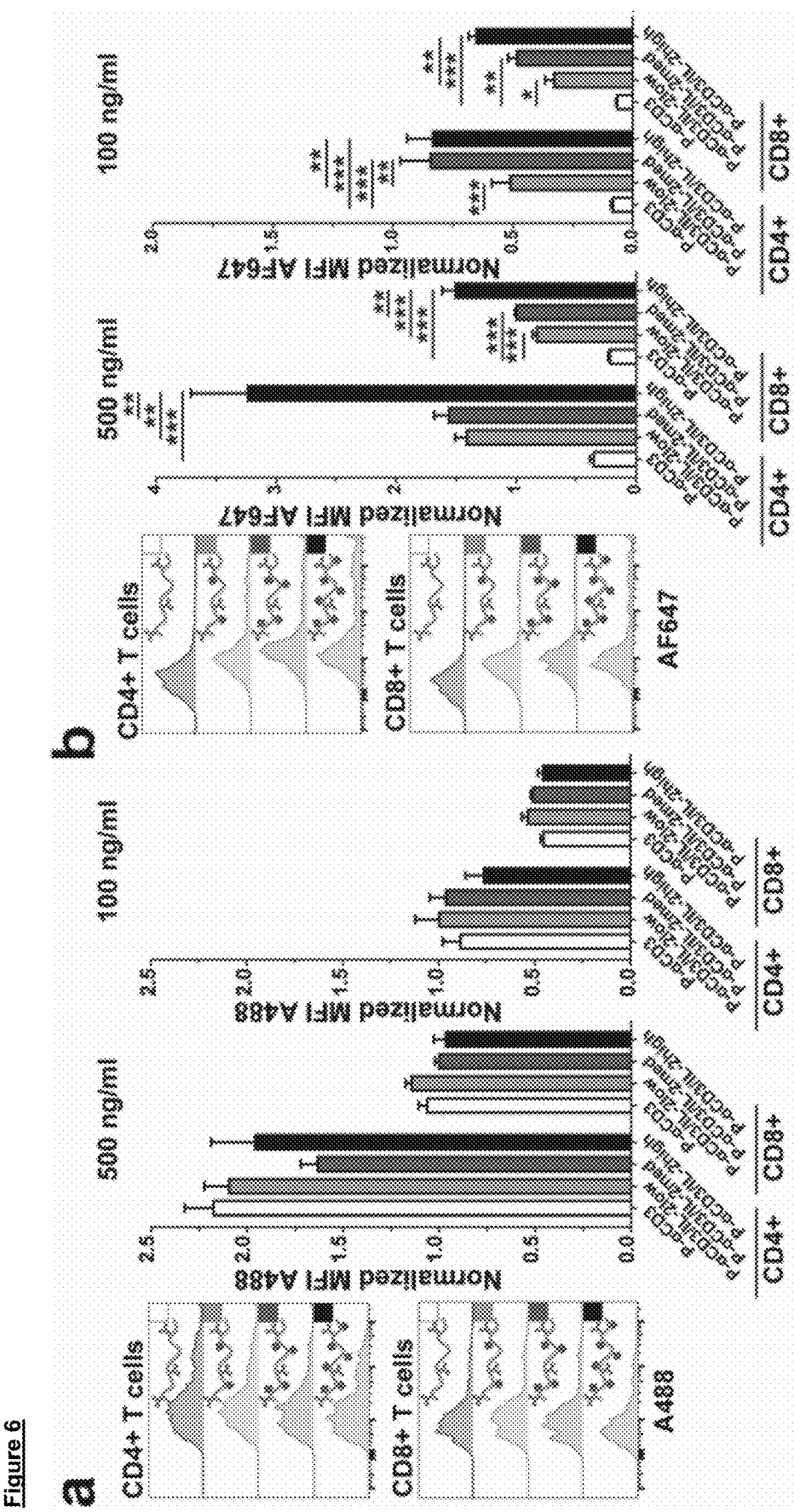
Figure 6:
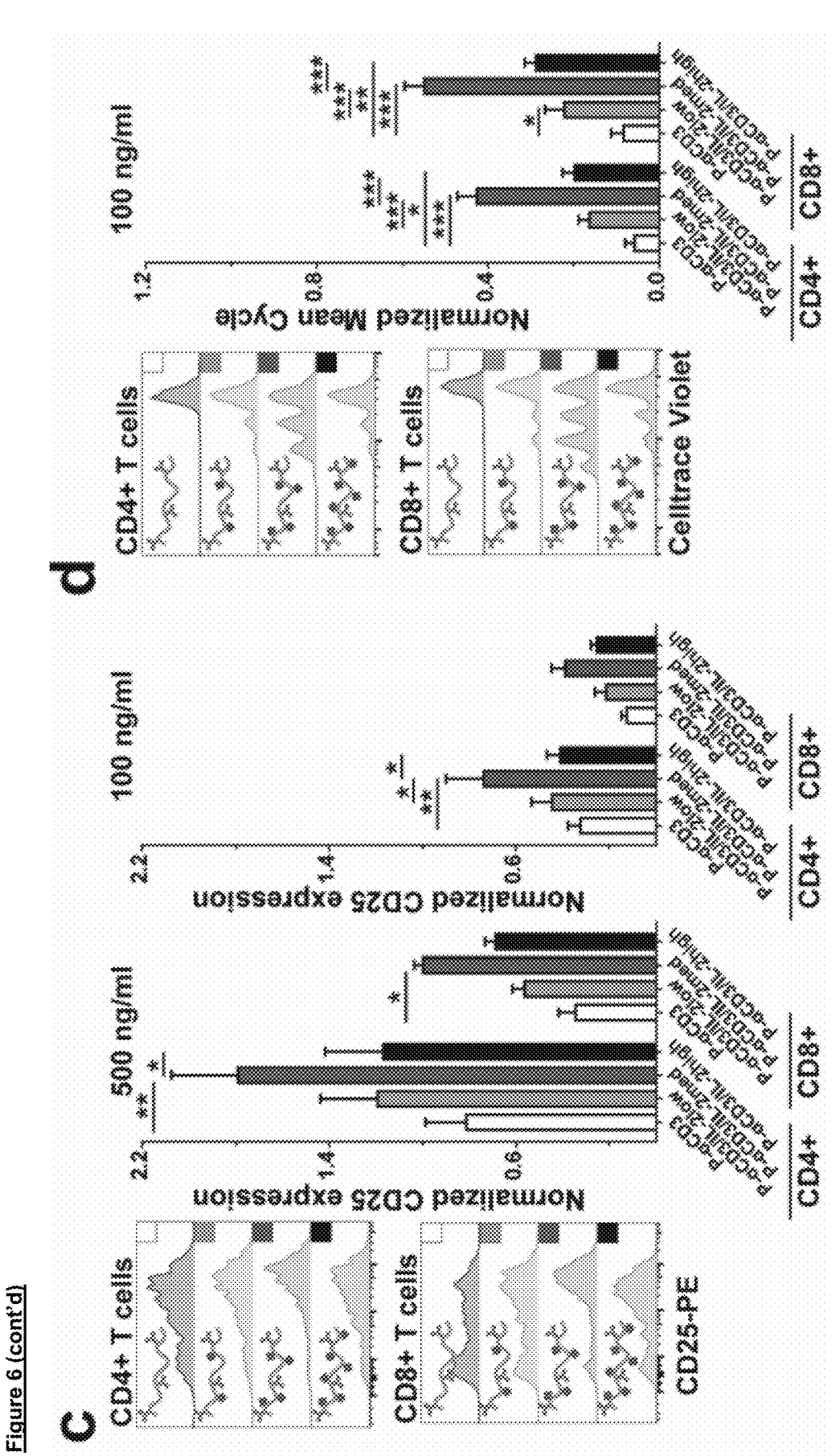

FIG. 6: Biological activity of filamentous semi-flexible IL-2-presenting sDCs. (A) Amount of αCD3 bound to T cells after 16 h of incubation with 500 ng/ml and 100 ng/ml P-αCD3 conjugates, functionalized with different IL-2 densities. Bound αCD3 was determined by flow cytometry analysis of A488 signals (x-axis of histograms). (B) Amount of IL-2 bound to T cells after 16 h of incubation with 500 ng/ml and 100 ng/ml P-αCD3 conjugates, functionalized with different IL-2 densities. Bound IL-2 was determined by flow cytometry analysis of AF647 signals (x-axis of histograms). (C) CD25 expression of T cells after 16 h of incubation with 500 ng/ml and 100 ng/ml P-αCD3 conjugates, functionalized with different IL-2 densities. To determine CD25 expression, the cell surface was stained using an anti-CD25-PE antibody, followed by flow cytometry analysis. (D) Proliferation of T cells after 72 h of stimulation with 100 ng/ml P-αCD3, functionalized with different IL-2 densities. Proliferation was analyzed using flow cytometry analysis, measuring the dilution of Celltrace Violet (x-axis of histograms). The histograms show one representative experiment of duplicate stimulation of T cells from three healthy donors for CD4+ T cells (upper panels) and CD8+ T cells (lower panels). The mean number of cycles was calculated for each experiment. After T cell stimulation, the values were normalized using the stimulation with 500 ng/ml of P-αCD3/1L-2med (CD8+ T cells) as the reference. The normalized values of duplicate stimulations of three donors were pooled to obtain mean and SEM values, as depicted in the bar graphs. *$p<0.05$, $p<0.01$, *$p<0.001$.

Figure 7:
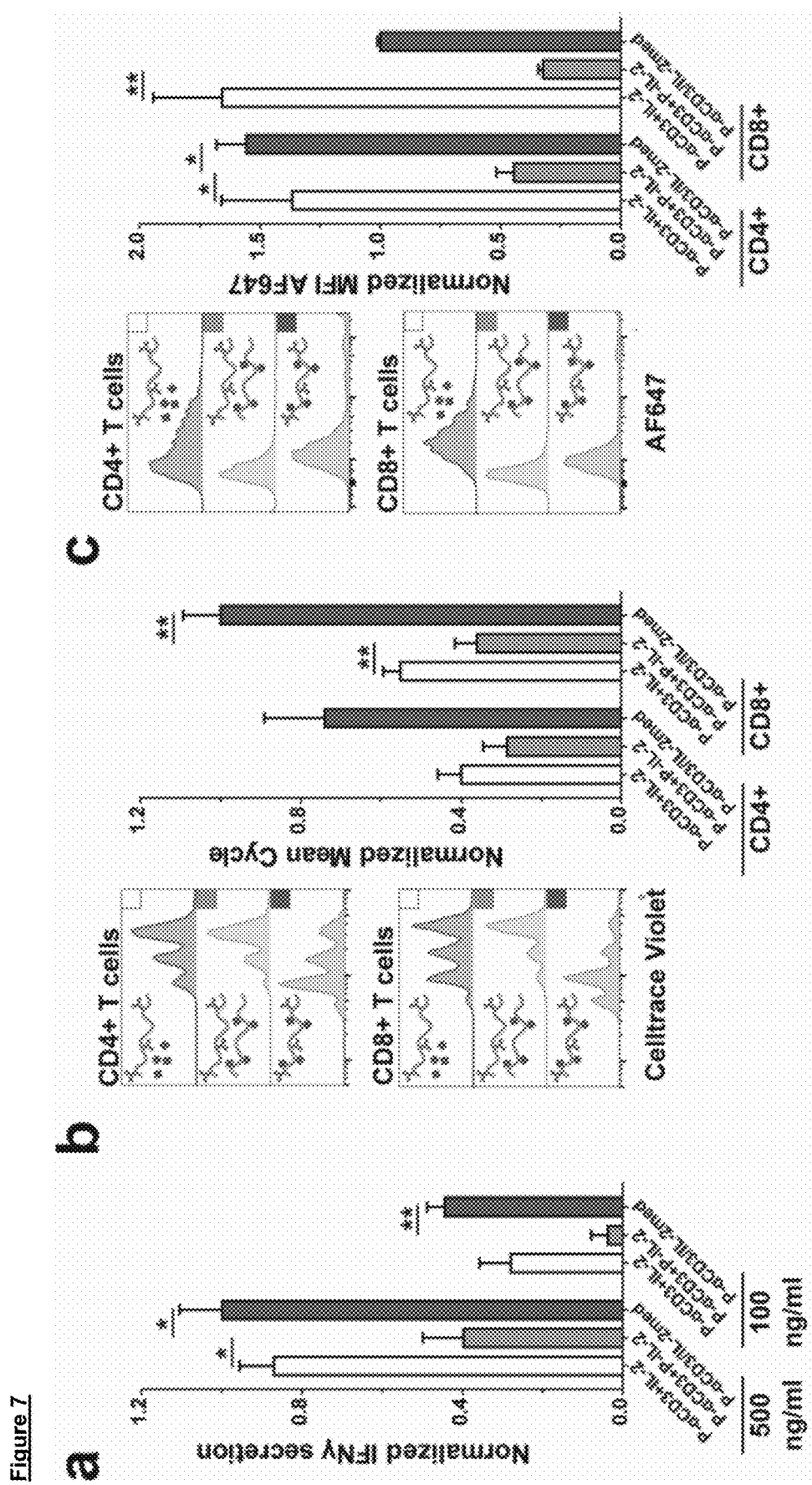

FIG. 7: The role of sDCs in T cell stimulation by cytokines. (A) IFNγ secretion into the supernatant after stimulating T cells with P-αCD3 mixed with unbound IL-2 or P-IL-2, or P-αCD3/IL-2med for 16 h. In each stimulation, the same amount of IL-2 was used. The cells were stimulated using 500 ng/ml or 100 ng/ml αCD3. (B) Proliferation of T cells after 72 h of stimulation with 500 ng/ml P-αCD3 mixed with unbound IL-2 or P-IL-2, or P-αCD3/IL-2med. Proliferation was determined by flow cytometry analysis, measuring the dilution of Celltrace Violet (x-axis of histograms). (C) Amount of IL-2 bound to T cells after 16 h of incubation with 500 ng/ml P-αCD3 mixed with unbound IL-2 or P-IL-2, or P-αCD3/IL-2med. Bound IL-2 was determined by flow cytometry analysis of AF647 signals (x-axis of histograms). For both proliferation and binding analysis, the histograms show one representative experiment of duplicate stimulation of T cells from three healthy donors for CD4+ T cells (upper panel) and CD8+ T cells (lower panel). After T cell stimulation, the values were normalized, using the stimulation with 500 ng/ml of P-αCD3/IL-2med (CD8+ T cells) as the reference. The normalized values of duplicate stimulations of three donors were pooled to obtain mean and SEM values, as depicted in the bar graphs. *p<0.05, p<0.01, *p<0.001.

FIG. 8: The role of sDCs in T cell stimulation by cytokines. (A) TNFα secretion into supernatant after 16 h of T cell stimulation with P-αCD3 mixed with unbound IL-2 or P-IL-2, or P-αCD3/IL-2med. In each stimulation, the same amount of IL-2 was used. The cells were stimulated using 500 ng/ml αCD3 or 100 ng/ml αCD3. (B) Amount of αCD3 bound to T cells after 16 h of incubation with 500 ng/ml and 100 ng/ml P-αCD3 mixed with unbound IL-2 or P-IL-2, or P-αCD3/IL-2med. Bound αCD3 was determined by flow cytometry analysis of A488 signals (x-axis of histograms). (C) Amount of IL-2 bound to T cells after 16 h of incubation with 100 ng/ml P-αCD3 mixed with unbound IL-2 or P-IL-2, or P-αCD3/IL-2med. Bound IL-2 was determined by flow cytometry analysis of AF647 signals (x-axis of histograms). (D) Proliferation of T cells after 72 h of stimulation with 100 ng/ml P-αCD3 mixed with unbound IL-2 or P-IL-2, or P-αCD3/IL-2med determined by flow cytometry analysis, measuring the dilution of Celltrace Violet (x-axis of histograms). The mean number of cycles was calculated for each experiment. (E) CD25 expression of T cells after 16 hours of incubation with 500 ng/ml and 100 ng/ml of P-αCD3 mixed with unbound IL-2 or P-IL-2, or P-αCD3/IL-2med. To determine CD25 expression, the cell surface was stained using an anti-CD25-PE antibody, followed by flow cytometry analysis. (F) Amount of IL-2 bound to non-activated and activated CD4+ T cells and (G) CD8+ T cells after 16 hours of incubation with 500 ng/ml of P-αCD3 mixed with unbound IL-2 or P-IL-2, or P-αCD3/IL-2. To obtain activated CD25+T cells, the cells were stimulated with αCD3/αCD28-functionalized Dynabeads for 24 h. Bound IL-2 was determined by flow cytometry analysis of AF647 signals (x-axis of histograms). The histograms show one representative experiment of duplicate stimulation of T cells from three healthy donors for non-activated (top/white box) and activated (bottom/grey box) T cells. After T cell stimulation, the values were normalized to the stimulation with 500 ng/ml of P-αCD3/IL-2med (non-activated CD8+ T cells). The normalized values of duplicate stimulations of three donors were pooled to obtain mean and SEM values, as depicted in the bar graphs. (H) Dot plot of flow cytometry measurements of αCD3-coated and αCD3/IL-2-coated microbeads to show successful coating with αCD3 and IL-2. Samples used in the T cell stimulation experiments are depicted in green (B-αCD3) and red (B-αCD3/IL-2). (I) Amount of IL-2 bound to HUVECs after 16 h of incubation with 500 ng mL$^{-1}$ P-αCD3 mixed with unbound IL-2 or P-IL-2, or P-αCD3/IL-2med. Bound IL-2 was determined by flow cytometry analysis of AF647 signals (x-axis of histogram). After incubation, the values were normalized, using the binding of P-αCD3/IL-2med as the reference. *p<0.05, p<0.01, *p<0.001.

Figure 9:
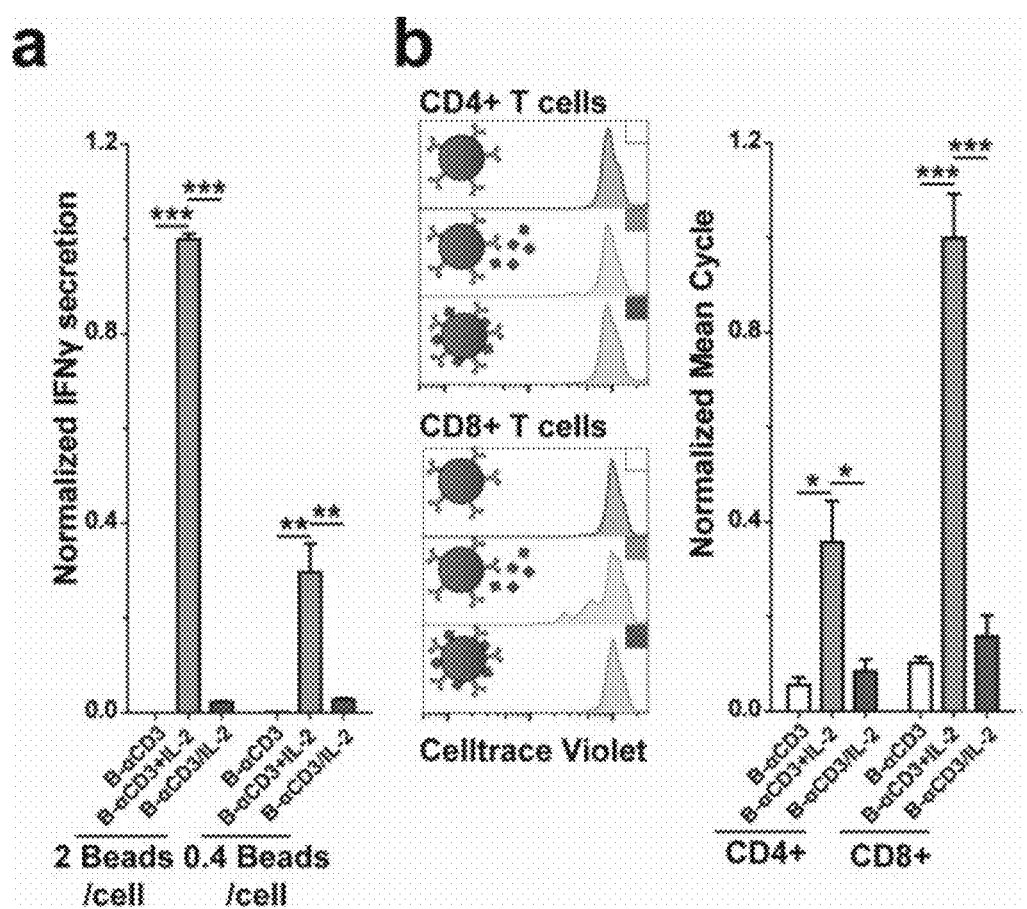

FIG. 9: Low IL-2 activity on αCD3/IL-2-functionalized microbeads. (A) IFNγ secretion into the supernatant after stimulating T cells with B-αCD3, B-αCD3 mixed with unbound IL-2 and B-αCD3/IL-2 for 16 h. Cells were stimulated using 500 ng/ml αCD3 or 100 ng/ml αCD3. (B) Proliferation of T cells after 72 h of stimulation with B-αCD3, B-αCD3 mixed with unbound IL-2 and B-αCD3/IL-2 determined by flow cytometry analysis, measuring the dilution of Celltrace Violet (x-axis of histograms). Histograms show one representative experiment of duplicate stimulation of T cells from three healthy donors for CD4+ T cells (upper panel) and CD8+ T cells (lower panel). After T cell stimulation, the values were normalized, using the stimulation with 500 ng/ml of B-αCD3+IL-2 (CD8+ T cells) as the reference. The normalized values of duplicate stimulations of three donors were pooled to obtain mean and SEM values, as depicted in the bar graphs. *p<0.05, p<0.01, *p<0.001.

FIG. 10: Biological activity of PIC-IFNα conjugates (A) IFNγ secretion of T cells treated with Dynabeads alone, or together with IFNα or DBCO- and dye-functionalized IFNα (D-IFNα). The cells were stimulated using 2 beads/cell and 33 ng/ml IFNα (left) or 0.4 beads/cell with 6.6 ng/ml IFNα (right). (B) Amount of αCD3 bound to T cells after 16 h of incubation with 500 ng/ml and 100 ng/ml P-αCD3, functionalized with different IFNα densities. Bound αCD3 was determined by flow cytometry analysis of A488 signals (x-axis of histograms). (C) Amount of IFNα bound to T cells after 16 h of incubation with 500 ng/ml and 100 ng/ml P-αCD3, functionalized with different IFNα densities. Bound IFNα was determined by flow cytometry analysis of AF647 signals (x-axis of histograms). (D) IL-2 secretion and (E) TNFα secretion into the supernatant after 16 h of stimulation of T cells with P-αCD3, functionalized with different IFNα densities. The cells were stimulated using 500 ng/ml αCD3 or 100 ng/ml αCD3. (F) Proliferation of T cells after 72 h of stimulation with 500 ng/ml P-αCD3, functionalized with different IFNα densities. Proliferation was determined using flow cytometry analysis, measuring the dilution of Celltrace Violet (x-axis of histograms). The mean number of cycles was calculated for each experiment. (G) Proliferation of T cells after 72 h of stimulation with 500 ng/ml P-αCD3 mixed with unbound IFNα or P-IFNα, or P-αCD3/IFNαhigh. Proliferation was determined by flow cytometry analysis, measuring the dilution of Celltrace Violet (x-axis of histograms). The mean number of cycles was calculated for each experiment. The histograms show one representative experiment of duplicate stimulation of T cells from three healthy donors for CD4+ T cells (upper panel) and CD8+ T cells (lower panel). After T cell stimulation, the values were normalized using the value obtained from stimulation with Dynabeads (A) as the reference or, alternatively, the stimulation with 500 ng/ml of P-αCD3/IFNαhigh (CD8+ T cells). The normalized values of duplicate stimulations of three donors were pooled to obtain mean and SEM values, as depicted in the bar graphs. *p<0.05, p<0.01, *p<0.001.

Figure 11:
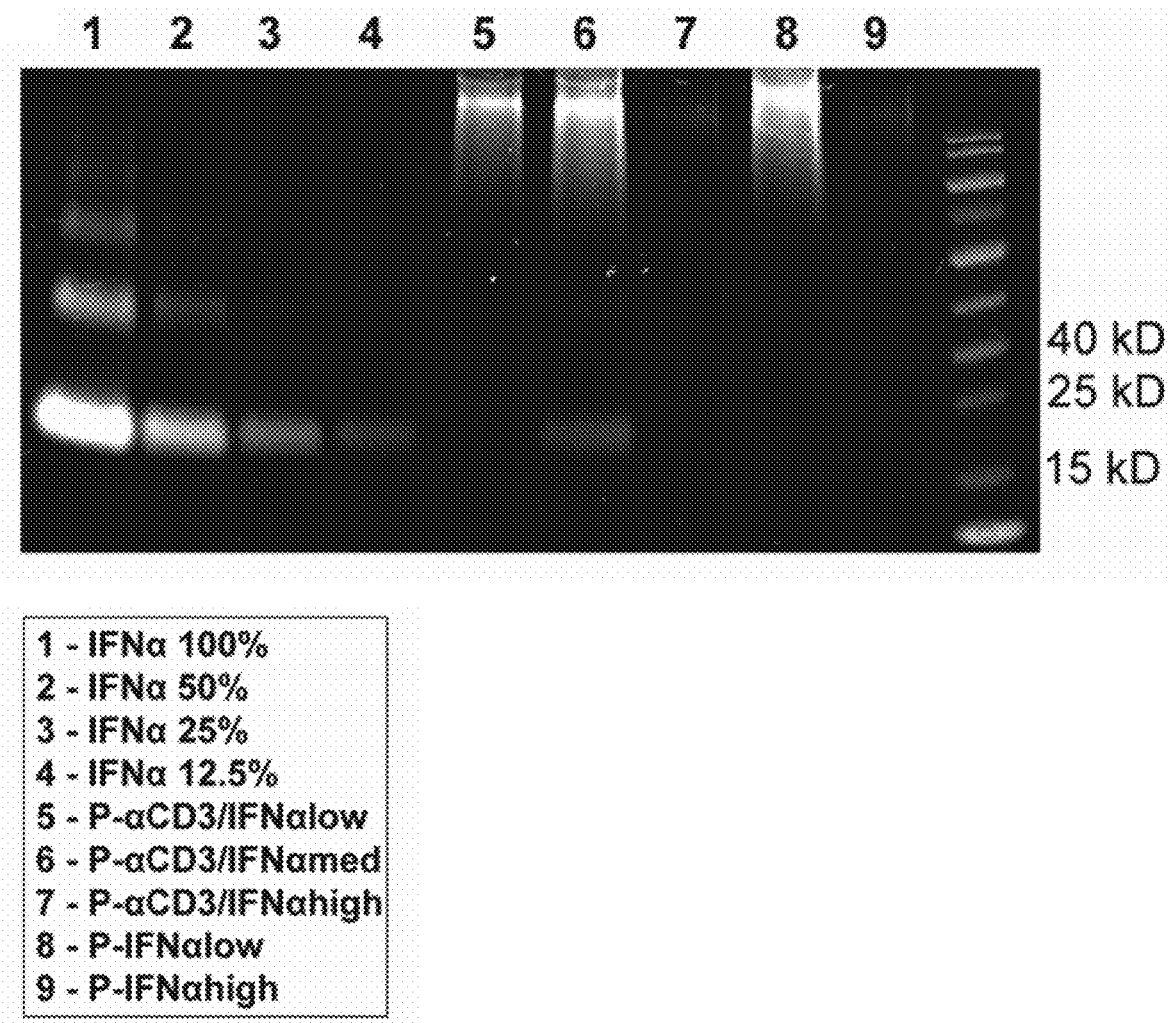

FIG. 11: SDS-PAGE of purified PIC-IFNα conjugates (lanes 5-9). Lanes 1-4 were loaded with an IFNα standard. The amount of IFNα conjugated to the PIC-IFNα samples corresponds to 100% (lane 1).

Figure 12:
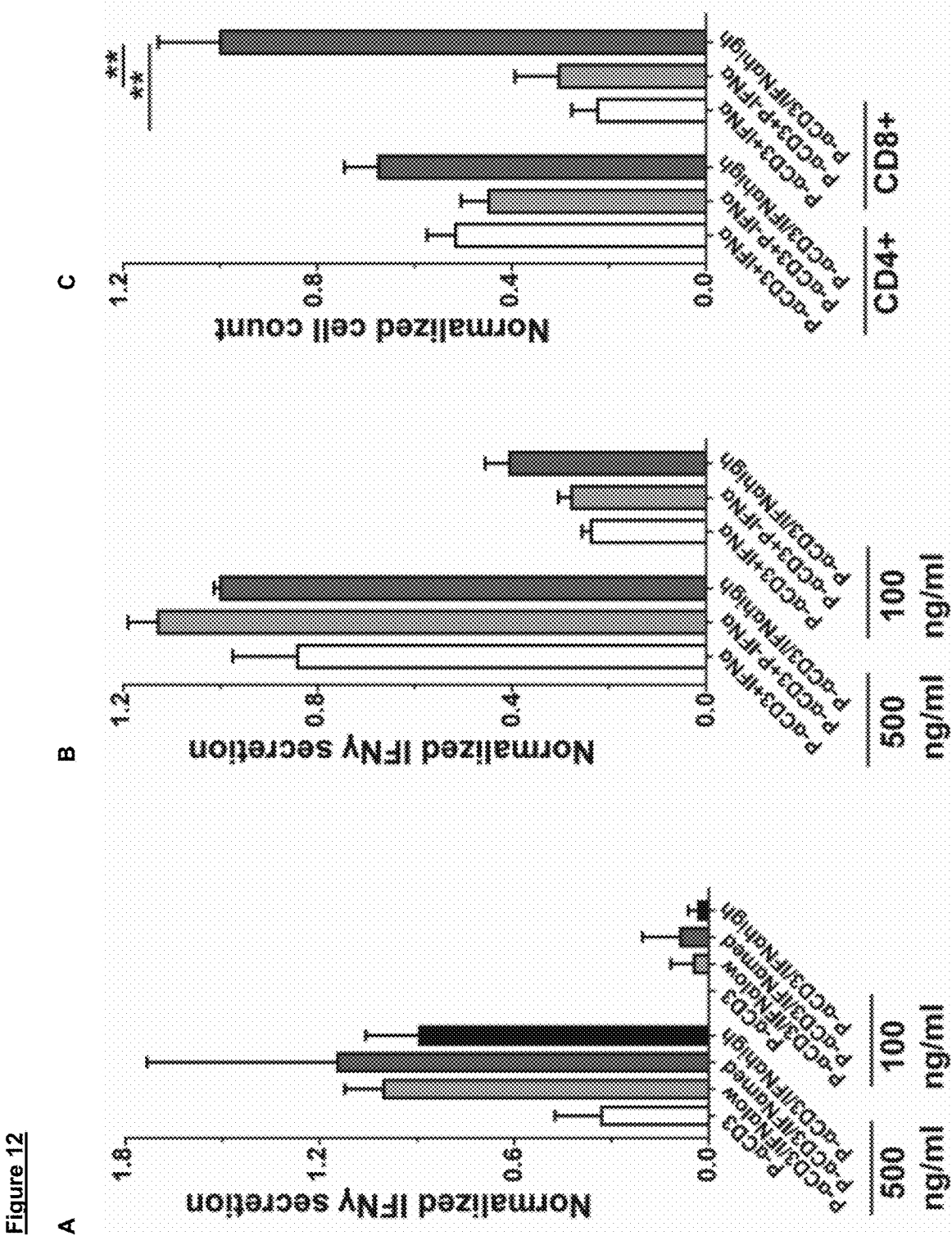

FIG. 12: (A) IFNγ secretion into the supernatant after stimulating T cells with αCD3-functionalized sDCs containing different amounts of IFNα for 16 h. The cells were stimulated using 500 ng/ml αCD3 or 100 ng/ml αCD3. (B) IFNγ secretion into the supernatant after 16 h of T cell stimulation with P-αCD3 mixed with unbound IFNα or P-IFNα, or P-αCD3/IFNαhigh. In each stimulation, the same amount of IFNα was used. The cells were stimulated using 500 ng/ml αCD3 or 100 ng/ml αCD3. (C) Cell counts after 7 days of T cell stimulation with 100 ng/ml P-αCD3, P-αCD3 mixed with unbound IFNα or P-αCD3/IFNαhigh. After T cell stimulation, the values were normalized using the stimulation with P-αCD3/IFNαhigh (CD8+ T cells) as the reference. The normalized values of duplicate stimulations of three donors were pooled to obtain mean and SEM values, as depicted in the bar graphs. *p<0.05, **p<0.01

FIG. 13: Functional consequences of 14-day T cell stimulation with cytokine-PIC conjugates. T cells were stimulated with 500 ng/ml P-αCD3/IL-2, P-αCD3/IFNα and Dynabeads and re-stimulated after 7 days. After 14 days, the cytokine production capacity of these T cells was determined after 6 h PMA+ionomycin stimulation in the presence of Brefeldin A and monensin. Using intracellular staining and flow cytometry analysis, the cytokine expression profiles for IL-2, IFNγ and TNFα were determined for (A) CD4+ T cells and (B) CD8+ T cells. (C-E) Expression of (C) CD107a, (D) Granzyme B and (E) PD-1. T cells stimulated for 14 days were re-stimulated with PMA+ionomycin in the presence of Brefeldin A and monensin. An anti-CD107a-PECy5 antibody was used to determine the expression of the degranulation marker CD107a (C, x-axis of histograms) using flow cytometry analysis. Intracellular staining for Granzyme B and cell surface staining for PD-1 were performed to determine the expression of these molecules. The histograms show one representative experiment of duplicate stimulation of T cells from three healthy donors for CD4+ T cells (upper panel) and CD8+ T cells (lower panel). Pooled mean fluorescence intensities (MFI) SEM are depicted in the bar graph. *p<0.05, **p<0.01.

FIG. 14: Functional consequences of 14-day T cell stimulation with PIC-cytokine conjugates. (A, B) T cells were stimulated with 500 ng/ml P-αCD3 mixed with IL-2, P-αCD3/IL-2, P-αCD3 mixed with IFNα, P-αCD3/IFNα or Dynabeads and re-stimulated after 7 days. After 14 days, the cytokine production capacity of these T cells was determined after 6 h PMA+ionomycin stimulation in the presence of Brefeldin A and monensin, after which intracellular staining and flow cytometry analysis revealed cytokine expression profiles for IL-2, IFNγ and TNFα of (A) CD4+ T cells and (B) CD8+ T cells. (C-E) Expression of (C) CD107a, (D) Granzyme B and (E) PD-1. 14-day-stimulated T cells were re-stimulated with PMA+ionomycin in the presence of Brefeldin A and monensin. An anti-CD107a-PECy5 antibody was used to determine the expression of the degranulation marker CD107a (C, x-axis of histograms) by flow cytometry analysis. Intracellular staining for Granzyme B and cell surface staining for PD-1 were performed to determine the expression of these molecules. The histograms show one representative experiment of duplicate stimulation of T cells from three healthy donors for CD4+ T cells (upper panel) and CD8+ T cells (lower panel). Pooled mean fluorescence intensities (MFI)±SEM are depicted in the bar graphs. *p<0.05, **p<0.01.

Figure 15:
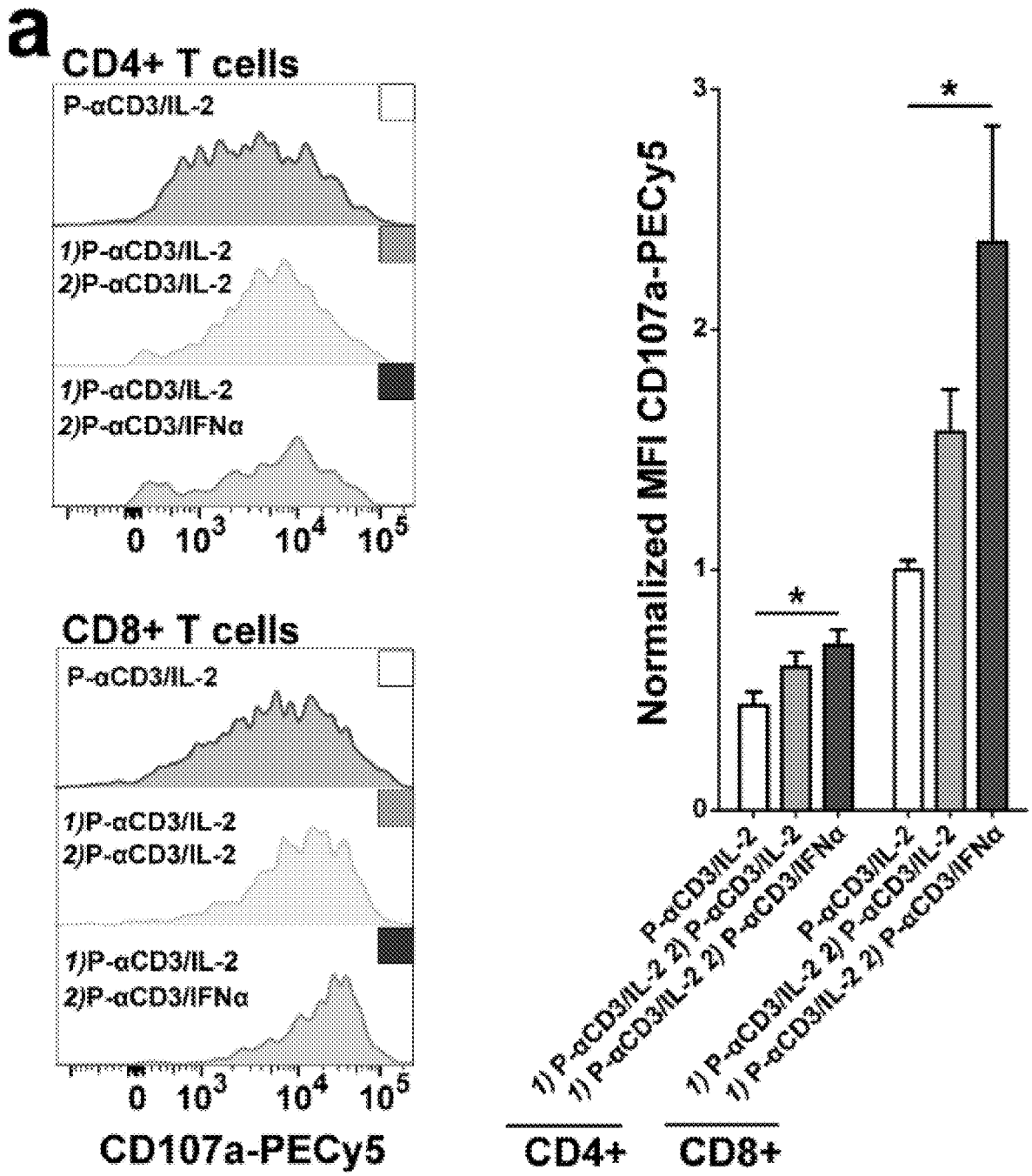
Figure 15:
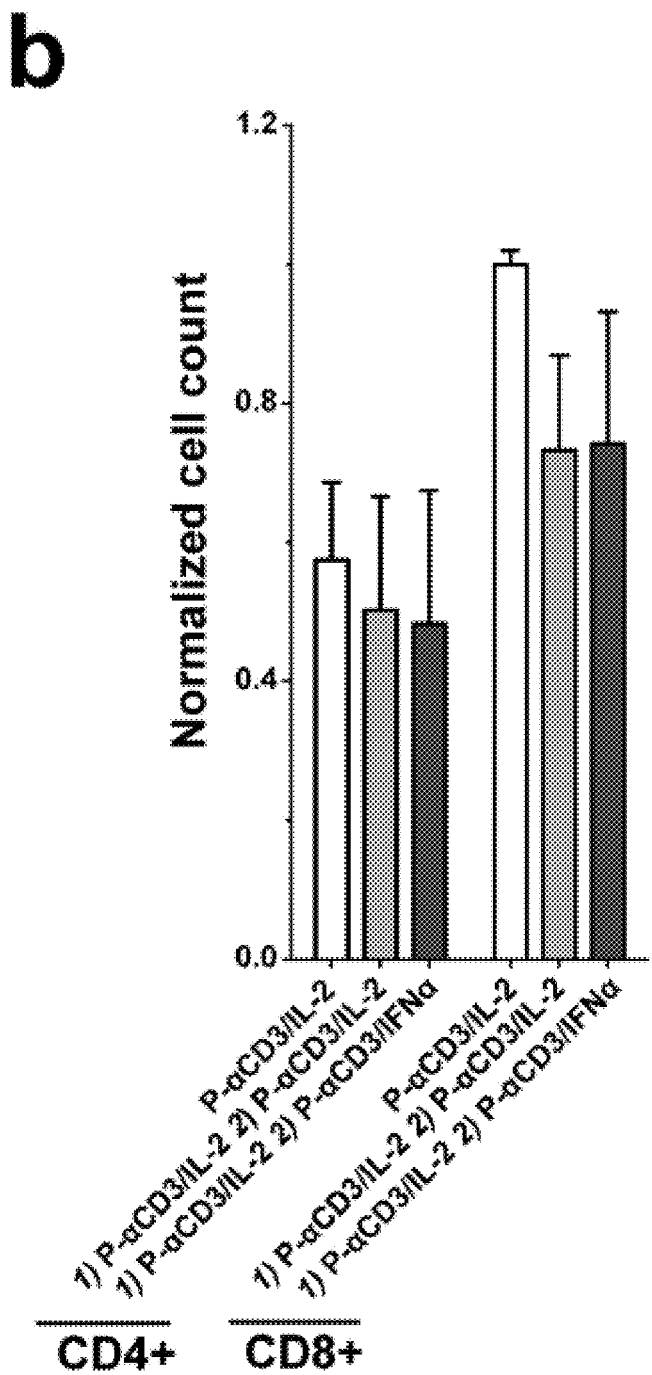
Figure 15:
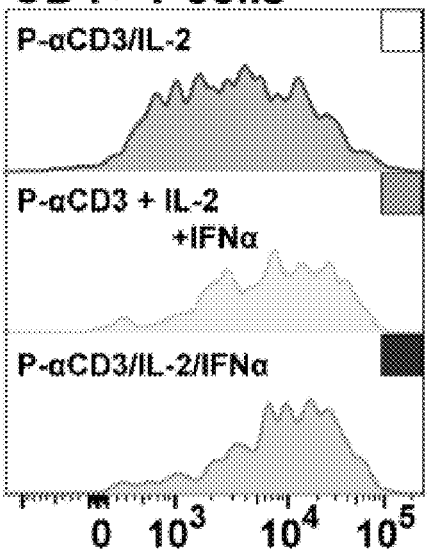
Figure 15:
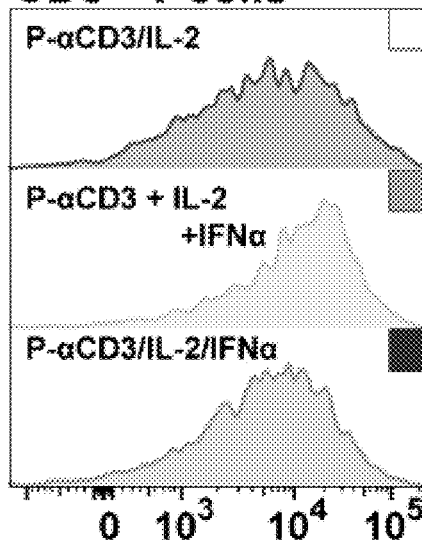
Figure 15:
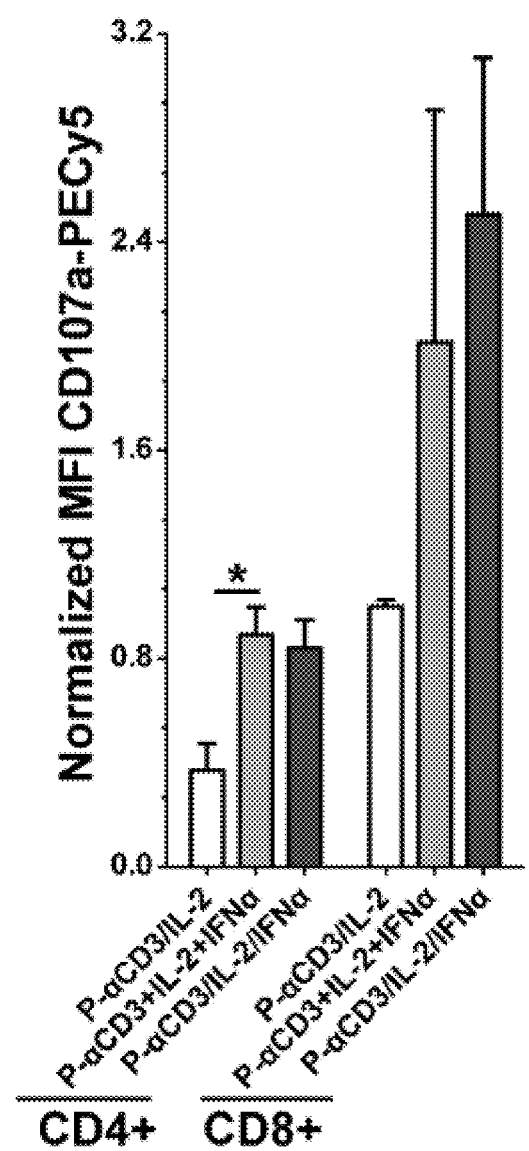
Figure 15:
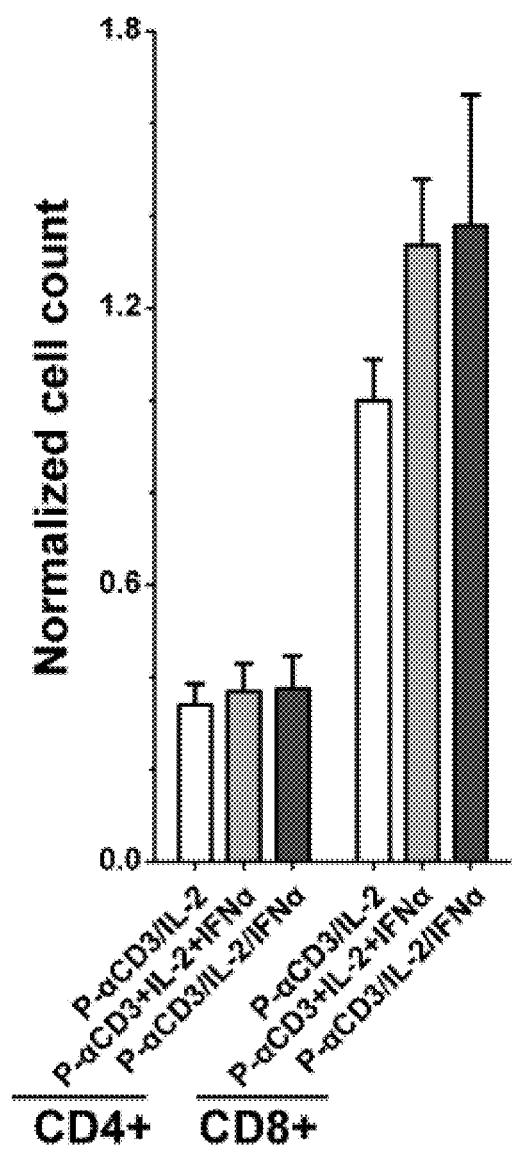

FIG. 15: Expression of degranulation marker CD107a and cell numbers after combined stimulation with PIC-bound IL-2 and IFNα. T cells were 1) stimulated with 500 ng mL$^{-1}$ P-αCD3/IL-2 and 2) re-stimulated with 500 ng mL$^{-1}$ P-αCD3/IL-2 or P-αCD3/IFNα after 3 days. At day 7, cells were a) stimulated with PMA+ionomycin in the presence of Brefeldin A, monensin, and anti-CD107a-PECy5 for 6 h. Using flow cytometry analysis, the expression of CD107a was determined. b) Cell counts after 7 days of T cell stimulation. Similarly, T cells were stimulated with 500 ng mL$^{-1}$ P-αCD3/IL-2, P-αCD3+IL-2+IFNα, and P-αCD3/1L-2/IFNα for 7 days. c) After this, cells were stimulated with PMA+ionomycin in the presence of Brefeldin A, monensin, and anti-CD107a-PECy5 for 6 h. Using flow cytometry analysis, the expression of CD107a was determined. d) Cell counts after 7 days of T cell stimulation with 500 ng mL$^{-1}$ P-αCD3/IL-2, P-αCD3+IL-2+IFNα, and P-αCD3/1L-2/IFNα. The histograms show one representative experiment of duplicate stimulation of T cells from three healthy donors for CD4+ T cells (upper panel) and CD8+ T cells (lower panel). The values were normalized using the stimulation of CD8+ T cells with P-αCD3/IL-2 (without re-stimulation) as a reference. The normalized values of duplicate stimulations of three donors were pooled to obtain mean and SEM values, as depicted in the bar graphs. *p<0.05, **p<0.01.

Figure 16:
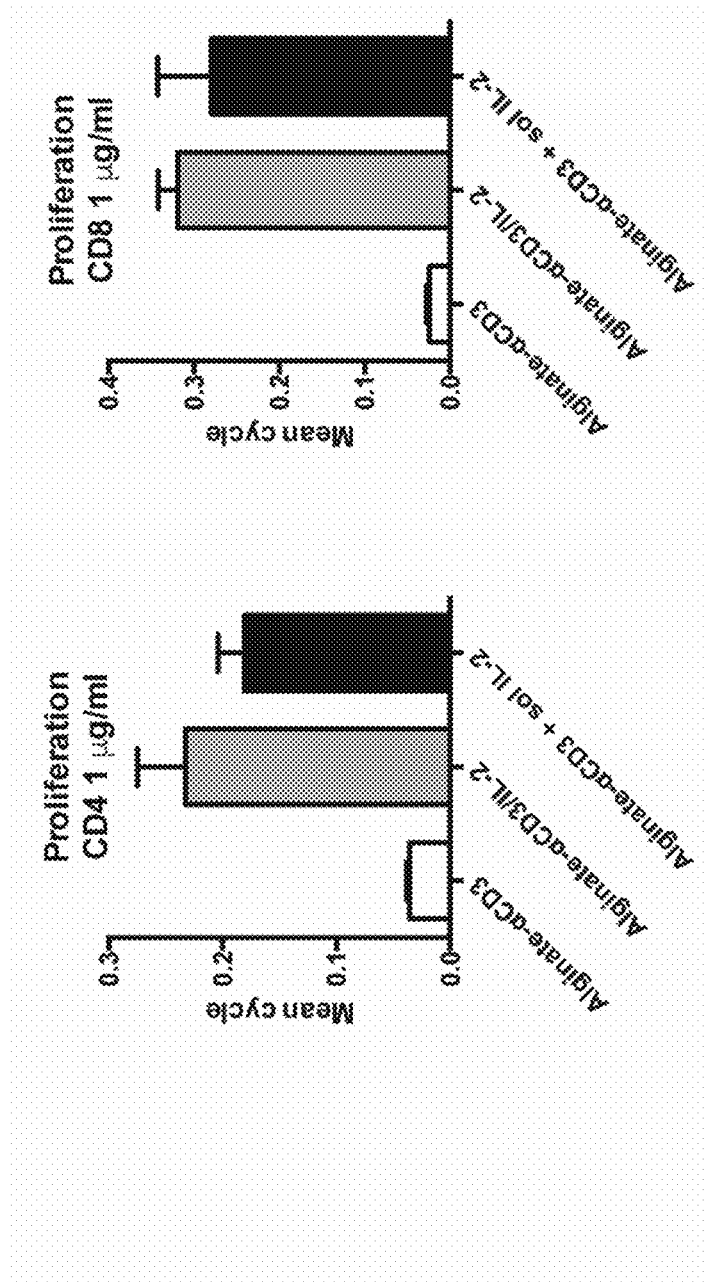

FIG. 16: Stimulation of T-cells with alginate conjugates. Proliferation of CD4 (left) and CD8 (right) T cells after 72 h of stimulation, comparing αCD3 functionalized alginate (white bar) and αCD3 and IL-2 functionalized alginate (grey bar) with αCD3 functionalized alginate where soluble IL-2 was added (black bar). The αCD3 concentration was 1 μg/ml for all treatments. The mean number of cycles was calculated for each experiment. The normalized values of duplicate stimulations of two donors were pooled to obtain mean and SEM values as depicted in the bar graphs.

Figure 17:
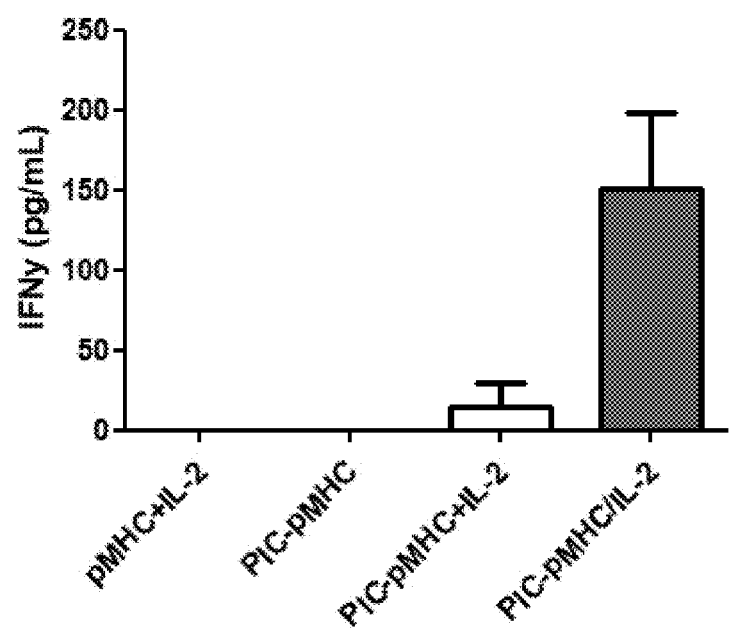

FIG. 17: PIC nanofilaments were functionalised with HLA-A201 MHC presenting the NY-ESO-I peptide (pMHC). T cells from a healthy donor were transfected with mRNA encoding a TCR specific for NY-ESO-I presented in the context of HLA-A201. The NY-ESO-I specific T cells were then contacted with nanofilaments displaying pMHC in the presence and absence of soluble IL-2 (FIG. 17, PIC-pMHC+IL-2, and PIC-pMHC, respectively). NY-ESO-I specific T cells were also contacted with PIC nanofilaments functionalised with both pMHC and IL-2 (FIG. 17, PIC-pMHC/IL-2). Finally, T cells were also contacted with soluble pMHC and soluble IL-2 (FIG. 17, pMHC+IL-2). Supernatant was collected and IFNγ concentration measured by ELISA.

As used herein, a "nanofilament" refers to a filamentous scaffold formed of a polymeric backbone to which molecules such as cytokines and binding molecules can be attached. Such attachment can be direct to the polymeric backbone or indirectly, for example via a linker or sidechain extending from the polymeric backbone, such as a PEG sidechain. "Attached" as used herein is taken to mean the components are chemically bonded (e.g. covalently bonded). Nanofilaments are flexible or semi-flexible structures that are nano-sized—that is, typically have lengths measurable on a nanoscale of from 1 to 1000 nm.

As used herein, a polyisocyanopeptide (PIC) nanofilament refers to a nanofilament with a PIC polymer backbone formed from polymerised isocyanopeptide monomers, to which molecules of a cytokine or a binding molecule can be attached. Such attachment can be direct to the PIC backbone or indirectly, for example via a linker or sidechain, such as a PEG sidechain, extending from the polymer backbone and separating the backbone monomers from the attached molecules. "Attached" as used herein is taken to mean the components are chemically bonded (e.g. covalently bonded).

As used herein, "binding molecule" refers to molecules capable of binding to another molecule or complex. Accordingly, a binding molecule can be an antibody or binding-fragment thereof (e.g. a Fab fragment or scFv fragment), an aptamer, a ligand or a receptor, or a complex such as an MHC-antigen complex capable of binding to a T cell receptor (TCR).

As used herein, an "immune cell" is a cell associated with the immune system, for example a T cell (e.g. a CD4+ or CD8+ T cell), B cell, dendritic cell, NK cell, NKT cell, macrophage or monocyte. Other examples will be familiar to the skilled person.

As used herein, a molecule "presented" by an immune cell is a molecule that is present on the cell surface of said immune cell, such that the molecule is capable of being bound by a binding molecule. Molecules that may be presented by an immune cell include CD3, the TCR, the B cell receptor (BCR), CD25, CD28, CD40, CD4OL, CTLA4, CD27, PD1. Other examples will be familiar to the skilled person.

As used herein, a "pharmaceutical composition" refers to a composition suitable for administration to a human subject. Such a composition can comprise one or more nanofilaments in a suitable carrier, for example in suspension in a pharmaceutical diluent. Such compositions can be administered to a subject to modulate immune cell function in vivo, for example to stimulate a subject's immune response.

Provided herein is a nanofilament comprising a plurality of molecules of a first cytokine attached to a polymeric backbone. Further provided are compositions comprising one or more nanofilaments provided herein.

As demonstrated herein, nanofilaments provided herein are particularly effective at presenting cytokines to immune cells in order to modulate the activity of those immune cells. Presentation of cytokines to immune cells by the nanofilaments will be effective because the flexibility of such nanofilaments allows for a variety of interactions between the nanofilament and the immune cells—for example, multivalent interactions in which multiple cytokine molecules bind receptors on the immune cell, thereby potentiating the response; or cross-linking of cytokine receptors on different cells, thereby potentiating the response across a population of cells.

The provided nanofilaments are particularly advantageous when a cytokine and a binding molecule are attached to a single nanofilament. Use of a binding molecule allows the nanofilament to be targeted to a particular cell type or subset, for example T cells, thereby reducing off-target effects. Furthermore, the dynamic range of the nanofilament allows the cytokine molecules and binding molecules to co-localise relative to the targeted immune cell. Such co-localisation is particularly useful when, for example, activating T cells which can require multiple activation signals (for example when the cytokine is IL-2 and the binding molecule an anti-CD3 antibody or MHC-antigen complex).

Therefore, in certain embodiments, the nanofilament further comprises a plurality of molecules of a binding molecule attached to the polymeric backbone. In certain such embodiments, the binding molecule is selected to target a particular immune cell type or subset, for example T cells, B cells or NK cells. Examples of suitable binding molecules are described elsewhere herein.

As demonstrated herein, the provided nanofilaments can effectively modulate immune cell activity. The ability to modulate (e.g. activate, inhibit, tolerise) immune cells has potential applications in both therapy (for example to potentiate a subject's immune response to a condition or disease, to suppress an autoimmune response, or to modulate a cell population for immunotherapy) and in a laboratory setting (for example to activate a cell population in culture).

Therefore, in further aspects, the invention provides nanofilaments or compositions provided herein for use in therapy, for in vitro or ex vivo use to modulate the activity of a population of immune cells.

Described below are a series of embodiments of the present invention. It is intended that any embodiment may be combined with any combination of described embodiments, especially when embodiments are described as preferred, unless such combination is technically incompatible.

Nanofilament

Provided herein are nanofilaments comprising a plurality of molecules of a first cytokine attached to a polymeric backbone. Nanofilaments are semi-flexible filamentous structures that are nano-sized—that is, typically have lengths measurable on a nanoscale of from 1 to 1000 nm, preferably 25 to 1000 nm.

A particular advantage of the nanofilaments is the dynamic range allowing them to present the attached cytokines in such a way that the nanofilament can react to the arrangement of receptors on the cell surface. This is a notable difference to microbead scaffolds presenting cytokines, where the rigid bead surface means the spacing between cytokine molecules is fixed.

Suitable polymers and co-polymers for the polymeric backbone are water soluble and would be familiar to the skilled person. Examples include N-(2-hydroxypropyl) methacrylamide (HPMA), polyether, polyacetal, polyester or polyamide polymers. Further examples include filamentous polysaccharide biopolymers such as alginate, pectin, chitin, guar, carrageenan, carboxymethylcellulose, and hyaluronic acid. Further examples include filamentous protein biopolymers such as collagen, actin and fibrin polymers.

As already described, nanofilaments according to the invention are semi-flexible and the polymer for backbone is a semi-flexible polymer. The skilled person is familiar with polymers which are semiflexibile.

In certain embodiments, the polymeric backbone is formed of a polymer having a persistence length of from 1% to 20% of contour length, preferably of from 2% to 15% of contour length. In certain preferred embodiments, the polymeric backbone is formed of a polymer having a persistence length of from 5% to 15% of contour length, preferably from 8% to 12%, most preferably about 10%.

In certain preferred embodiments, the polymeric backbone is formed of a polymer having a persistence length in the range of from 1 order of magnitude lower than the contour length to the same order of magnitude of the contour length.

Nanofilaments having a persistence length in these ranges are especially capable of dynamic rearrangement without coiling into a polymer ball. The values described refer to persistence length in water, and means for determining the persistence length would be familiar to the skilled person.

The nanofilaments provided herein are particularly effective at modulating immune cell activity because their length allows for presentation of the attached molecules at scales similar to that of the receptor spacing on the cells.

Accordingly, in certain embodiments, the backbone of the nanofilament is less than 1 micrometre in length. In certain embodiments, the backbone has a length in the range of from 1 nm to 1000 nm. In certain embodiments, the backbone has a length in the range of from about 5 nm to about 800nm, In preferred embodiments the backbone has a length of from about 50 nm to about 800 nm, about 100 nm to about 700 nm, for example from about 200 nm to 600 nm, for example about 400 nm to about 600 nm, e.g. about 400 nm or about 500 nm.

It will be appreciated by the skilled person that, when synthesising a polymer or co-polymer, a statistical distribution of nanofilament lengths is obtained. Therefore, where, say, a composition includes a large number of nanofilaments, the embodiments of length described above refers to the statistical length of the polymer nanofilament sample, for example the mean length of polymer nanofilament.

Polyisocyanopeptide (PIC) polymer backbones are particularly preferred and effective for use in the provided nanofilaments. They have a worm-like (i.e. filamentous) structure arising from their helical form and do not form a random coil when in an aqueous medium. This worm-like structure allows effective presentation of the attached cytokine molecules to immune cells, thereby modulating the immune activity of the immune cells.

Suitable PIC polymer nanofilaments may be synthesised according to methods known in the art by polymerisation of isocyanopeptide monomers (see for example Mandal, S et al. Therapeutic Nanoworms: Towards Novel Synthetic Dendritic Cells for Immunotherapy. Chem. Sci. 2013, 4, 4168; and Koepf et al, European Polymer Journal, 49 (6), 2013 p. 1510-1522, each of which are incorporated herein by reference).

In certain embodiments, the PIC polymer backbone can be prepared from isocyanide monomers that have been derived from amino acids or peptides. Techniques for converting amino acids into isocyanopeptides suitable for use as monomers in the PIC polymers are known in the art.

When an isocyanopeptide monomer is derived from an amino acid, it may be derived from any suitable naturally-occurring or non-naturally-occurring amino acid, and may for example be a D- or L-amino acid (or may have an R-confirmation or an S-confirmation, referring to the chiral alpha carbon). Selection of a suitable isomer would be familiar to the skilled person and may be determined, for example, by the intended "handedness" of the PIC polymer, which is helical in structure.

In certain embodiments, the PIC polymer backbone is formed by polymerisation of a non-functional monomer and functional monomer. In this context, a functional monomer is a monomer having a functional moiety suitable for use in an attachment reaction, such as a click reaction. Cytokine molecules (and optionally binding molecules) can then be attached as a result of an attachment reaction with the functional moiety. Suitable functional moieties will be familiar to the skilled person and include those commonly used in so-called click chemistry, such as those described in the Examples below.

Accordingly, in certain embodiments the functionalised monomer is functionalised with a suitable functional moiety, for example azide, N-hydroxysuccinimide (NHS), vinyl sulfone, acetylene, $NH_2$, COOH, maleimide, tetrazine, thiol or transcyclooctene (TCO). In certain preferred embodiments, the functionalised monomer is functionalised with an azide moiety. The non-functional monomer is not functionalised with such a group. In certain preferred embodiments, the polymer backbone is obtainable by polymerisation of a methoxy-terminated non-functional monomer and an azide-terminated functional monomer. (For simplicity, a backbone formed by this method is referred to as a polymer or polymeric, rather than co-polymer, despite being formed of functional and non-functional monomers).

In certain embodiments, the ratio of functionalised to non-functionalised monomer is selected such that the reaction produces polymers having a functional group (for example an azide group) every 1-10 nm, preferably every 2-5 nm. In certain embodiments the ratio is chosen to produce a polymer having a functional group (preferably an azide group) every 3.5 nm. It will be appreciated by the skilled person that such polymerisation reactions are random and therefore the described separation of functional groups refers to the statistical or mean separation distance across the synthesised polymer sample, and allows for individually selected functional groups within a polymer nanofilament to be positioned at greater or smaller distances without the polymer nanofilament falling outside the limits of the feature.

In certain such embodiments, the ratio of non-functional monomer (y) to functional monomer (x) is in the range of from 100:1 to 10:1, optionally 50:1 to 10:1. In preferred embodiments, the ratio of y:x is 30:1. The number of monomer units "n" in the polymer nanofilament is determined by the length of the polymer nanofilaments in accordance with the embodiments described herein.

In certain embodiments, "n" is in the range of from 1000 to 20000. In certain preferred embodiments, "n" is in the range of from 1000 to 10,000. In certain preferred embodiments, "n" is in the range of from 2000 to 10,000. In certain preferred embodiments, "n" is in the range of from 3000 to 5000, for example about 4000.

As discussed elsewhere herein, in certain preferred embodiments, the PIC polymer backbone produced according to this polymerisation scheme has a mean length of about 400 nm.

In certain preferred embodiments, the PIC polymer backbone of the nanofilament is obtainable by a method comprising nickel-catalysed polymerization of methoxy-terminated and azide-terminated isocyanopeptide monomers.

In preferred embodiments, the PIC polymer backbone is obtainable by a process comprising the following polymerisation reaction scheme, where "x", "y" and "n" are as defined above:

Scheme A

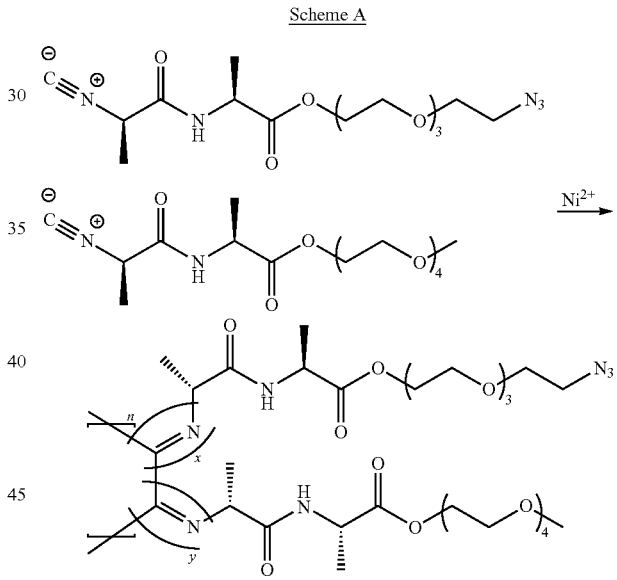

PIC polymers obtainable by a method comprising nickel-catalysed polymerization of methoxy-terminated and azide-terminated isocyanopeptide monomers such as Scheme A are particularly advantageous. Said nanofilaments exhibit a degree of semi-flexibility that is particularly effective at permitting the dynamic range and rearrangement important for optimal immune cell engagement.

In certain embodiments where the polymer is obtainable by a process according to Scheme A, the process can further comprise converting a proportion of the functional groups to an alternative functional group, for example biotin or streptavidin. The proportion converted is determined by the density of immune factors it is intended to attach to the nanofilament. In certain embodiments the proportion converted is from 25 to 75%. In certain embodiments, the PIC backbone is obtainable by a process further comprising converting approximately 50% of the azide groups to biotin.

Conversion of functional groups to biotin in such embodiments is particularly advantageous because it allows effective isolation and purification of the polymers. A preferred example of this purification technique is provided in Hammink et al Bioconjug Chem. 2017 Oct. 18;28(10):2560-2568, which is incorporated herein by reference for this purpose.

Suitable method for preparation of PIC polymer backbones are also described in WO2011007012, which is incorporated herein by reference for this purpose.

In alternative preferred embodiments, the polymer backbone is a polysaccharide polymer, for example an alginate, pectin, chitin, guar, carrageenan, carboxymethylcellulose or hyaluronic acid polymer. In certain preferred embodiments, the polymer backbone is an alginate backbone.

Embodiments described above, for example those regarding the length of the nanofilament and the persistence length of the polymer backbone, apply also to nanofilaments comprising a polysaccharide polymer backbone, for example an alginate polymer backbone.

Cytokine

Cytokines are soluble immune proteins important for signalling to and between cells of the immune system, and include interleukins, chemokines, interferons and TNF-family molecules. Nanofilaments provided herein comprise a plurality of molecules of a cytokine attached to a polymeric backbone. In such embodiments, the cytokine molecules are molecules of the same cytokine—that is, the nanofilament comprises multiple (2 or more) molecules of the one cytokine. Having multiple molecules of the cytokine attached is particularly beneficial as it takes advantage of the semi-flexible nature of the backbone. The semi-flexible nature allows interaction of multiple cytokine molecules with a particular immune cell, thereby increasing immune modulatory effects.

This is in contrast to rigid scaffolds such as microbeads, where steric rigidity prevents multiple contact points being formed with immune cells.

In certain embodiments, the cytokine attached to the backbone is a pro-inflammatory cytokine, such as IL-2, IL-12, IL-7, IL-15, IL-17, IL-6, IL-1, IFNα, IFNγ, TNF (such as TNFα), CXCL8, CCL2, CCL3, CCL4, CCL5, CCL11, CXCL10, CCL19, CCL20, CCL21, and GM-CSF. In certain embodiments, the cytokine is selected from IL-2, IL-7, IL-12, and IFNα. In certain preferred embodiments, the cytokine is IL-2 or IFNα.

In certain alternative embodiments, the cytokine attached to the backbone is an anti-inflammatory cytokine. In certain such embodiments, the cytokine is selected from IL-4, TGFβ, IL-13 and IL-10.

As demonstrated herein, the provided nanofilaments are particularly effective when the cytokine molecules are present at certain densities. Therefore, in certain embodiments, the cytokine is attached to the backbone at a density of at least one molecule about each 400 nm. In certain embodiments, the cytokine is attached to the backbone at a density of at least one molecule about each 190 nm—that is, two cytokine molecules attached to a backbone are separated by no more than about 190 nm.

In certain embodiments, the cytokine is attached to the backbone at a density in the range of from one molecule about each 400 nm to one molecule about each 20 nm. In certain embodiments the cytokine is attached to the backbone at a density in the range of from one molecule about each 190 nm to one molecule about each 40 nm. In certain preferred embodiments, the cytokine molecules are attached at a density of one molecule about each 190 nm, about each 130 nm, about each 90 nm or about each 40 nm. In a preferred embodiment, the cytokine molecules are attached at a density of one molecule about each 40 nm. In a preferred embodiment, the cytokine molecules are attached at a density of one molecule about each 90 nm. In a preferred embodiment, the cytokine molecules are attached at a density of one molecule about each 130 nm. In a preferred embodiment, the cytokine molecules are attached at a density of one molecule about each 190 nm.

In certain embodiments, the nanofilament has from 2-40 molecules of the cytokine attached to the backbone. In certain embodiments, the nanofilament has from 2-20 molecules of the cytokine attached to the backbone. In certain preferred embodiments the nanofilament has from 2-10 molecules of the cytokine attached to the backbone. In certain embodiments, the nanofilament has 2, 3, 4, 5, 6, 7, 8, 9 or 10 molecules of the cytokine attached to the backbone. In certain embodiments, the nanofilament has 2, 4, 8 or 10 molecules of the cytokine attached to the backbone. In certain preferred embodiments, the nanofilament has 4 molecules of the cytokine attached to the backbone.

It will be appreciated by the skilled person that polymerisation is a random process, as is the attachment of cytokine molecules to the polymer backbone. Therefore, when many nanofilaments are being produced, the above-described densities and number of molecules refer to the mean density or number of the molecules and do not exclude the possibility of two individual cytokine molecules falling outside the stated density or a particular nanofilament having a number of molecules attached that is outside the stated amount.

As described elsewhere herein, attachment of the cytokine molecules to the polymeric backbone can be achieved through reaction with monomer units functionalised with functional moieties. The density of cytokine molecules can be varied by modifying the quantity of cytokine present in this reaction relative to the quantity of functional moiety.

In certain alternative embodiments, the density of the cytokine molecule can be varied by varying the ratio of functionalised to non-functionalised monomers during polymerisation, thereby varying the subsequent density of attachment of cytokine molecules. In certain such embodiments, this density can be further modified by the frequency of conversion of functionalised monomers, for example conversion to moieties such as biotin or streptavidin.

Nanofilaments comprising a second cytokine are particularly advantageous since the second cytokine can induce cellular responses that complement and/or enhance the cellular response induced by the first cytokine. For instance, in embodiments wherein the first and second cytokine are both pro-inflammatory cytokines, the first cytokine of the nanofilament may promote T cell proliferation and cellular cytokine production, and the second cytokine may promote cytotoxic activity. A demonstration of the combined effect of having a first and a second cytokine on the nanofilament is provided in the Examples herein.

Therefore, in certain embodiments, molecules of a second cytokine may be attached to the nanofilament. For example, in such embodiments, the nanofilament may comprise a plurality of molecules of a first cytokine (e.g. IL-2 or IFNα) and may comprise a plurality of molecules of a second cytokine.

The second cytokine may be selected from those identified above in relation to the first cytokine.

In certain such embodiments, the first cytokine is a pro-inflammatory cytokine and the second cytokine may be a different pro-inflammatory cytokine. Suitable pro-inflammatory cytokines include IL-2, IL-12, IL-7, IL-17, IL-6, IL-1, IFNα, IFNγ, TNF (such as TNFα), CXCL8, CCL2, CCL3, CCL4, CCL5, CCL11, CXCL10, CCL19, CCL20, CCL21, and GM-CSF.

In certain preferred embodiments the first and second cytokine are IFNα and IL-2, respectively.

In certain embodiments wherein molecules of a first cytokine and molecules of a second cytokine are attached to the nanofilament, preferably the density of total cytokine molecules (i.e. molecules of the first and second cytokines) attached to the backbone is in the range of from one molecule about each 400 nm to one molecule about each 20 nm. In certain embodiments the total cytokine molecules are attached to the backbone at a density in the range of from one molecule about each 200 nm to one molecule about each 100 nm. In certain preferred embodiments, the total cytokine molecules are attached at a density of one molecule about each 140 nm.

In certain embodiments wherein molecules of a first cytokine and molecules of a second cytokine are attached to the nanofilament, preferably the molecules of the first and the second cytokine are attached to the backbone at a density independently selected in the range of from one molecule about each 400 nm to one molecule about each 20 nm. In certain embodiments the density of each cytokine is independently in the range of from one molecule about each 400 nm to one molecule about each 200 nm. In certain preferred embodiments, the first cytokine molecules are attached at a density of one molecule about each 200 nm, about each 230 nm, about each 250 nm, about each 270 nm, about each 300 nm, about each 350 nm, or about each 400 nm. In certain preferred embodiments, the second cytokine molecules are attached at a density of one molecule about each 200 nm, about each 230 nm, about each 250 nm, about each 270 nm, about each 300 nm, about each 350 nm, or about each 400 nm.

In certain preferred embodiments, the first and second cytokine are attached to the nanofilament ata ratio in the range of about 1:2 to about 2:1. In certain preferred embodiments, the first and second cytokine are attached to the nanofilament at a ratio of about 2:3.

In alternative embodiments, the densities and numbers of molecules attached to the backbone described above in relation to the first cytokine apply equally and independently to the second cytokine.

Binding Molecule

It is demonstrated herein that the provided nanofilaments are particularly effective at modulating the activity of a subset of immune cell (for example stimulating T cells) when they also have a binding molecule attached that targets the selected immune cell. Without being bound by theory, it is hypothesised that this is due to selective localisation of the nanofilament to the targeted immune cell, making it more likely that it will be brought into contact with the attached cytokine.

Therefore, in certain embodiments, the provided nanofilaments further comprise a plurality of molecules of a binding molecule attached to the polymeric backbone, wherein the binding molecule binds to a molecule presented by an immune cell.

Suitable binding molecules include those capable of binding to a receptor, molecule or complex presented by an immune cell. Accordingly, in certain embodiments the binding molecule is selected from an antibody or binding-fragment thereof (e.g. a Fab fragment or scFv fragment), an aptamer (including protein and nucleotide aptamers), a ligand or a receptor, a protein complex (for example an MHC-antigen complex capable of binding to a TCR heterodimer), carbohydrate ligands, and other suitable binding molecules familiar to the skilled person.

In certain preferred embodiments, the binding molecule is an antibody or binding fragment thereof. Binding fragments of antibodies are known to the skilled person and include Fab, $F(ab')_2$, scFv, VH or VL domains, diabodies and monovalent IgG molecules. In certain preferred embodiments the binding molecule is an antibody.

A molecule presented by an immune cell is a molecule expressed at the cell surface of an immune cell that is capable of being bound by a binding molecule. It will be appreciated by the skilled person that the presented molecule bound by the binding molecule can selected based on the immune cell it is intended to target. Suitable molecules presented by immune cells that may be bound by the binding molecule include TCR components or CD28 (for targeting T cells), BCR components or CD20 (for targeting B cells), natural cytotoxicity receptors (NCRs), CD16 or KIRs (for targeting NK cells), CD40 (for targeting antigen presenting cells such as macrophages and dendritic cells), and CD25 (for targeting Treg cells). Suitable molecules presented by targeted immune cells would be familiar to the skilled person, and a binding molecule which binds said suitable molecule can then be selected.

In certain embodiments, the binding molecule is selected from those binding a molecule selected from: a TCR component (e.g. CD3, the TCR heterodimer), an MHC-antigen complex, a BCR component, CD20, CD28, CD40, CD27, CD25, 4-1 BB, OX40, CD150, PD-1, CTLA4, TIM3, GARP and BTLA.

As well as targeting the nanofilament to a particular subset of immune cells, the binding molecule can provide additional immunomodulatory signals to the immune cell that complement the signal provided by the attached cytokine.

For example, if a pro-inflammatory cytokine (e.g. IL-2 or IFNα) is attached, the binding molecule may be a pro-inflammatory molecule. Suitable binding molecules include those that bind a TCR component (e.g. CD3, the TCR heterodimer), an MHC-antigen complex, a BCR component, CD20, CD27, CD28, CD40, 4-1 BB, CD150 or OX40. The skilled person will appreciate that to provide a pro-inflammatory signal, the binding molecule will induce signalling mediated by these molecules. Alternatively, the binding molecule may be pro-inflammatory by blocking signalling through anti-inflammatory receptors. For example, the binding molecule may block signalling through one or more of PD-1, CTLA4, TIM3, GARP or BTLA.

By way of further example, if an anti-inflammatory cytokine (e.g. TGFβ, IL-10) is attached to the nanofilament, the binding molecule may be an anti-inflammatory molecule. Suitable binding molecules include those that bind PD-1, CTLA4, TIM3, GARP or BTLA. The skilled person will appreciate that to provide an anti-inflammatory signal, the binding molecule will induce signalling mediated by these molecules. Alternatively, the binding molecule may be anti-inflammatory by blocking signalling through pro-inflammatory receptors. For example, the binding molecule may block signalling through one or more of a TCR component (e.g. CD3, the TCR heterodimer), an MHC-antigen complex, a BCR component, CD20, CD27, CD28, CD40, 4-1BB, CD150 or OX40

Accordingly, in certain embodiments, the binding molecule is pro-inflammatory. In certain such embodiments, the binding molecule binds a molecule selected from: a TCR component (e.g. CD3, the TCR heterodimer), an MHC-antigen complex, a BCR component, CD20, CD27, CD28, CD40, CD150, 4-1 BB or OX40. In certain alternative embodiments, the binding molecule binds a molecule selected from PD-1, CTLA4, TIM3, GARP or BTLA.

In certain alternative embodiments, the binding molecule is anti-inflammatory. In certain such embodiments, the binding molecule binds a molecule selected from: PD-1, CTLA4, TIM3, GARP or BTLA. In certain alternative embodiments, the binding molecule binds a molecule selected from a TCR component (e.g. CD3, the TCR heterodimer), an MHC-antigen complex, a BCR component, CD20, CD27, CD28, CD40, 4-1BB, CD150 or OX40.

As demonstrated herein, the provided nanofilaments are particularly effective at modulating T cell activity. Therefore, in certain preferred embodiments, the binding molecule binds a molecule presented by a T cell.

As further demonstrated in the Examples, the provided nanofilaments are particularly effective at activating T cells when the nanofilament comprises a binding molecule capable not only of targeting T cells as a subset, but also providing a stimulatory activation signal. Without wishing to be bound by theory, this is hypothesised to be because the dynamic range of the nanofilaments allows the formation of an effective immunological synapse including interaction of both the binding molecule and cytokine with the respective receptors. As a consequence, effective multiple activation signals are delivered to the T cell, resulting in effective activation.

For example, nanofilaments targeted cytokines to T cells using binding molecules targeting CD3 (specifically, anti-CD3 antibodies), which generically trigger all CD3 expressing T cells led to the synergistic effects demonstrated in the Examples.

Accordingly, in certain preferred embodiments, the binding molecule binds a TCR component molecule. As would be familiar to the skilled person, the T cell receptor (TCR) is a complex of component molecules. These component molecules include CD3 and the TCR heterodimer, which is predominantly formed of α and β TCR chains, though may be formed of γ and δ chains. In certain preferred embodiments, the binding molecule binds CD3 or a TCR heterodimer. In a preferred embodiment, the binding molecule binds CD3. In certain preferred embodiments, the binding molecule attached to the backbone is an anti-CD3 antibody.

Binding of a TCR component molecule, such as CD3, is hypothesised to be particularly effective as it promotes binding of the attached cytokine by T cells, and is also thought to promote clustering of TCR components together with cytokine receptors, thereby augmenting the immune modulation (e.g. stimulatory) effect of the cytokine.

It is also possible to modify this CD3-binding approach, which leads to synergistic activation of T cells generally, to a targeted delivery of cytokines to antigen-specific T cells. As demonstrated herein, by replacing αCD3 binding molecules with antigen-MHC complexes as the binding molecules, the nanofilaments deliver the attached cytokines preferentially to antigen-specific T cells and induce potent responses in antigen-specific T cells.

Therefore, in certain preferred embodiments, the binding molecule is an MHC-antigen complex.

Such a protein complex is able to bind a TCR heterodimer on a T cell specific for the antigen complexed with MHC (major histocompatibility complex). The particular antigen bound to the MHC complex can be any suitable T cell antigen (i.e. an antigen recognised by a T cell receptor) and could be selected by the skilled person depending on the T cell population targeted by the nanofilaments. For example, if it is intended to activate and/or expand a population of T cells for cancer therapy, the antigen forming the MHC-antigen complex attached to the nanofilament would be an antigen from the cancer to be treated. It is within the ability of the skilled person to select a suitable antigen from a targeted disease or condition.

Similarly, a suitable MHC (or HLA) molecule to form the complex with the selected antigen can also be selected by the skilled person. In preferred embodiments the MHC molecule of the MHC-antigen complex is a human MHC molecule (also referred to as an HLA molecule). In preferred embodiments, the MHC molecule is autologous to the T cells to be targeted because autologous MHC molecules will exhibit reduced levels of cross-reactivity.

As demonstrated herein, the provided nanofilaments are particularly effective when the binding molecule is present at certain densities.

In certain embodiments, the binding molecule is attached to the backbone at a density of at least one molecule about each 130 nm—that is, two binding molecules (e.g. antibodies or antigen-MHC complexes) attached to a backbone are separated by no more than about 130 nm. In certain embodiments the binding molecule is attached to the backbone at a density in the range of from one molecule about each 130 nm to one molecule about each 10 nm. In certain preferred embodiments the binding molecule is attached to the backbone at a density in the range of from one molecule about each 130 nm to one molecule about each 75 nm. In certain preferred embodiments the binding molecule is attached to the backbone at a density in the range of from one molecule about each 130 nm to one molecule about each 80 nm.

In certain alternative preferred embodiments, the binding molecule is attached to the backbone at a density in the range of from one molecule about each 100 nm to one molecule about each 250 nm. Preferably, the binding molecule is attached to the backbone at a density in the range of from one molecule about each 140 nm to one molecule about each 250 nm. Further preferably, the binding molecule is attached to the backbone at a density in the range of from one molecule about each 140 nm to one molecule about each 210 nm.

In certain embodiments, the nanofilament has from 2-10 molecules of the binding molecule attached to the backbone. In certain embodiments the nanofilament has 2, 3, 4, 5, 6, 7, 8, 9 or 10 molecules of the binding molecule attached to the backbone. In certain embodiments, the nanofilament has 2, 4 or 10 molecules of the binding molecule attached to the backbone. In certain embodiments, the nanofilament has 3-5 molecules of the binding molecule attached to the backbone. In certain preferred embodiments, the nanofilament has 4 molecules of the binding molecule attached to the backbone. In certain preferred embodiments, the nanofilament has 3 molecules of the binding molecule attached to the backbone.

It will be appreciated by the skilled person that polymerisation is a random process, as is the attachment of binding molecules to the polymer backbone. Therefore, when many nanofilaments are being produced, the above-described densities and number of molecules refer to the mean density or number of the molecules and do not exclude the possibility of two individual binding molecules falling outside the stated density or a particular nanofilament having a number of molecules attached that is outside the stated amount.

In certain embodiments, the molecules of the first cytokine and the molecules of the binding molecule are attached to the nanofilament backbone at a ratio in the range of from about 1:2 to about 5:1, optionally at a ratio in the range of from about 1:2 to about 4:1. In certain embodiments, the molecules of the first cytokine and the molecules of the binding molecule are attached to the nanofilament backbone at a ratio in the range of from about 1:1 to about 4:1. In certain embodiments the molecules of the first cytokine and the molecules of the binding molecule are attached to the nanofilament backbone at a ratio in the range of from about 1:2 to about 5:2, optionally from about 3:4 to about 5:2.

In certain embodiments, there is approximately 1 to 2 molecules of the first cytokine per binding molecule attached to the backbone. In certain preferred embodiments, there is approximately 1.3-1.7 molecules of the first cytokine per binding molecule attached to the backbone.

As described elsewhere herein, attachment of the binding molecule molecules to the polymeric backbone can be achieved through reaction with monomer units functionalised with functional moieties. The density of binding molecule molecules can be varied by modifying the quantity of binding molecules in this reaction relative to functional moieties.

In certain alternative embodiments, the density of the binding molecule can be varied by varying the ratio of functionalised to non-functionalised monomers during polymerisation, thereby varying the subsequent density of attachment of binding molecules. In certain such embodiments, this density can be further modified by the frequency of conversion of functionalised monomers, for example conversion to moieties such as biotin or streptavidin.

In a further aspect of the invention is provided a nanofilament comprising a plurality of molecules of a binding molecule attached to a polymeric backbone. Embodiments set out above in relation to the nanofilaments of the first aspect relating to the binding molecule apply equally and independently to this aspect. For example, in certain embodiments the binding molecule is an antibody, e.g. an anti-CD3 antibody. In certain embodiments the binding molecule is an antigen-MHC complex.

Attachment

The nanofilaments provided herein comprise cytokines (and optionally binding molecules) attached to the polymeric backbone. That is, the cytokines (and optionally binding molecules) are bound to the polymeric backbone and not in soluble form.

In certain preferred embodiments described elsewhere herein, the polymeric backbone is formed of functionalised monomers comprising functional moieties. In such embodiments, attachment of the cytokine or binding molecules is via the functional moiety.

Suitable means for attaching molecules to the polymeric backbone are familiar to the skilled person and include so-called click chemistry. For example, when attachment is via a click reaction, the molecule to be attached (cytokine or binding molecule) and functional moiety form an appropriate click pair. Suitable click pairs would be familiar to the skilled person and include azide and a BCN, DBCO, or DIBO group, a copper(I)-catalyzed azide alkyne cycloaddition (CuAAC) pair, or tetrazine and TCO.

As described elsewhere herein, the density of cytokine or binding molecules attached to the polymeric backbone can be varied. In such embodiments where attachment of the molecules is via the functional moieties of the polymeric backbone, density of a molecule can be varied by changing the amount of the molecule (e.g. cytokine or binding molecule) relative to the functional moiety.

Accordingly, in certain embodiments, functionalised cytokine is reacted with the functionalised polymeric backbone at a concentration of from 0.05 to 1 equivalents of functionalised cytokine per polymeric functional moiety. In certain embodiments, functionalised cytokine is reacted with functionalised polymeric backbone ata concentration of from 0.1 to 0.5 equivalents per polymeric functional moiety. In certain embodiments, functionalised cytokine is reacted with the functionalised polymeric backbone at a concentration of 0.1, 0.2 or 0.5 equivalents per polymeric functionalised moiety.

Accordingly, in certain embodiments, functionalised binding molecule is reacted with the functionalised polymeric backbone at a concentration of from 0.05 to 1 equivalents of functionalised binding molecule per polymeric functional moiety. In certain embodiments, functionalised binding molecule is reacted with functionalised polymeric backbone at a concentration of from 0.1 to 0.5 equivalents per polymeric functional moiety. In certain embodiments, functionalised binding molecule is reacted with the functionalised polymeric backbone at a concentration of 0.25 equivalents per polymeric functionalised moiety.

In certain embodiments the cytokine (and optionally a binding molecule) is attached directly. That is, the immune factor (cytokine or binding molecule) is bound directly to the backbone—for example, where the backbone is formed of functionalised and non-functionalised monomers, the immune factor (e.g. cytokine) can be directly attached to a functionalised monomer, for instance as a result of reaction with an azide group of a functionalised monomer.

In certain alternative embodiments, the cytokine, binding molecule (when present), or both cytokine and binding molecule are attached indirectly, via a linker/side-chain which separates the cytokine or binding molecule from the polymer backbone. In such embodiments, the linker or side-chain is attached to the backbone and the cytokine or binding molecule is attached to the linker or side-chain. In certain embodiments where the backbone is formed of functionalised and non-functionalised monomers, the linker or side chain is attached to a functionalised monomer, for example as a result of a click reaction with a functional moiety of the backbone, and the cytokine or binding molecule is attached to the linker or side-chain. Means for attaching a cytokine or binding molecule to a linker or side-chain are well-known in the art and would be familiar to the skilled person. For the avoidance of doubt, when a cytokine or binding molecule is attached to the backbone indirectly via a side-chain/linker, the cytokine or binding molecule is attached to the side-chain/linker so as to allow the cytokine or binding molecule to bind its cognate receptor or ligand.

In certain preferred embodiments attachment of the cytokine (and the binding molecule when present) is via a PEG linker. In such embodiments, a PEG linker is a chain bound at one end to the cytokine or binding molecule and at the other to the backbone, where the chain comprises a number of ethylene glycol units which separate the cytokine or binding molecule from the polymer backbone.

In certain embodiments the PEG linker separating the cytokine or binding molecule from the polymer backbone comprises 1-100 ethylene glycol units, for example 1-90, 1-80 or 1-70 ethylene glycol units. In certain preferred embodiments the PEG linker comprises 1-10 ethylene glycol units, optionally 2-8, optionally 2, 4, 6 or 8 ethylene glycol units. In certain preferred embodiments the PEG linker has 4 ethylene glycol units. Use of such a PEG linker is particularly advantageous in improving availability of the bound cytokine or binding molecule to an immune cell.

For the avoidance of doubt, where a linker is described as a PEG linker comprising a number of ethylene glycol units, the linker may also include moieties that have allowed the linker to attach both to the cytokine or binding molecule and also to the backbone. For instance, as described in the Examples below, a PEG linker may be attached to a functionalised monomer of a polymer nanofilament as a result of reaction with an azide group on the monomer, for example via a "click" reaction between the azide and a BCN, DBCO, or DIBO group, a copper(I)-catalyzed azide alkyne cycloaddition (CuAAC) pair, or tetrazine and TCO. Other examples of "click" chemistry reactions suitable for attaching a PEG linker to the nanofilament would be familiar to the skilled person.

In certain embodiments, the linker is a cleavable linker.

Certain Preferred Embodiments

In a preferred embodiment is provided a nanofilament comprising a plurality of molecules of a first cytokine attached to a PIC polymer backbone, wherein the first cytokine is IL-2.

Preferably the nanofilament further comprises a plurality of a binding molecule.

Preferably the binding molecules is selected from an anti-CD3 antibody and an MHC-antigen complex.

Preferably the binding molecule is an anti-CD3 antibody. Alternatively and preferably, the binding molecule is an MHC-antigen complex.

Preferably the nanofilament further comprises a plurality of molecules of a second cytokine. Preferably said second cytokine is IFNα.

In a further preferred embodiment is provided a nanofilament comprising a plurality of molecules of a first cytokine attached to a PIC polymer backbone, wherein the first cytokine is IFNα.

Preferably the nanofilament further comprises a plurality of a binding molecule, wherein the binding molecule is an anti-CD3 antibody.

Preferably the nanofilament further comprises a plurality of molecules of a second cytokine. Preferably said second cytokine is IL-2.

In certain preferred embodiments, the nanofilament is a PIC nanofilament comprising a plurality of molecules of IL-2 attached to a PIC backbone, and further comprises a plurality of anti-CD3 antibody molecules attached to the PIC backbone. In certain alternative preferred embodiments, the nanofilament is a PIC nanofilament comprising a plurality of molecules of IFNα attached to a PIC backbone, and further comprises a plurality of anti-CD3 antibody molecules attached to the PIC backbone. In certain alternative preferred embodiments, the nanofilament is a PIC nanofilament comprising a plurality of molecules of IFNα attached to a PIC backbone, a plurality of molecules of IL-2 attached to a PIC backbone, and a plurality of anti-CD3 antibody molecules attached to the PIC backbone.

In certain preferred embodiments, the cytokine(s) and anti-CD3 antibody molecules are attached to the PIC backbone indirectly, optionally via a PEG linker.

In certain embodiments, the nanofilament is a PIC nanofilament comprising a plurality of molecules of IL-2 attached to a PIC backbone, and further comprises a plurality of antigen-MHC complex molecules attached to the PIC backbone. In certain alternative preferred embodiments, the nanofilament is a PIC nanofilament comprising a plurality of molecules of IFNα attached to a PIC backbone, and further comprises a plurality of antigen-MHC complex molecules attached to the PIC backbone. In certain alternative preferred embodiments, the nanofilament is a PIC nanofilament comprising a plurality of molecules of IFNα attached to a PIC backbone, a plurality of molecules of IL-2 attached to a PIC backbone, and a plurality of antigen-MHC complex molecules attached to the PIC backbone.

In certain preferred embodiments, the cytokine(s) and antigen-MHC complex molecules are attached to the PIC backbone indirectly, optionally via a PEG linker.

Compositions

Nanofilaments according to the invention can be formulated as compositions comprising one or more nanofilaments of the invention. In certain embodiments, the composition comprises one or more nanofilaments in suspension in a carrier, for example an aqueous carrier such as water or saline.

In certain embodiments, the composition may comprise a second type of nanofilament. That is, the composition may comprise a first type nanofilament as described herein—i.e. a nanofilament comprising a cytokine attached to a polymeric backbone, optionally further comprising a binding molecule also attached to the backbone. In addition to this first type of nanofilament, the composition may further comprise a second type of nanofilament. Said second nanofilament may be a nanofilament according to the present invention, but where the cytokine attached to the second nanofilament is different from the cytokine attached to the first nanofilament. In such embodiments, the second PIC nanofilament is a nanofilament according to the embodiments herein described.

Alternatively, said second type of nanofilament may be a nanofilament that is not according to the invention—for example, the second nanofilament may comprise a binding molecule attached to a backbone, but with no cytokine attached. In certain such embodiments, the second nanofilament of the composition may comprise a binding molecule attached to the backbone, where the binding molecule is as defined herein. In certain such embodiments, the binding molecule may be an anti-CD3 or anti-CD28 antibody.

Such compositions may be advantageous in providing additional immune signals to an immune cell population contacted by the composition, for example further co-stimulatory signals to potentiate the activation signals provided by nanofilaments as herein described.

In certain embodiments, the composition is a pharmaceutical composition—that is, it is suitable for administration to a human subject. In certain such embodiments the nanofilaments are suspended in a pharmaceutically acceptable carrier, for example an aqueous carrier such as water or saline.

Methods of Use

Nanofilaments and compositions provided herein are particularly effective at modulating the activity of immune cells that contact the nanofilaments. Modulation of the activity of immune cells (also referred to herein as immunomodulation) refers to changing the activity or proliferative state of the cells. Immunomodulation may be by stimulating activity or promoting proliferation of the immune cells, or by inhibiting activity or proliferation of the immune cells.

This immunomodulatory effect can be used to modulate the activity of immune cells in the laboratory or in a therapeutic context where changing the patient's immune response is beneficial.

Therefore, in a further aspect is provided a method of modulating the activity of a population of immune cells, said method comprising contacting the cells with a nanofilament or composition provided herein. In preferred embodiments, the immune cells are T cells.

In certain embodiments, the method may be conducted in a laboratory—i.e. the method is an in vitro or ex vivo method. For example, the nanofilament or composition can be used to immunomodulate an immune cell population in culture. By way of further example, the nanofilament or composition can be used to immunomodulate an immune cell that has been obtained from a human subject. Such ex vivo use can be advantageous, for example, when preparing immune cells for transplant, e.g. autologous or allogenic cell transfer. Nanofilaments and compositions provided herein will be particularly useful for immunomodulation (e.g. expansion) of T cells for CAR T cell therapy.

In certain embodiments the method further comprises contacting the cells with a soluble cytokine. Suitable cytokines can be selected by the skilled person depending on the desired immunomodulation. In certain embodiments the soluble cytokine is IL-2.

In certain embodiments, the method can comprise a first step of contacting the cells with a nanofilament comprising a first cytokine, or first composition comprising said second nanofilament, and a second step comprising contacting the cells with a second nanofilament comprising a second cytokine, or second composition comprising said second nanofilament. In such embodiments, the first and second cytokine are different. Such methods are particularly advantageous as they allow the cell population to be "primed" such that a first cellular response is induced (e.g. proliferation and/or cellular cytokine production) and then restimulated such that a second cellular response is induced, for example a response that is complementary to the first response or which enhances the first response (e.g. increases cytotoxicity or promotes further proliferation).

In certain alternative embodiments, the method is conducted in vivo—that is, the population of immune cells is in circulation in a subject when it contacts the nanofilament or composition.

In vivo methods according to such embodiments may be effective for treating disorders in which modulating the activity of immune cells is desirable.

In certain embodiments, the method is a method for stimulation of immune cell activity. In such embodiments, the nanofilaments will have pro-inflammatory cytokines attached in order to promote immune cell activity, proliferation or both. Suitable pro-inflammatory cytokines are described elsewhere herein and include: IL-2, IL-12, IL-7, IL-15, IL-17, IL-6, IL-1, IFNα, IFNγ, TNF (such as TNFα), and GM-CSF. In certain preferred embodiments, the cytokine is IL-2 or IFNα. In such embodiments when the nanofilament comprises a binding molecule, the binding molecule may be a molecule that provides an activation signal to the immune cell. For example, the binding molecule may be a molecule that binds a molecule selected from: a TCR component (e.g. CD3, the TCR heterodimer), an MHC-antigen complex, a BCR component, CD20, CD27, CD28, CD40, 4-1BB, ICOS, CD150, and OX40.

In certain embodiments of methods of promoting immune cell activity when the nanofilament comprises a binding molecule, the binding molecule binds a TCR component (e.g. CD3, the TCR heterodimer). In such embodiments, the immune cell can be further contacted with a second binding molecule that binds a co-stimulatory T cell receptor such as CD28, OX40, 4-1 BB, or ICOS. In certain such embodiments, the second binding molecule is an antibody, for example an anti-CD28 antibody. In certain alternative such embodiments, the second binding molecules is the natural ligand for the co-stimulatory receptor. In certain alternative embodiments, the second binding molecule is an immune checkpoint inhibitor, for example an antibody that reduces the activity of an immune checkpoint receptor selected from selected from: PD-1, CTLA4, TIM3, GARP and BTLA. In certain preferred embodiments, the second binding molecule is bound to a nanofilament. In certain preferred such embodiments, the second binding molecule is bound to the same nanofilament as the binding molecule binding a TCR component.

Methods stimulating immune cell activity may be used to treat disorders which would benefit from immune cell activation. Examples of such disorders include cancers known to be treated by pro-inflammatory cytokine therapy (e.g. IL-2 or IFNα), including hairy-cell leukaemia, Kaposi's sarcoma, follicular lymphoma, chronic myeloid leukaemia, malignant melanoma, and renal cell carcinoma.

In certain embodiments, the method is a method for inhibition of immune cell activity. In such methods, the nanofilaments will have anti-inflammatory cytokines attached. Suitable anti-inflammatory cytokines include IL-4, TGFβ, IL-13 and IL-10. In such embodiments when the nanofilament comprises a binding molecule, the binding molecule may be a molecule that provides an inhibitory signal to the immune cell. For example, the binding molecule may be a molecule that binds (and induces signalling from) a molecule selected from: PD-1, CTLA4, TIM3, GARP and BTLA. In certain such embodiments, the binding molecule is an antibody. In certain alternative such embodiments, the second binding molecules is the natural ligand for the co-receptor.

Methods inhibiting immune cell activity may be used to treat disorders which would benefit from immune cell suppression. Examples of disorders by such methods of immunosuppression include autoimmune diseases, such as type 1 diabetes, rheumatoid arthritis, celiac disease, inflammatory bowel disease, multiple sclerosis, systemic lupus erythematosus, and autoimmune hepatitis.

Therefore, provided herein is a method of immunotherapy comprising contacting a population of immune cells with a nanofilament or composition as provided herein. In certain embodiments, the method is a method of treating cancer. In certain such embodiments, the cancer is selected from the group consisting of: hairy-cell leukaemia, Kaposi's sarcoma, follicular lymphoma, chronic myeloid leukaemia, malignant melanoma, and renal cell carcinoma.

In certain alternative embodiments, the method is a method of treating an autoimmune disease. In certain such embodiments, the autoimmune disease is selected from the group consisting of: type 1 diabetes, rheumatoid arthritis, celiac disease, inflammatory bowel disease, multiple sclerosis, systemic lupus erythematosus, and autoimmune hepatitis.

As demonstrated herein, nanofilaments are particularly effective at promoting proliferation of T cells, as well as stimulating activity of T cells as evidenced by increased inflammatory cytokine (e.g. IFNγ) production by the stimulated T cells. Accordingly, in preferred embodiments, the method is a method of activating a population of immune cells, preferably T cells. In such embodiments, the method stimulates the immune cells and/ or increases proliferation of the immune cells.

As demonstrated in the Examples, contacting a population of T cells with nanofilaments according to the invention can reduce PD-1 upregulation on the activated T cells. PD-1 is an immune checkpoint molecule whereby signalling through PD-1 can suppress an immune response. Contacting a population of T cells with nanofilaments can therefore further modulate immune response of a T cell population by reducing PD-1 expression. This immunomodulatory effect is expected to particularly advantageous in the therapy of conditions known to suppress disease-specific T cell activity, such as cancer. Therefore, in certain embodiments, contacting a population of immune cells with a nanofilament as provided herein decreases PD-1 expression on the T cell population. In certain preferred such embodiments, the nanofilament comprises a plurality of IFNα molecules attached to the backbone.

In certain embodiments, the invention provides a method of treating immunosuppression comprising contacting a population of immune cells in vivo with a nanofilament or composition according to the invention. In certain embodiments, the invention provides a method of treating cancer comprising contacting a population of immune cells in vivo with a nanofilament or composition according to the invention.

As herein described, in certain embodiments nanofilaments may comprise a binding molecule which binds a molecule presented by an immune cell. In certain such embodiments, said binding molecule may be an MHC-antigen complex. Said nanofilaments allow targeting of T cells that are specific for the complexed antigen. By selecting an antigen specific for the disease to be treated, such nanofilaments (and compositions comprising said nanofilaments) can be used to selectively modulate the activity of antigen-specific (and therefore disease-specific) T cells. This will be advantageous as not only is the activity of disease-specific T cells increased, off-target effects are reduced, thereby limiting side-effects.

Such immunomodulation of antigen-specific T cells can be to promote T cell activity. In such embodiments, the antigen-specific T cells can be further contacted with a second binding molecule that binds a co-stimulatory molecule presented by the T cells. Said co-stimulatory molecule provides the second activation signal leading to activation of the antigen-specific T cells. Suitable co-stimulatory molecules bound by the second binding protein include CD28, OX40, 4-1BB, and ICOS.

Alternatively, the immunomodulation of the antigen-specific T cells can be to inhibit activity of the T cells. Recognition of MHC-presented antigen by T cells in the absence of a co-stimulatory signal is known to induce anergy. Anergic T cells exhibit reduced or a lack of pro-inflammatory response to the cognate antigen, and can express anti-inflammatory cytokines such as IL-10.

Inducing anergy in antigen-specific T cells can be used to treat conditions such as autoimmune diseases (e.g. diabetes mellitus, rheumatoid arthritis, multiple sclerosis) where immunosuppression is advantageous. As noted above, by selecting an antigen specific for the disease to be treated, the nanofilaments provided herein (and compositions comprising said nanofilaments) can be used to selectively modulate the activity of antigen-specific (and therefore disease-specific) T cells. This will be advantageous as not only is the activity of disease-specific T cells increased, off-target effects are reduced, thereby limiting side-effects.

Accordingly, in certain embodiments, the invention provides a method of treating a disease comprising contacting a population of immune cells in vivo with a nanofilament or composition comprising an MHC-antigen complex attached to the backbone, where the disease treated is characterised by the antigen of the MHC-antigen complex.

In certain embodiments, the method promotes immune activity of T cells specific for the complexed antigen. In such embodiments, the population of immune cells is further contacted with a second binding molecule that binds a co-stimulatory T cell receptor. In certain such embodiments, the co-stimulatory T cell receptor is CD28, OX40, 4-1 BB, or ICOS.

In certain such embodiments, the second binding molecule is an antibody, for example anti-CD28 antibody. In certain preferred embodiments, the second binding molecule is bound to a nanofilament, for example a PIC nanofilament. In certain preferred such embodiments, the second binding molecule is bound to the same nanofilament as the MHC-antigen complex.

In certain such embodiments, the disease treated by the method is cancer. In certain embodiments the method is a method of treating hairy-cell leukaemia, Kaposi's sarcoma, follicular lymphoma, chronic myeloid leukaemia, malignant melanoma, or renal cell carcinoma.

In certain alternative embodiments, the method inhibits activity of antigen-specific T cells in the population of immune cells. In certain embodiments, the method induces anergy of antigen-specific T cells.

In certain such embodiments, the method is a method of treating an autoimmune disease. In certain such embodiments, the autoimmune disease is selected from the group consisting of: type 1 diabetes, rheumatoid arthritis, celiac disease, inflammatory bowel disease, multiple sclerosis, systemic lupus erythematosus, and autoimmune hepatitis.

In a further aspect, the invention provides a nanofilament or composition as provided herein for use in therapy.

In a further aspect, the invention provides a nanofilament or composition as provided herein for use in treating cancer.

In a further aspect, the invention provides a nanofilament or composition as provided herein for use in treating immunosuppression.

In a further aspect, the invention provides a nanofilament or composition as provided herein for use in treating an autoimmune disease.

In a further aspect, the invention provides a nanofilament or composition comprising an MHC-antigen complex attached to the backbone, for use in treating a disease characterised by the antigen of the MHC-antigen complex.

The above description provides suitable embodiments of the invention defined by the appended claims. Nevertheless the skilled person will appreciate that various modifications, additions and alterations may be made to the invention by one skilled in the art without departing from the spirit and scope of the invention as defined in the appended claims.

Citations and documents cited herein are hereby incorporated herein by reference.

The following Examples provide experimental demonstration of certain non-limiting embodiments of the invention.

EXAMPLES

Materials and Methods

Materials

Zeba™ Spin Desalting Columns (7K and 40K MWCO), Celltrace Violet Cell proliferation kit, tosyl-activated Dynabeads M450, Dynabeads human T-activator CD3/CD28 and AlexaFluorF647-NHS ester (AF647) were purchased from ThermoFisher. Magnetic mono-avidin beads were from Bioclone. Azide-PEGS-NH2 (O-(2-Aminoethyl)-O'-(2-azidoethyl)pentaethylene glycol) was obtained from Sigma-Aldrich, anti-CD3 (Clone OKT3) was from BioXCell. Recombinant human IL-2 and IFNα were purchased from Cell Sciences, IL-2 and TNFα ELISA Ready-set go kits were from eBioscience. Pan T cell isolation kit and propidium iodide solution were obtained from Miltenyi. Antibodies anti-CD4-APC-Cy7, anti-PD-1-BV510, anti-CD107a-PECy5, anti-CD25-PE, anti-CD4-BV421, anti-CD8-BV510 and anti-IFNγ-BV421 were from BD Biosciences, and antibodies anti-Granzyme B-PE, anti-CD8-PECy7 and anti-CD4-PECy7 were from Biolegend. Antibodies anti-TNFα-PerCPCy5.5 and anti-IL-2-PE were from eBioscience. DBCO-PEG4-NHS was purchased from Jena Bioscience. Atto488-NHS ester (A488) was obtained from Atto-TEC GmbH. 30 kDa Amicon Ultra-15 ultrafiltration membranes were from Merck Millipore. X-vivo medium was purchased from Lonza. Cytoperm/cytofix buffer kit was purchased from BD Biosciences.

Synthesis of Polyisocyanopeptide (PIC) Backbones

The polyisocyanopeptides (PICs) used in this study were synthesized according to the procedures described in Mandal et al. Therapeutic Nanoworms: Towards Novel Synthetic Dendritic Cells for Immunotherapy. *Chem. Sci.* 2013, 4, 4168, Koepf et al, European Polymer Journal, 49 (6), 2013 p.1510-1522, and Mandal et al. Polymer-Based Synthetic Dendritic Cells for Tailoring Robust and Multifunctional T Cell Responses. *ACS Chem. Biol.* 2015, 10, 485-492, both of which are incorporated herein by reference.

Briefly, non-functional methoxy- and functional azide-terminated monomers were reacted in a 30:1 ratio using a nickel catalyst (Scheme A), statistically yielding a polymer with a functional azide group every 3.5 nm. Next, 50% of the azides were converted to biotin using DBCO-PEG$_4$-biotin as described in Hammink et al. Affinity-Based Purification of Polyisocyanopeptide Bioconjugates. *Bioconjug. Chem.* 2017, acs.bioconjchem.7b00398, incorporated herein by reference.

The resulting azide-biotin-PICs were analysed with atomic force microscopy (Nanoscope III, Digital Instruments), operating in tapping mode in air, using NSG10 tips. For these experiments, the polymer (10 μg/ml) was dropcasted onto freshly cleaved mica and incubated for 5 min. After removing the liquid, the substrate was dried under nitrogen flow (FIG. 1A). These AFM images were used to determine the polymer length with ImageJ, yielding an average length of 383 nm (FIG. 1B).

Protein Functionalization

In order to functionalize anti-CD3 antibodies, the storage buffer was exchanged to 50 mM borate buffer pH 8.5, using Amicon ultrafiltration membranes (30 kD MWCO). For αCD3, IL-2 and IFNα functionalization between 1-5 mg of protein was used at concentrations between 1-3 mg/ml. For αCD3, 5 equivalents of DBCO-PEG4-NHS ester and 2.5 equivalents of A488-NHS ester was added. IL-2 and IFNα were reacted with 4 equivalents of DBCO-PEG4-NHS ester and 2 equivalents of AF647-NHS ester. After incubation for 2 h at 4° C. on a rotator, functionalized αCD3 was purified over a 5 ml 40K Zeba spin desalting column, while the cytokines were purified over a 2 ml 7K Zeba spin desalting column.

Analysis of Functionalized Proteins

To determine the degree of DBCO and dye labelling, the proteins were analysed using a Nanodrop 2000c spectrophotometer. Absorbance at 280, 309, 501 and 650 nm was used to calculate the concentrations of proteins, DBCO and dye. After correcting for the overlap in the absorbance spectra of the individual molecules, the respective concentrations were calculated using the molar extinction coefficients of the proteins used: (210000 M-1 cm-1 for αCD3, 11900 M-1 cm-1 for IL-2 and 18700 M-1 cm-1 for IFNα). This yielded ratios of 1:3.6:2 for αCD3:DBCO:A488, 1:2:0.5 for IL-2:DBCO:AF647 and 1:2:0.5 for IFNα:DBCO:AF647. Protein yields were typically between 60-80%. The degrees of labelling were confirmed for IL-2 and IFNα using MALDI-ToF (Bruker microflex) with sinapinic acid as the matrix (FIG. 2).

PIC-Protein Conjugate Synthesis

To obtain the PIC-αCD3/cytokine conjugates, DBCO-functionalized αCD3 (0.25 equivalents with respect to the reactive azide groups on the polymer) was added to the azide-biotin-PIC (100 μg, 1 mg/ml in Phosphate Buffered Saline; PBS) and incubated. After 2 h, IL-2 or IFNα was added to the reaction mixture and incubated at 4° C. on a rotator overnight.

To obtain the low, medium and high density samples, 0.1, 0.2 or 0.5 equivalents of cytokine (with respect to azide) were used. After coupling, the protein-functionalized PICs were purified over magnetic mono-avidin beads as described in Hammink 2017, ibid. The PIC-protein conjugates were incubated with magnetic mono-avidin beads (1 ml bead solution for each polymer sample) for 2 h at 4° C., after which they were washed extensively with PBS+0.1% Tween-20 (2x) and PBS (4x), making use of a Dynal MPC-L Magnetic Particle Concentrator. To elute the conjugates from the beads, they were incubated in PBS containing 2 mM biotin (biotin elution buffer) on a rotator for 2 h at 4° C.

Functionalization of pMHC Complexes

PIC nanofilaments were also functionalised with an exemplary MHC (HLA-A201 MHC presenting NY-ESO-I peptide (pMHC)) to demonstrate antigen specific stimulation. To functionalize pMHC with DBCO and Atto488 dyes, between 200-1000 ug of protein complexes were mixed with DBCO-4PEG-NHS ester and atto488-NHS ester in PBS in 1:4:4 ratios. After incubation for 2 h at 4° C. on a rotator, functionalized pMHC was purified over a 2 mL 7K Zeba spin column. To determine the degree of DBCO and Atto488 labelling, the purified complexes were analyzed by measuring their absorbance at 280, 309 and 501 nm on a nanodrop 200c spectrophotometer.

After correcting for overlap of absorbance spectra of the individual molecules, protein, DBCO and Atto488 concentrations were calculated using molar extinction coefficients of the individual molecules (12000 M-1cm-1 for DBCO, 90000 M-1cm-1 for Atto488). Protein concentrations determined by nanodrop were verified using a micro BCA protein assay.

Conjugation of pMHC to PICs

To develop antigen-specific PIC-based aAPCs, DBCO/Atto488-functionalized pMHC (0.5 equivalents with respect to azide groups on the PICs), and DBCO/AlexaFluor647-functionalized IL-2 (0.5 equivalents) were added to 60 ug of azide-biotin functionalized PICs (1 mg/mL in PBS) and incubated overnight at 4° C. on a rotator. PIC-protein conjugates were purified over magnetic monoavidin beads as described in literature (Hammink, Eggermont et al., ACS Bioconj. Chem. 2017). For this, reaction mixtures were incubated with 1mL of magnetic monoavidin bead solution for 2 hours at 4° C., after which they were washed with PBS+0.1%tween-20 (2×) and PBS (4×) on a Dynal MPC-L Magnetic Particle Concentrator. Polymers were eluted from beads by incubation with PBS containing 2 mM biotin for 2 hours at 4° C. on a rotator. Concentrations of proteins conjugated to PICs were determined using a Tecan Spark 10M fluorescence plate reader.

Analysis of PIC Protein Conjugates

The protein concentrations in all PIC-protein conjugate samples were determined using a Tecan Spark 10M fluorescence microplate reader. Unbound DBCO/dye-functionalized proteins were used as standard for each measurement. The samples (100 µl) were pipetted into black, flat-bottom non-binding 96-well microplates (Greiner Bio-One). A488 and AF647 were exited at 490 nm and 635 nm, and detected at 535 nm and 680 nm, respectively. The polymer concentration was measured using circular dichroism (CD) (JASCO J-810). 100 µl of each PIC-protein conjugate was filled into a 1 cm cuvette and the CD spectrum was measured using biotin elution buffer as a blank. The peak value at 272 nm was used to determine the polymer concentration, using an extinction coefficient of 547.8 mdeg ml cm$^{-1}$, which was determined with a standard curve of different polymer concentrations as described in Hammink 2017, ibid. To confirm the absence of unbound proteins after purification, the PIC-protein conjugates were further analysed with SDS-PAGE. A standard of unbound protein was loaded onto these gels for quantifying the amount of protein that was not fully removed during purification. After electrophoresis, the gels were scanned with a Typhoon trio+gel scanner to detect the AF647 dye coupled to the cytokines.

Microbead-Protein Conjugation

To synthesize microbead-based aAPCs, tosyl-activated Dynabeads were reacted with 1000 equivalents of azide-PEGS-NH2 in 50 mM borate buffer (pH 8.5) overnight at room temperature.

The beads were washed 4× with PBS to remove excess azide-PEGS-NH2. The beads were incubated with the previously synthesized DBCO- and Atto488-labelled αCD3 antibodies. Following overnight reaction at 4° C., the beads were again washed with PBS (4×) to remove excess αCD3 and DBCO- and AF647-labelled IL-2 was added to one part of the αCD3-labelled beads. Again, the beads were reacted overnight at 4° C. and washed with PBS containing 0.1% BSA and 2 mM EDTA (2×) and PBS (4×) to remove excess IL-2. αCD3-functionalized and αCD3/IL-2-functionalized beads were analyzed using a BD FACSverse flow cytometer. The αCD3 and IL-2 concentrations were measured in the supernatants of the reaction mixtures to determine the amount of proteins coupled to the different microbeads. For this measurement, the samples were analyzed in a Tecan Spark 10M fluorescence microplate reader, relative to a standard of the unbound and fluorescently labelled proteins. Bead-coupled αCD3 and IL-2 densities were 43 and 58 ng/106 beads, respectively.

Alginate-Protein Conjugate Synthesis

To obtain the alginate-αCD3 and alginate-αCD3/IL-2 conjugates, first alginate was functionalized with an azide linker. For this, 250 mg of sodium alginate (Novamatrix, Mw: 75-200 kDa, viscosity:
68 mPa) was dissolved in MES buffer (pH 6.5, 30 ml) and EDC (713 mg, 4.6 mmol) and NHS (332 mg, 2.9 mmol) were added to activate the carboxylic acids. After 10 minutes of stirring, 11-azido-3,6,9-trioxaundecane-1-amine (640 mg, 2.9 mmol) was added and the solution was stirred overnight at room temperature. The reaction mixture was precipitated in 300 mL acetone and the azide-alginate was collected by filtration (mg, %).

The azide-alginate was dissolved in PBS (1 mg/ml) and 50 µL was reacted with DBCO-functionalized αCD3 (0.01 equivalents compared to azides on the alginate). In a similar way, azide-alginate (50 µL of 1 mg/ml in PBS) was reacted with DBCO-functionalized αCD3 (0.01 equivalents compared to azides on the alginate) as well as DBCO-functionalized IL-2 (0.02 equivalents compared to azides on the alginate). The two alginate conjugates were purified using Amicon ultrafiltration membranes (10 kD MWCO), to finally obtain αCD3 functionalized alginate and αCD3/IL-2 functionalized alginate in PBS. Protein concentrations were determined using a fluorescent plate reader (Tecan spark M10), which yielded an IL-2: αCD3 ratio of 1.3.

Antigen-Specific Stimulation of NY-ESO-I TCR-Expressing CD8 T Cells

Human peripheral blood lymphocytes were isolated from buffy coats obtained from healthy donors using Ficoll density centrifugation. CD8+ T cells were isolated from peripheral blood lymphocytes using the Miltenyi CD8+ T cell isolation kit. After isolation, mRNA transfection using a Bio-rad gene pulser was done to induce expression of an NY-ESO-I-specific TCR. 50.000 TCR-transfected CD8+ T cells were stimulated with 50-100 ng/mL soluble pMHC or PIC-pMHC (in absence or presence of IL-2), or PIC with both pMHC and IL-2 attached (PIC-pMHC/IL-2), in X-Vivo medium containing 2% human serum at 37° C. After 24 h, supernatant was collected for ELISA measurement of IFNγ concentrations.

Human T Cell Activation Assays

Peripheral blood lymphocytes were isolated from buffy coats, obtained from healthy donors using Ficoll density centrifugation. T cells were isolated from peripheral blood lymphocytes with the Miltenyi Pan T cell isolation kit. To follow T cell proliferation, Celltrace Violet was added to the cells at a final concentration of 2.5 µM. The labelling reaction was performed for 15 min at room temperature. The reaction was quenched upon addition of 3 reaction volumes of cold Fetal Bovine Serum (FBS), followed by washing the cells 3 times. The PIC-protein conjugates were added to Celltrace Violet labelled T cells (50.000) to obtain a final concentration of 100 ng/ml or 500 ng/ml of PIC-conjugated αCD3. Incubation was performed in round-bottom 96-well cell culture plates, with final volumes of 100 µl per well. Cell culture was performed at 37° C. using X-Vivo medium, containing 4% human serum.

Analysis of T Cell Stimulation

After 16 h of stimulation, a fraction of the cells was collected for analysis. The supernatants were collected for ELISA measurements to determine the concentrations of IFNγ (human IFNγ ELISA, Thermo Scientific), IL-2 (ready-set go IL-2 ELISA kit, eBioscience) and TNFα (ready-set go TNFα ELISA kit, eBioscience). For detection, absorbance was measured at 450 nm on a Bio-rad iMark plate reader. The respective cytokine concentrations were determined using 4-paramater fits in Microplate Manager 6 software. In addition, to assess binding of the conjugates and the T cell activation status, T cells were stained for CD4, CD8 and CD25 expression and measured using a BD FACSverse flow cytometer.

Analysis of T Cell Proliferation

After 3 days, the supernatants were collected for IL-2 and TNFα ELISAs, and the cells were stained for CD4 and CD8. CD4 and CD8 expression as well as the dilution of the Celltrace Violet label was determined using FACS (BD FACSVerse). The mean number of cycles (i.e. the average number of cell divisions) was determined as 2log of the ratio of the mean fluorescence intensity (MFI) of non-divided cells (as determined using FlowJo) divided by the MFI of all cells.

To determine long-term T cell proliferation (7 days), T cells were stimulated with 100 ng/ml of the respective PIC-protein conjugates or with CD3/CD28 T cell activator Dynabeads in a 2:1 bead:cell ratio. After 7 days, the cells were stained for CD4 and CD8 and counted using a Miltenyi MACSQuant Analyzer 10. Propidium iodide staining (1:1000 dilution) of dead cells was done using MACSQuant before flow cytometry measurements.

Binding Analysis Using Activated T Cells

To determine binding to activated CD25-positive cells, T cells were stimulated with CD3/CD28 T cell activator Dynabeads in a 1:1 bead:cell ratio at 37° C. in X-vivo medium, containing 4% human serum. After 24 h, the beads were removed over a Dynal MPC-L Magnetic Particle Concentrator (2×). After this step, the PIC-protein conjugates were added to 50.000 of activated T cells and cultured at 37° C. After 16 h, the cells were collected, stained for CD4, CD8 and CD25. Binding of IL-2 was analyzed on the BD FACSverse flow cytometer.

Long-Term T Cell Functionality Assay

Pan T cells were isolated from healthy peripheral blood lymphocytes using a Miltenyi Pan T cell isolation kit. The cells were stimulated with the PIC-protein conjugates, using an αCD3-concentration of 500 nm/ml and CD3/CD28 human T cell activator Dynabeads in a 2:1 bead:cell ratio in X-vivo medium, containing 4% human serum at 37° C. After 7 days, the cells were washed with X-vivo medium and a fraction of the cells was re-stimulated with the same concentration of stimulant. After 14 days, a portion of the T cells was stimulated with PMA and ionomycin for 6 h to induce cytokine production in the presence of Brefeldin A and monensin to trap the cytokines in the cells. The cells were fixed and permeabilized with the BD cytofix/cytoperm kit, and stained for intracellular IL-2, IFNγ and TNFα. In addition, 14-day-stimulated T cells were incubated with PMA and ionomycin for 6 h (to induce degranulation of cytotoxic granules) in the presence of Brefeldin A, monensin and anti-CD107a-PECy5 antibody. After stimulation, intracellular staining for Granzyme B was performed. Additionally, surface staining for PD-1 was done (14-day-stimulated T cells). All stained T cells were measured using the BD FACSverse flow cytometer.

Data Analysis

Flow cytometry data was analysed using FlowJo software. Each experiment was performed with T cells from 3 different donors. Each donor was measured in duplicate and the corresponding values were averaged. To account for variations between donors, all conditions measured with samples from the same donor were first normalized by dividing each value by that of the most important condition. After this step, the mean and the standard error of the mean (SEM) were calculated, using the normalized values of the different donors. Statistical analysis was performed using GraphPad Prism (5.03) software. Statistical significances were calculated with one-way ANOVA and Bonferroni post-tests. P values of 0.05 or less were considered significant. Bar graphs show the mean±SEM of calculated values.

Results

Synthesis and Characterization of IL-2-Functionalized sDCs

To create PIC nanofilaments according to the invention, an azide-functionalized PIC-polymer was synthesized according to Scheme A. As described in the Method section above, an azide-terminated monomer was co-polymerized with a non-functional methoxy-terminated monomer in a ratio chosen such that the polymer statistically yielded an azide group every 3.5 nm.31-33 The obtained polymers had a length of ~400 nm, as measured by atomic force microscopy (AFM) (FIG. 1).

To facilitate purification of the PIC-protein conjugates with a recently introduced affinity-based method, 50% of the azide groups were converted to biotin. The remaining azide handles were utilized to couple anti-CD3 (αCD3) and IL-2.

For this purpose, αCD3 and IL-2 were functionalized with dibenzylcyclooctyne (DBCO)-PEG4-NHS esters and NHS esters of Atto488 (A488) or AlexaFluor647 (AF647), respectively (FIG. 2A). Subsequently, the PIC-protein conjugates were synthesized using strain-promoted azide alkyne cycloaddition (SPAAC) of the fluorescent and DBCO-labelled proteins to the biotin-functionalized azido-PIC polymers (FIG. 3). The fluorescent dyes coupled to both antibody and IL-2, as well as the circular dichroism signal of the PIC polymers (a consequence of the helical polymer backbone), allowed for the straightforward quantification and characterization of the purified sDCs, including their degree of functionalization with αCD3 and IL-2.

Table 1 summarizes the main characteristics of the PIC-protein conjugates used in this study. On average, all synthesized conjugates contain one αCD3 antibody every 140-200 nm (~3 antibodies per polymer). While similar amounts of αCD3 are present, the IL-2 densities vary, depending on the amount of DBCO-IL-2 added to the reaction mixture. In total, PIC nanofilaments with three different IL-2 densities were synthesized: P-αCD3/IL2low, P-αCD3/IL2med and P-αCD3/IL2high. These PIC filaments contain one molecule of IL-2 within every 190, 130 and 40 nm, respectively. Thus, on average, P-αCD3/1L-2low is functionalized with ~2 molecules of IL-2, whereas P-αCD3/IL-2med contains ~4 and P-αCD3/IL-2high carries ~10 IL-2 molecules.

TABLE 1

| Sample name | Spacing αCD3(nm) | Spacing IL-2(nm) | Ratio IL-2/αCD3 |
|---|---|---|---|
| P-αCD3 | 146 ± 3 | | |
| /IL-2low | 167 ± 5 | 194 ± 7 | 0.9 |
| /IL-2med | 206 ± 8 | 125 ± 5 | 1.7 |
| /IL-2high | 143 ± 9 | 40 ± 2 | 3.9 |
| P-IL-2low | | 402 ± 27 | |
| P-IL-2high | | 44 ± 5 | |

In addition, two polymers containing only IL-2 were synthesized: P-IL-2low and P-IL-2high. P-IL-2low carries one IL-2 within every 400 nm (on average ~1 IL-2 per polymer) and P-IL-2high contains one IL-2 every 40 nm (on average ~9 IL-2 per polymer). Furthermore, PIC nanofilaments were synthesized that contained only αCD3 in a density similar to that of P-αCD3/IL-2 PIC nanofilaments: P-αCD3.

As demonstrated in Hammink 2017, biotin-functionalized PIC-protein conjugates can be efficiently purified over monovalent avidin beads. This was verified for the PIC-IL-2 conjugates using SDS-PAGE (FIG. 4). For the PIC-IL-2 conjugates tested, no protein band is visible in the gel. Due to their large size, PIC-protein conjugates cannot enter the gel so that the absence of IL-2 demonstrates the high purity of the PIC nanofilament samples.

PIC-Bound IL-2 Induces Efficient T Cell Activation

In natural immune responses, IL-2 is mostly active as a soluble cytokine, whereas immobilization of this cytokine onto a more rigid aAPC surface impedes activity (Steenblock et al. *J. Biol. Chem.* 2011, 286, 34883-34892, incorporated herein by reference). To analyse the binding and stimulatory capacity of IL-2 when immobilized on PIC nanofilaments according to the invention, the newly synthesized P-αCD3/IL-2 polymers were tested with human T cells.

T cells were isolated from peripheral blood of healthy donors and stimulated with P-αCD3/IL-2 polymers functionalized with varying IL-2 densities.

For all IL-2 densities, IFNγ secretion by T cells was increased at least two-fold after 16 h, compared to the control polymer, functionalized with αCD3 only (P-αCD3). The optimal αCD3/IL-2-ratio was found on P-αCD3/IL-2med, which increased IFNγ secretion 5-fold (FIG. 5A).

In addition, incubation with P-αCD3/IL-2 lead to activation-induced expression of the IL-2 receptor (CD25). Expression was significantly increased and followed a similar dependence on IL-2 density (FIG. 6C). Furthermore, T cell proliferation was increased after three subsequent days of incubation with P-αCD3/IL-2 (FIGS. 5B and 6D), also demonstrating that IL-2 is active when bound to PICs. As demonstrated using A488-labelled-αCD3 (FIG. 6A) and AF647-labelled IL-2 (FIG. 6B), the amount of αCD3 bound to T cells was not significantly affected when comparing the different PIC nanofilaments, while the amount of bound IL-2 showed the expected increase when using PIC nanofilaments with higher IL-2 densities. Together, these measurements indicate that IL-2 is active when coupled to PICs and that the binding of P-αCD3/IL-2 to T cells is predominantly αCD3-dependent. P-αCD3/IL-2med contained the most potent ratio of αCD3 and IL-2 and was, therefore, selected for further studies.

CD3-Targeting of PIC-IL-2 Conjugates Significantly Increases Cytokine Activity

Having established that IL-2-functionalized PICs induce strong T cell responses, we analysed the exact role of the polymer scaffold in IL-2 presentation. Purified human T cells were stimulated with P-αCD3/IL-2med and, alternatively, with the corresponding concentrations (as determined through AF647 fluorescence) of P-IL-2 or unbound IL-2 in the presence of P-αCD3. Although IFNγ secretion induced by P-IL-2+P-αCD3 was two-fold lower compared to the same concentration of unbound IL-2+P-αCD3, targeting P-IL-2 to CD3 by co-conjugation of αCD3 on one and the same PIC (P-αCD3/IL-2med) restored IFNγ levels to those that can be achieved with unbound IL-2+P-αCD3 (FIG. 7A).

A comparable trend was observed for the secretion of TNFα (FIG. 8A). Along the same way, when compared to unbound IL-2+P-αCD3, the induction of CD25 expression (FIG. 8E) and T cell proliferation (FIGS. 7B and 8D) was reduced for P-IL-2+P-αCD3-stimulated CD8+ T cells, but was again increased to higher levels for P-αCD3/IL-2med. This increase points towards a synergistic effect when co-delivering αCD3 and IL-2 on one and the same polymer.

To explain this phenomenon, we quantified the amount of IL-2 bound to T cells exploiting the AF647 signal. Indeed, binding of P-IL-2 is greatly reduced compared to that of unbound IL-2 when used in combination with P-αCD3, probably due to steric hindrance. This reduced binding, which explains the lower stimulatory capacity, can be restored by CD3+ T cell-targeting using P-αCD3/IL-2med (FIGS. 7C and 8C). For each condition, comparable levels of αCD3 were bound to the stimulated T cells (FIG. 8B).

The increased amount of bound IL-2 when using P-αCD3/IL-2med can only partly account for the observed increase in proliferation. On top of this, the observed synergistic effect could be the result of co-localized TCR (CD3) and IL-2 signalling, especially since components of the IL-2 receptor complex can be present in clusters together with (co-receptors of) TCRs.

In addition, localized paracrine delivery can greatly enhance stimulatory capacity of IL-2. Also in natural DC-T cell or T-T cell interactions, synapses formed where TCR clusters are present may facilitate polarized IL-2 release. Similarly, we observed that after PIC nanofilament stimulation, TCRs polarize and form immune synapse-like structures on one side of the T cell. Thus, polarization of IL-2 signalling complexes to these synapses could allow for more efficient IL-2-induced signalling and explain the synergistic effect of closely spaced αCD3 and IL-2.

T cells can bind IL-2 through either the high affinity trimeric αβγ-receptor, or, as happens in the absence of IL-2Rα (CD25), via the low affinity dimeric βγ-receptor. While non-activated T cells only express the low affinity receptor, CD25 is upregulated upon TCR stimulation and the affinity towards IL-2 increases. CD25 is also expressed on other (immune) cells, including endothelial cells that are thought to be responsible for part of the side effects of soluble IL-2 therapy. To investigate the response of CD25-positive cells when stimulated under different IL-2 treatment regimens, T cells were first activated with the commonly used CD3/CD28 Dynabeads to activate T cells and induce CD25 expression. Next, these CD25 high T cells were incubated with unbound IL-2+P-αCD3, P-IL-2 +P-αCD3 or P-αCD3/IL-2med. Binding of IL-2 to activated T cells was increased in all three cases, indicating that binding to CD25-positive T cells is not exclusively dependent on αCD3 (FIG. 8F-G). Importantly, P-IL-2 treatment showed the lowest amount of bound IL-2, also for CD25-high T cells. Therefore, decreased P-IL-2 binding may reduce off-target effects of PIC-cytokine conjugates in future therapeutic applications, even though a possible effect on other cells still needs to be investigated.

To determine whether dangerous off-target binding is indeed reduced, binding of IL-2 to endothelial cells was investigated. For this, human umbilical vein endothelial cells (HUVECs) were incubated with unbound IL-2+P-αCD3, P-IL-2+P-αCD3 or P-αCD3/IL-2med (FIG. 8I). Binding of P-IL-2 and P-αCD3/IL-2med to HUVECs was markedly decreased compared to binding of unbound IL-2, further demonstrating that off-target binding is reduced when IL-2 is conjugated to PICs. Furthermore, HUVEC binding of P-IL-2 and P-αCD3/IL-2med was similar, which indicated that IL-2 binding is not impacted by steric hindrance of close-by PIC-bound antibodies.

Together, the synergistic effect of co-targeting IL-2 and αCD3 shows that IL-2 exerts its highest activity on cells that are simultaneously triggered via αCD3. These results, therefore, clearly demonstrate the potential of PICs as a scaffold for IL-2 immobilization and T cell targeting.

IL-2 Activity is Abrogated When Presented on Solid Microbeads

Having determined that IL-2 can be efficiently presented to T cells on PIC nanofilaments according to the invention, we investigated the activity of IL-2 when conjugated to prior art microbead-based aAPCs. Such rigid microparticles, coated with antibodies against CD3 and CD28, are routinely used for in vitro T cell expansion.

To synthesize αCD3 and IL-2-coated beads, tosyl-actived microbeads were reacted with NH2-PEG5-azide. The resulting azide-functionalized beads were then mixed with DBCO-labelled αCD3 to yield αCD3-functionalized microbeads B-αCD3. Following this step, one fraction of these αCD3-beads was reacted with DBCO- and AF647-labelled IL-2 to obtain B-αCD3/IL-2. Flow cytometry analysis demonstrated that microbeads were positive for fluorescently labelled αCD3 and IL-2 (FIG. 8H). Bead-conjugated αCD3 and IL-2 concentrations were determined, measuring A488 and AF647 fluorescence of unreacted proteins in the supernatant. Stimulation of T cells with unbound IL-2+B-αCD3 induced modest secretion of IFNγ, which was absent when the same amount of IL-2 was conjugated onto these aAPCs (B-αCD3/IL-2; FIG. 9A). Additionally, some proliferation of CD8+ T cells was observed when the T cells were stimulated with unbound IL-2+B-αCD3, while B-αCD3/IL-2-stimulated T cells did not proliferate at all (FIG. 9B).

These experiments demonstrate that IL-2 presentation is not effective on conventional aAPCs, while it induces strong T cell activation when presented on the more flexible PIC nanofilaments. Similarly, IL-2 presentation on αCD3/αCD28-coated PLGA particles is known to be inefficient and requires high IL-2 densities for stimulating T cells.

In contrast to rigid particles, liposome-conjugated IL-2 retain activity towards T cells, which could result from the mobility of liposome-anchored molecules, although the use of Fc-bound IL-2 could also play a role here (Kwong et al, *Cancer Res.* 2013, 73, 1547-1558). In addition, no negative effect of IL-2 surface conjugation was reported when using hydroxyethyl starch nanocapsules (Frick et al. *ACS Nano* 2016, 10, 9216-9226). As rigid microparticles are not able to present active IL-2, size and/or nano-scale flexibility seem to be essential for the activity of immobilized IL-2. This observation is also in line with our result that the amount of T cell bound P-IL-2 is low.

By contrast, for our semi-flexible PICs when IL2 was co-conjugated with αCD3 to the same polymer T cell responses greatly increase. In addition, the multivalent presentation of both αCD3 and IL-2 seems to play an important role in this synergistic effect, since αCD3-IL-2 fusion proteins does not show the same synergy. Without being bound by theory, it is hypothesised that flexible scaffolds that can dynamically rearrange are better mimics of natural DC surfaces, facilitating a more efficient interaction of multiple ligands with T cells.

Semi-flexible PIC scaffolds consequently allow for presenting IL-2 in close spatial proximity with a TCR trigger, resembling the trans-presentation observed in natural immune synapses formed between DCs and T cells. In this case, IL-2 can be presented on the DC surface by CD25, which is located in close proximity to peptide-MHC complexes, leading to robust T cell responses. In summary, our results demonstrate that classical solid microparticles are less suitable as scaffolds for IL-2-presentation, while IL-2-conjugation to PIC nanofilaments according to the invention can induce excellent T cell responses.

Synthesis and Characterization of IFNα-Functionalized PIC Backbones

Having demonstrated the suitability of PIC scaffolds for IL-2 presentation, we next determined whether this sDC design can also be used for targeting other types of cytokines. IFNα is known to play an important role in anti-viral immune responses and is produced in large quantities by plasmacytoid dendritic cells. As a signal 3 cytokine, IFNα stimulates T cells in combination with CD3-stimulation and co-stimulation to promote the acquisition of effector functions and to enhance cell proliferation. In this way, IFNα stimulation contributes to the differentiation of CD4+ T cells into type 1 helper cells (Th1), increases IFNγ secretion and induces the expression of cytotoxic molecules in CD8+ T cell. However, when stimulation of IFNα is not combined with a TCR trigger, T cell proliferation is inhibited. Thus, combining this cytokine on a PIC scaffold could both target this cytokine to T cells and at the same time link these two signals, thereby avoiding inhibition of T cell proliferation.

P-αCD3/IFNα conjugates were synthesized according to the same method as described above for P-αCD3/IL-2 conjugates. In the first step, DBCO-PEG4-NHS ester and AF647-NHS ester were conjugated to IFNα (FIG. 2B). The biological activity of the resulting DBCO- and AF647-functionalized IFNα was equally effective as the unconjugated cytokine, as determined in a T cell proliferation assay using in Dynabead-stimulated human T cells (FIG. 10A). Subsequently, the functionalized cytokine was reacted with the azide-biotin-PICs. The resulting IFNα-PIC conjugates were purified over magnetic mono-avidin beads.

After purification, the protein concentration on the PIC-protein conjugates was analyzed, using fluorescence and circular dichroism as described before. Again, different PIC nanofilaments with different IFNα densities were prepared and characterized with fluorescence and circular dichroism measurements. The spacings between IFNα molecules were 190 nm (P-αCD3/IFNαlow), 90 nm (P-αCD3/IFNαmed) and 40 nm (P-αCD3/IFNαhigh). This corresponds to 2, 4 and 10 molecules of IFNα per polymer. For the different samples with varying IFNα densities, the average αCD3 spacing varied between 90-130 nm (Table 2). On average, these conjugates contained ~4 antibodies per polymer. Also, PICs containing only IFNα were synthesized with two different densities. P-IFNαlow contained ~2 proteins per PIC (spacing of 200 nm) and P-IFNαhigh carried ~8 proteins (spacing of 50 nm). SDS-PAGE revealed that only low amounts of unconjugated cytokine were present in the purified samples (FIG. 11).

TABLE 2

| Sample name | Spacing αCD3(nm) | Spacing IFNα(nm) | Ratio IFNα/αCD3 |
|---|---|---|---|
| P-αCD3 | 108 ± 22 | | |
| /IFNαlow | 130 ± 9 | 192 ± 11 | 0.7 |
| /IFNαnamed | 120 ± 13 | 91 ± 11 | 1.3 |
| /IFNαhigh | 88 ± 8 | 38 ± 3 | 2.3 |
| P-IFNαlow | | 205 ± 13 | |
| P-IFNαhigh | | 47 ± 2 | |

PIC-conjugated IFNα Induces T Cell Activation and Proliferation

Stimulation of T cells with P-αCD3/IFNα with varying cytokine densities induced the increased secretion of IFNγ compared to the P-αCD3 control, demonstrating that also this cytokine is functional when conjugated to PICs (FIG. 12A). In contrast to P-αCD3/IL-2, no clear pattern emerges when investigating the binding of P-αCD3/IFNα with different IFNα densities, possibly because this interaction does not dependent on CD3 (FIGS. 10B and 10C).

To establish how PIC-conjugated IFNα affects T cells, the cells were stimulated with unbound IFNα+P-αCD3, P-IFNα+P-αCD3 and P-αCD3/IFNhigh. For these three conditions, little differences were observed when comparing the amount of IFNα bound to T cells. All three conditions also induced comparable amounts of IFNγ secretion (after 16 h; FIG. 12B), demonstrating that IFNα conjugation to PICs does not reduce its initial activity.

When analysing T cells 3 days after stimulation, no significant influence of IFNα on T cell proliferation could be detected (FIGS. 10F and 10G). Since IFNα is known to support T cell proliferation at later stages after TCR stimulation, cell numbers were assessed 7 days after stimulation. At this time point, P-αCD3/IFNα stimulation increased CD8+ T cell numbers more than four-fold compared to P-αCD3-stimulated cells, both in the presence or absence of unbound IFNα (FIG. 12C).

Similar to the enhanced proliferation observed after stimulation with P-αCD3/IL-2, this enhanced effect of P-αCD3/IFNα could be the result of co-triggering IFNα receptors in close proximity to CD3. Indeed, TCRs and IFNα share similar early signalling complexes and functional TCRs are required for efficient IFNα signaling, which could indicate co-localization of both receptors. In addition, for IFNγ receptors, which are related to IFNα receptors, inclusion within immune synapses in CD4+ T cells has been described as a mechanism to enhance signal transduction.

These results clearly illustrate that PIC-conjugated IFNα can stimulate T cells to induce IFNγ secretion and (late) proliferation. Accordingly, IFNα can be readily conjugated to PICs without losing its stimulatory capacity. Importantly, stimulation with P-αCD3/IFNα leads to a significant increase in the CD8+ T cell number after 7 days.

T Cells Stimulated with PIC-Conjugated Cytokines Develop Multiple Effector Functions After having confirmed that P-αCD3/IL-2 and P-αCD3/IFNα are capable of targeting cytokines to T cells and of inducing potent T cell responses, we investigated the functionality of the stimulated T cells after 14 days. Different functionalities of T cells, such as cytokine production and cytotoxicity, determine their capacity to induce a potent immune response.

Expression of pro-inflammatory cytokines IL-2, IFNγ and TNFα can be essential in anti-tumor immunity, especially when produced in combination, each having their own role in orchestrating an immune response. Cytokines are known to be important for equipping T cells with these functionalities. To ensure that the desired immune response is not affected when stimulating T cells with the PIC nanofilaments, it is advantageous if these functions are preserved after stimulation with cytokine-functionalized PICs.

To determine these functionalities, T cells were stimulated with PIC nanofilaments (or Dynabeads as a positive control for long-term T cell expansion) and re-stimulated after 7 days. After 14 days, intracellular staining for IL-2, IFNα and TNFα was performed to determine the percentage of cells capable of producing these cytokines.

Long-term stimulation resulted in T cells capable of producing multiple cytokines, demonstrating the presence of functional T cells. Stimulation with P-αCD3/IFNα induced high numbers of IFNγ-producing T cells, but led to a decrease in TNFα-producing cells. For IL-2-stimulated cells, a decrease in IL-2 production was observed (FIGS. 13A and 13B). In general, the stimulation with cytokine-functionalized sDCs resulted in cytokine expression profiles comparable to stimulation with unconjugated cytokines (FIGS. 14A and 14B), further demonstrating that IL-2 and IFNα are still fully capable of exerting their function after conjugation to PICs.

One of the most important functions of T cells, especially for CD8+ cells, is to kill pathogen infected cells or cancer cells through the release of granules that contain cytotoxic molecules, such as Granzyme B. As the release of cytotoxic molecules from these vesicles exposes CD107a on the cell surface, this can be used as a surrogate marker for cytotoxic activity and measured by flow cytometry.

After 14 days of stimulation, T cells expressed high levels of CD107a and Granzyme B, demonstrating their capacity of killing target cells (FIGS. 13C and 13D). Especially after stimulation with IFNα, expression of the degranulation marker CD107a was significantly increased, while degranulation in IL-2-stimulated cells was lower. Degranulation was not dependent on whether IL-2 and IFNα were conjugated to PICs during stimulation (FIG. 14C), whereas Granzyme B levels were somewhat increased when using PIC-cytokine conjugates for stimulation (FIG. 14D). These findings demonstrate that IL-2- and IFNα-induced cytotoxic T cell functions are retained or slightly increased upon P-αCD3/cytokine stimulation. Complying with their cytotoxic function, CD8+ T cells were the main producers of Granzyme B, although CD4+ T cells also showed degranulation and some Granzyme B production. Indeed, similar to CD8+ T cells, CD4+ T cells have recently been found to be capable of antigen-specific cytotoxicity in some cases.

Besides showing expression of cytotoxic markers, cell surface expression of PD-1 was determined after 14 days. Interaction of PD-1 with its ligand, PD-L1, restrains T cell activity and can inhibit T cell function. Expression levels of PD-1 are therefore an indication of the ability of a T cell to be functional within immunosuppressive environments, including many tumours.

After stimulation with P-αCD3/IFNα, T cells expressed relatively low levels of PD-1, while the PD-1 expression level for P-αCD3/IL-2-stimulated cells was higher and more comparable to the expression level of Dynabead-stimulated T cells (FIG. 13E). The relatively low expression of PD-1 on IFNα-stimulated cells might make T cells less susceptible to PD-L1-expressing tumour cells or APCs, and is thus beneficial for their functionality.

Together, these experiments demonstrate that T cells stimulated with cytokine-functionalized PICs are capable of producing multiple cytokines and of expressing cytotoxic markers. Although IFNα-stimulated T cells exhibit lower proliferation than IL-2 treated cells, they are potentially more capable of killing their target cells. On top of this, their relatively low PD-1 expression makes them less susceptible for inhibition by PD-L1. Taken together, co-conjugation of αCD3 and cytokines to PIC nanofilaments according to the invention increases the early activation and proliferation of T cells, while retaining the capacity of these cytokines to bring about important functional characteristics in these T cells.

Concomitant T Cell Stimulation with PIC-Conjugated IL-2 and IFNα Induces Both Strong Proliferation and High Cytotoxic Function The previous experiments demonstrated that PIC-bound IFNα markedly enhanced cytotoxic effector functions of T cells. At the same time, stimulation of T cells with PIC-bound IL-2 leads to high levels of early proliferation, while IFNα stimulation only increased T cell numbers after 7 days. Nonetheless, compared to stimulation with P-αCD3/IFNα, P-αCD3/IL-2 induces higher numbers of both CD4+ and CD8+ T cells at this time point. Therefore, it was assessed whether the potency of P-αCD3/IL-2 can be combined with the capacity of PaCD3/IFNα to induce important functional features in T cells at later time points.

For this, T cells were first primed by incubation with P-αCD3/IL-2 for 3 days, after which cells were washed and either re-stimulated with P-αCD3/IL-2, re-stimulated with P-αCD3/IFNα, or not re-stimulated. Re-stimulation of T cells with P-αCD3/IL-2 increased expression of degranulation marker CD107a after 7 days, which was increased even further in T cells re-stimulated with P-αCD3/IFNα (FIG. 15a). Upregulation of Granzyme B expression was comparable for both re-stimulation with P-αCD3/IL-2 and P-αCD3/IFNα. In contrast to the priming experiments described above, P-αCD3/IFNα re-stimulation did not reduce PD1 expression compared to the T cells with P-αCD3/IL-2, which indicates that expression of PD-1 is not actively reduced by P-αCD3/IFNα. Importantly, cell numbers of P-αCD3/IL-2 and P-αCD3/IFNα re-stimulated cells were comparable (FIG. 15b). Taken together, these experiments demonstrate that re-stimulation of P-αCD3/IL-2-primed T cells with P-αCD3/IFNα generates large numbers of T cells with a high expression of cytotoxic markers. This shows that the capacity of P-αCD3/IL-2 to induce early T cell proliferation can indeed be combined with the induction of cytotoxic functionality by P-αCD3/IFNα.

Besides using separate sequential stimulations, the biological activity of these novel cytokine-functionalized sDCs may be further optimized when combining these two different cytokines on a single CD3-targeting PIC, because this approach ultimately allows for simultaneous delivery of both IL-2 and IFNα to the same T cell.

To generate these PIC—protein conjugates that contain αCD3, as well as both IL-2 and IFNα, PIC-protein conjugates were synthesized by reacting the three different DBCO-labelled proteins to biotin-functionalized azido-PIC polymers and the resulting PIC-protein conjugate was purified as described before. The P-αCD3/1L-2/IFNα conjugate had an αCD3 density of 75 nm +/−7 nm, and a total cytokine density of 141 nm +/−14 nm. Density of individual cytokines could not be measured directly since both cytokines were labelled with the same dye. Taking a ratio of 1.5:1 II-2:IFNα (the same ratio at which the cytokines were reacted with the polymer) individual densities were inferred to be approximately IL-2: 235 nm and IFNα: 352 nm. These densities were used for the experiments described below, but have not been optimized. Optimization of the densities could provide further improvements in the effects of the nanofilaments.

T cells were stimulated with this P-αCD3/1L-2/IFNα conjugate, P-αCD3/IL-2, or P-αCD3+IL-2+IFNα and after 7 days cells were counted and analysed for their functional properties. In both CD4+ and CD8+ T cells stimulated with P-αCD3/IL2/ IFNα, CD107a expression was increased more than twofold compared to T cells stimulated with P-αCD3/IL-2 (FIG. 15c). This expression level was comparable to cells stimulated with P-αCD3 mixed with unbound cytokines. In addition, stimulation with P-αCD3/1L-2/IFNα and P-αCD3+IL-2+IFNα increased the expression of cytotoxic marker Granzyme B, further demonstrating the capacity of combining PIC-immobilized IL-2 and IFNα stimulation for the induction of cytotoxic effector functions in T cells. Again, PD1 expression was similar for all three conditions. Importantly, the number of cells was similar after stimulation with P-αCD3/1L-2/IFNα, P-αCD3+IL-2+IFNα, and P-αCD3/IL-2 (FIG. 15d). Taken together, IL-2 and IFNα can be combined on one and the same sDC to induce both strong proliferation and cytotoxic function in T cells.

Evidence demonstrating the efficacy of nanofilaments according to the invention is also provided in Eggermont L J, et al. Cytokine-functionalized Synthetic Dendritic Cells for T Cell Targeted Immunotherapies. *Advanced Therapeutics*, 1(6), 2018, 1800021, which is incorporated by reference in its entirety).

Nanofilaments of Alternative Semi-Flexible Polymers Provide Potent IL-2 Activity To investigate if the activity of IL-2 was similarly potent using nanofilaments comprising alternative polymeric scaffolds to polyisocyanopeptides, we synthesized alginate polymers with αCD3 with and without IL-2. Alginate is another semi-flexible polymer backbone.

Purified human T-cells were stimulated with these alginate conjugates and proliferation was examined. As expected, stimulation with only αCD3 conjugated alginate did not lead to any proliferation of the T-cells. When IL-2 was co-conjugated to the scaffold, T-cells started to proliferate at improved or comparable levels to soluble IL-2 treatment (FIG. 16). Taken together, these measurements show that IL-2 activity is retained on nanofilaments with semi-flexible polymeric scaffolds like alginate or polyisocyanopeptides, but not on micrometer sized, rigid bead scaffolds (see for example FIG. 9).

MHC-Functionalised Nanofilaments Provide Antigen-Specific T Cell Stimulation

To demonstrate that nanofilaments according to the invention are able to deliver antigen-specific stimulation when functionalised with MHC-antigen complexes, PIC nanofilaments were functionalised with HLA-A201 MHC presenting the NY-ESO-I peptide (pMHC). T cells from a healthy donor were transfected with mRNA encoding a TCR specific for NY-ESO-I presented in the context of HLA-A201. The NY-ESO-I specific T cells were then contacted with nanofilaments displaying pMHC in the presence and absence of soluble IL-2 (FIG. 17, PIC-pMHC+IL-2, and PIC-pMHC, respectively). NY-ESO-I specific T cells were also contacted with PIC nanofilaments functionalised with both pMHC and IL-2 (FIG. 17, PIC-pMHC/IL-2). Finally, T cells were also contacted with soluble pMHC and soluble IL-2 (FIG. 17, pMHC+IL-2). IFNγ production was measured as an indication of antigen-specific T cell activation in response to the treatment conditions.

As shown in FIG. 17, nanofilaments functionalised with a MHC-antigen complex activate T cells specific for the MHC-presented antigen when in the presence of IL-2. The activation is particularly potent when the IL-2 is co-presented by the nanofilament—that is, when the nanofilament is co-functionalised with the antigen-MHC complex and the cytokine. Without wishing to be bound by theory, this is hypothesised to be due to the semi-flexible nature of the nanofilaments allowing colocalisation of the MHC-antigen binding protein and cytokine such that they can form a potently stimulatory immune synapse with the T cells.

Conclusions

Cytokine-functionalized PIC nanofilaments were successfully synthesized and applied in T cell activation experiments, as were PIC nanofilaments containing αCD3 antibodies combined with IL-2 or IFNα. Although IL-2 and IFNα are cytokines with distinct functional and structural characteristics, both of them could be efficiently conjugated to PICs and remain biologically active.

For both cytokines, proliferation was enhanced when cells were stimulated with PICs that were functionalized with both αCD3 and cytokines. Co-conjugation of αCD3 targeted IL-2 conjugates to the CD3 receptor greatly increased all aspects of T cell activation. PIC-filaments are therefore a potent scaffold for the presentation of IL-2 to T cells. Alginate filaments decorated with IL-2 and αCD3 antibodies were also shown to stimulate T cell proliferation.

PIC-conjugation of IFNα was mostly beneficial for the induction of late T cell proliferation as well as for the induction of potent cytotoxic functionality. Thus, these experiments demonstrate that IL-2-presenting PIC nanofilaments are especially advantageous for enhancing T cell proliferation, while IFNα-functionalized PICs are particularly effective for inducing more potent T cells.

The biological activity of these novel cytokine-functionalized sDCs may be further optimized when combining these two different cytokines on a single CD3-targeting nanofilament. This approach allows for more substantial T cell proliferation combined with the induction of strong cytotoxic effector function, leading to high numbers of highly effective cytotoxic T cells.

Thus, cytokines were targeted to T cells using αCD3 antibodies, which bind closely to the TCR and generically trigger all CD3 expressing T cells. We have also demonstrated that it is possible to transform this approach towards antigen-specific cytokine delivery, by replacing αCD3 antibodies with peptide-MHC complexes. Such nanofilaments functionalised with antigen-MHC complexes and cytokines are shown herein to effectively target antigen-specific T cells and to induce a potent immune response.

Furthermore, in vivo tumour models will be used to further validate the benefit of cytokine presentation by PIC nanofilaments of the invention. Thus, the results presented herein establish PIC nanofilaments as highly suitable vehicles for the delivery and presentation of otherwise soluble cytokines to T cells. The small size and straightforward synthesis of these conjugates makes them particularly promising for future off-the-shelf immune therapies.

The invention claimed is:

1. A polyisocyanopeptide (PIC) nanofilament comprising a plurality of molecules of a first cytokine attached to a PIC backbone, wherein the cytokine is IL-2 or IFNα, and further comprising a plurality of molecules of a binding molecule attached to the PIC backbone, wherein the binding molecule binds to a molecule presented by a T cell.

2. The PIC nanofilament according to claim 1, wherein the binding molecule binds to a TCR molecule, optionally wherein the binding molecule binds CD3 or a TCR heterodimer.

3. The PIC nanofilament according to claim 1, wherein the binding molecule is an antibody or binding fragment thereof.

4. The PIC nanofilament according to claim 1, wherein the binding molecule is an MHC-antigen complex.

5. The PIC nanofilament according to claim 1, wherein the cytokine is attached to the backbone at a density of at least one molecule each 190 nm, optionally wherein the cytokine is attached to the backbone at a density of one molecule each 130 nm.

6. The PIC nanofilament according to claim 1, wherein 2-10 molecules of the cytokine are attached to the backbone, optionally wherein 4 molecules of the cytokine are attached to the backbone.

7. The PIC nanofilament according to claim 1, further comprising a plurality of molecules of a second cytokine.

8. The PIC nanofilament according to claim 7, wherein the first cytokine is IFNα and the second cytokine is IL-2.

9. The PIC nanofilament according to claim 8, wherein the binding molecule is attached at a density of at least one molecule each 130 nm, optionally wherein the binding molecule is attached at a density of one molecule each 80-130 nm.

10. The PIC nanofilament according to claim 1, wherein 3-5 molecules of the binding molecule are attached to the backbone, optionally 4 molecules.

11. The PIC nanofilament according to claim 1, wherein the cytokine molecules and binding molecules are attached to the PIC backbone via a (poly)ethylene glycol linker comprising 1-10 PEG units, optionally 4 PEG units.

12. The PIC nanofilament according to claim 1, wherein the PIC polymer is obtainable by a method comprising nickel-catalysed polymerization of methoxy-terminated and azide-terminated isocyanopeptide monomers in a ratio of from 50:1 to 10:1.

13. The PIC nanofilament according to claim 12, wherein the PIC polymer is obtainable by a method further comprising conversion of 50% of azide groups to biotin.

14. A composition comprising one or more PIC nanofilaments according to claim 1.

15. The composition according to claim 14, further comprising a second nanofilament, wherein the second nanofilament comprises a plurality of molecules of a second cytokine and/or a plurality of a binding molecule attached to the PIC backbone.

16. A method of modulating an immune response in a human subject comprising contacting a population of immune cells, with a PIC nanofilament according to claim 1 or a composition comprising said nanofilament.

17. A method of treating cancer or immunosuppression in a human subject comprising contacting a population of immune cells, with a PIC nanofilament according to claim 1 or a composition comprising said nanofilament.

\* \* \* \* \*